(12) United States Patent
Nakai et al.

(10) Patent No.: US 7,910,611 B2
(45) Date of Patent: Mar. 22, 2011

(54) THERAPEUTIC AGENT FOR RESTENOSIS

(75) Inventors: Ryuichiro Nakai, Shizuoka (JP); Emi Shimoike, Shizuoka (JP); Hideaki Kusaka, Shizuoka (JP); Chikara Murakata, Shizuoka (JP); Yoshinori Yamashita, Tokyo (JP)

(73) Assignees: Kyowa Hakko Kirin Co., Ltd., Tokyo (JP); Fujifilm Corporation, Tokyo (JP)

( * ) Notice: Subject to any disclaimer, the term of this patent is extended or adjusted under 35 U.S.C. 154(b) by 465 days.

(21) Appl. No.: 11/993,757

(22) PCT Filed: Jun. 22, 2006

(86) PCT No.: PCT/JP2006/312531
§ 371 (c)(1),
(2), (4) Date: Mar. 3, 2008

(87) PCT Pub. No.: WO2006/137490
PCT Pub. Date: Dec. 28, 2006

(65) Prior Publication Data
US 2010/0029625 A1    Feb. 4, 2010

(30) Foreign Application Priority Data
Jun. 24, 2005    (JP) .................. 2005-184430

(51) Int. Cl.
A61K 31/41    (2006.01)
(52) U.S. Cl. .................. 514/363
(58) Field of Classification Search .............. 514/363
See application file for complete search history.

(56) References Cited

U.S. PATENT DOCUMENTS

| | | | |
|---|---|---|---|
| 4,338,449 A | 7/1982 | Tao et al. |
| 4,346,225 A | 8/1982 | Tao et al. |
| 4,699,913 A | 10/1987 | Farooq et al. |
| 4,927,822 A | 5/1990 | Brown et al. |
| 5,643,911 A | 7/1997 | Yamada et al. |
| 5,814,647 A | 9/1998 | Urban et al. |
| 6,207,690 B1 | 3/2001 | Urban et al. |
| 6,235,762 B1 | 5/2001 | Takasugi et al. |
| 6,414,121 B1 | 7/2002 | Wood et al. |
| 6,545,004 B1 | 4/2003 | Finer et al. |
| 6,545,030 B1 | 4/2003 | Barrett et al. |
| 6,562,831 B1 | 5/2003 | Finer et al. |
| 6,630,479 B1 | 10/2003 | Finer et al. |
| 6,831,085 B1 | 12/2004 | Bergnes et al. |
| 6,992,082 B2 | 1/2006 | Finer et al. |
| 7,060,705 B2 | 6/2006 | Fraley et al. |
| 7,105,668 B1 | 9/2006 | Bergnes et al. |
| 7,119,089 B2 | 10/2006 | Finer et al. |
| 7,230,000 B1 | 6/2007 | Finer et al. |
| 2002/0143026 A1 | 10/2002 | Lombardo et al. |
| 2002/0165240 A1 | 11/2002 | Kimball et al. |
| 2003/0008888 A1 | 1/2003 | Kimball et al. |
| 2004/0023996 A1 | 2/2004 | Finer et al. |
| 2004/0087548 A1 | 5/2004 | Salvati et al. |
| 2004/0132719 A1 | 7/2004 | Finer et al. |
| 2004/0132830 A1 | 7/2004 | Finer et al. |
| 2004/0254203 A1 | 12/2004 | Finer et al. |
| 2004/0259826 A1 | 12/2004 | Fraley et al. |
| 2005/0119484 A1 | 6/2005 | Breslin et al. |
| 2005/0187232 A1 | 8/2005 | Finer et al. |
| 2005/0203110 A1 | 9/2005 | Coleman et al. |
| 2006/0014736 A1 | 1/2006 | Finer et al. |
| 2006/0074113 A1 | 4/2006 | Murakata et al. |
| 2006/0100161 A1 | 5/2006 | Hans et al. |
| 2006/0111424 A1 | 5/2006 | Salvati et al. |
| 2007/0112044 A1 | 5/2007 | Murakata et al. |
| 2007/0155804 A1 | 7/2007 | Murakata et al. |
| 2007/0213380 A1 | 9/2007 | Murakata et al. |
| 2007/0254902 A1 | 11/2007 | Finer et al. |
| 2007/0276017 A1 | 11/2007 | Murakata et al. |

FOREIGN PATENT DOCUMENTS

| | | |
|---|---|---|
| DE | 243930 | 3/1987 |
| EP | 0 207 004 | 12/1986 |
| EP | 0 217 519 | 4/1987 |
| EP | 1 004 241 | 5/2000 |
| EP | 1 454 903 | 9/2004 |
| EP | 1 616 866 | 1/2006 |
| EP | 1 632 484 | 3/2006 |
| EP | 1 671 957 | 6/2006 |
| EP | 1 867 640 | 12/2007 |
| EP | 1 870 404 | 12/2007 |
| JP | 62-53976 | 3/1987 |
| JP | 8-34734 | 2/1996 |

(Continued)

OTHER PUBLICATIONS

Agarwal et al. *Nature Reviews Cancer* 3:502-16, 2003.
Alho et al. *Arkivoc* 1(4):627-40, 2000.
Andreae et al. *Journal f. prakt. Chemie* 328(Heft 2):205-14, 1986.
Ashour et al. *Bull. Fac. Pharm. Cairo Univ.* 31(3):381-86, 1993.
Awad et al. *Alex. J. Pharm. Sci.* 3(2):119-21,1989.

(Continued)

*Primary Examiner* — Raymond J Henley, III
(74) *Attorney, Agent, or Firm* — Greenblum & Bernstein, P.L.C.

(57) ABSTRACT

A therapeutic and/or prophylactic agent for restenosis, which comprises a thiadiazoline derivative represented by the general formula (0), or a pharmaceutically acceptable salt thereof:

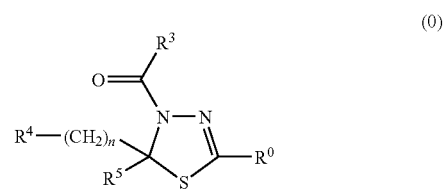

(0)

[wherein, n represents an integer of 1 to 3, $R^0$ represents aryl, —$NR^1CONR^2$ (wherein $R^1$ represents a hydrogen atom or the like, and $R^2$ represents lower alkyl or the like) or the like, $R^3$ represents lower alkyl, $R^4$ represents a hydrogen atom or the like, and $R^5$ represents aryl or the like].

23 Claims, No Drawings

FOREIGN PATENT DOCUMENTS

| | | |
|---|---|---|
| JP | 2000-159756 | 6/2000 |
| JP | 2000-204077 | 7/2000 |
| JP | 2000-229959 | 8/2000 |
| WO | 93/22311 | 11/1993 |
| WO | 00/42029 | 7/2000 |
| WO | 01/30768 | 5/2001 |
| WO | 01/56994 | 8/2001 |
| WO | 01/98278 | 12/2001 |
| WO | 02/056880 | 7/2002 |
| WO | 02/057244 | 7/2002 |
| WO | 02/067939 | 9/2002 |
| WO | 02/079149 | 10/2002 |
| WO | 02/079169 | 10/2002 |
| WO | 03/039460 | 5/2003 |
| WO | 03/051854 | 6/2003 |
| WO | 03/079973 | 10/2003 |
| WO | 2004/039774 | 5/2004 |
| WO | 2004/092147 | 10/2004 |
| WO | 2004/111023 | 12/2004 |
| WO | 2004/111024 | 12/2004 |
| WO | 2005/035512 | 4/2005 |
| WO | 2006/044825 | 4/2006 |

OTHER PUBLICATIONS

Bhalla et al. *European Journal of Medicinal Chemistry* 29:713-17, 1994.
Blangy et al. *Cell* 83:1159-69, 1995.
CAS Registry No. 89992-30-3.
CAS Registry No. 149638-42-6.
CAS Registry No. 149638-44-8.
CAS Registry No. 149638-46-0.
CAS Registry No. 149638-48-2.
CAS Registry No. 149638-50-6.
CAS Registry No. 149638-52-8.
CAS Registry No. 198069-12-4.
CAS Registry No. 292066-09-2.
CAS Registry No. 296801-28-0.
CAS Registry No. 298218-64-1.
CAS Registry No. 300719-38-4.
CAS Registry No. 300808-92-8.
CAS Registry No. 307332-22-5.
CAS Registry No. 307332-24-7.
CAS Registry No. 307332-28-1.
CAS Registry No. 307332-29-2.
CAS Registry No. 307332-30-5.
CAS Registry No. 307332-31-6.
CAS Registry No. 307332-32-7.
CAS Registry No. 313523-88-5.
CAS Registry No. 313523-91-0.
CAS Registry No. 313548-79-7.
CAS Registry No. 313558-45-1.
CAS Registry No. 330683-65-3.
CAS Registry No. 330683-67-5.
CAS Registry No. 332389-23-8.
CAS Registry No. 332389-24-9.
CAS Registry No. 332389-25-0.
CAS Registry No. 332389-27-2.
CAS Registry No. 332389-28-3.
CAS Registry No. 346715-36-4.
CAS Registry No. 350581-79-2.
CAS Registry No. 352225-16-2.
CAS Registry No. 355435-20-0.
CAS Registry No. 356773-12-1.
CAS Registry No. 356773-13-2.
CAS Registry No. 356773-31-4.
CAS Registry No. 356773-79-0.
CAS Registry No. 356773-98-3.
CAS Registry No. 400833-35-4.
CAS Registry No. 405925-79-3.
CAS Registry No. 419551-57-8.
CAS Registry No. 432518-92-8.
CAS Registry No. 432536-58-8.
CAS Registry No. 433235-71-3.
CAS Registry No. 438540-30-8.
CAS Registry No. 442654-91-3.
CAS Registry No. 443105-34-8.
CAS Registry No. 443105-41-7.
CAS Registry No. 443105-46-2.
CAS Registry No. 443105-51-9.
CAS Registry No. 443105-56-4.
CAS Registry No. 443105-64-4.
CAS Registry No. 443105-73-5.
CAS Registry No. 443105-78-0.
CAS Registry No. 443105-83-7.
CAS Registry No. 443105-88-2.
Daub et al. *Nature Reviews Drug Discovery* 3:1001-10, 2004.
Ding et al. *Bioorganic & Medicinal Chemistry Letters* 7(13):1607-10, 1997.
*Dokl. Aka. Nauk SSSR* 296:1133-37, 1987.
El-Khawass et al. *Alex. J. Pharm. Sci* 4(1):77-79, 1990.
English Language Abstract of JP 8-34734, 2008.
English Language Abstract of JP 2000-159756, 2000.
English Language Abstract of JP 2000-204077, 2000.
English Language Abstract of JP 2000-229959, 2000.
Evans et al. *Journal of the Chemical Society*, Perkin Transactions 1, 8:1499-505, 1986.
Farghaly et al. *Arch. Pharm. Pharm. Med. Chem.* 333(2-3):53-57, 2000.
Graubaum et al. *Z Chem.* 26:99-100, 1986.
Habib et al. *Alex. J. Pharm. Sci.* 10(1):53-58, 1996.
Hassan et al. *J. Chem. Research Synopses* 12:544-45, 2000.
Hassan et al. *J. Chem. Research (M)* 1301-15, 2000.
Hassan et al. *J. Saudi Chem. Soc.* 3(2):171-76, 1999.
Hoque et al. *J. Bangladesh Chem. Soc.* 5(2):127-32, 1992.
Huang et al. *Phosphorus, Sulfur and Silicon* 122:307-12, 1997.
*Jikken Igaku (Experimental Medicine)* 17(4):439-44, 1999.
Kabilan et al. *Asian Journal of Chemistry* 14(2):879-83, 2002.
Kapoor, et al. *The Journal of Cell Biology* 150(5):975-88, 2000.
Kapoor, et al. *Proc. Natl. Acad. Sci. USA* 96:9106-11, 1999.
Khalil, M.A. *Alex. J. Pharm. Sci.* 3(2):221-24,1989.
Khalil et al. *Arch. Pharm. (Weinheim)* 326:489-92, 1993.
Khan et al. *J. Pesticide Sci.* 19:305-08, 1994.
*Khim. Geterotsikl. Soedin* 12:1689-97, 1992.
Kuban et al. *Cryst. Res. Technol.* 22(6):799-802, 1987.
Kubota et al. *Heterocycles* 4(12):1909-12, 1976.
Kubota et al. *Heterocycles* 24(1):21-24, 1986.
Kubota et al. *J. Org. Chem.* 45(8):1473-77, 1980.
Kubota et al. *J. Chem. Soc. Chem. Commun.* 16:901-02, 1982.
Lockhart et al. *Biochemistry* 35:2365-73, 1996.
Maliga et al. *Chemistry & Biology* 9:989-96, 2002.
Mandelkow et al. *Trends in Cell Biology* 12:585-91, 2002.
Mayer et al. *Science* 286:971-74, 1999.
Mokhtar et al. *Bull. Pharm. Sci. Assiut University* 18(2):59-67, 1995.
Moses et al. *N. Engl. J. Med.* 349(14):1315-23, 2003.
Nakayama et al. *J. Org. Chem.* 49:1703-07, 1984.
Nofal et al. *Arch. Pharm. Res.* 25(3):250-57, 2002.
Power et al. *J. Chem. Soc. Chem. Commun.* 8:873-74, 1998.
Ross, R. *Nature* 362:801-09, 1993.
Schenone et al. *Bioorganic & Medicinal Chemistry* 9:2149-53, 2001.
Schulze et al. *Zeitschrift fuer Chemie* 29(5):166-167, 1989.
Serruys et al. *N. Engl. J. Med.* 331(8):489-95, 1994.
*Shin-Jikken-Kagaku-Koza*, 14:1142-45 (Maruzen 1978).
Somogyi, L. *Tetrahedron* 47(44):9305-16, 1991.
Somogyi, L. *Tetrahedron* 48(42):9355-62, 1992.
Somogyi, L. *Liebigs Ann. Chem.* 623-27, 1994.
Somogyi, L. *Liebigs Ann. Chem.* 721-24, 1995.
Stone et al. *N. Engl. J. Med.* 350(3):221-31, 2004.
Su et al. *Proc. Natl. Acad. Sci. USA* 99(7):4465-70, 2002.
Szczepankiewicz et al. *J. Med. Chem.* 44(25):4416-30, 2001.
Tao et al. *Heterocycles* 29(1):133-40, 1989.
Tao et al. *J. Heterocyclic Chem.* 21:599-601, 1984.
Temple et al. *J. Med. Chem.* 25:1045-50, 1982.
Thimmaiah et al. *Inorganica Chimica Acta* 107:1-4, 1985.
Turner et al. *The Journal of Biological Chemistry* 276(27):25496-502, 2001.

U.S. Appl. No. 11/909,289 (Murakata et al.) entitled "Therapeutic Agent for Hematopoietic Tumor."

U.S. Appl. No. 11/909,324 (Nakai et al.) entitled "Therapeutic Agent for Hematopoietic Tumor."

U.S. Appl. No. 12/098,736 (Murakata et al.) entitled "Thiadiazoline Derivative."

Wengel et al. *Pestic. Sci.* 30:223-33, 1990.

Ycoba et al. *Khim. Geterotsikl Soedin.* 10:1337-44, 1994.

Yinglin et al. *Synthesis* 28:615-18, 1990.

Zavedenii, I.V.U. *Khimiya I Khimicheskaya Takhnologiya* 43: 64-68, 2000.

Zelenin et al. *Chemistry of Heterocyclic Compounds* 35(1):87-92, 1999.

Zelenin et al. *Zhurnal Organicheskoi Khimii* 20(1):152-62, 1984.

Zelenin et al. *Chemical Abstracts* 97(19):708 Abstract 162877w, 1982.

*Zhurnal Organischeskoi Khimi* 663-664, 1986.

U.S. Appl. No. 60/620,048 to Hans et al., filed Oct. 19, 2004.

THERAPEUTIC AGENT FOR RESTENOSIS

TECHNICAL FIELD

The present invention relates to a therapeutic and/or prophylactic agent for restenosis comprising a thiadiazoline derivative or a pharmaceutically acceptable salt thereof as an active ingredient.

BACKGROUND ART

Percutaneous transluminal coronary angioplasty has been widely performed as a therapeutic method for ischemic heart diseases. However, it is known that restenosis occurs in 30 to 50% of patients after three to six months after the operation due to intimal thickening. A method was developed in which a stenosis lesion is expanded with a balloon catheter, and then a stent is indwelled, and thereby the frequency of restenosis was decreased. However, restenosis is still observed in 10 to 30% of such patients, which arises a problem (N. Engl. J. Med., Vol. 331, p. 489 (1994)).

Thrombogenesis and abnormal proliferation of vascular smooth muscle cells due to intimal damage are considered as major causes of intravascular pachymenia and restenosis caused thereby (Nature, Vol. 362, p. 801 (1993)). In recent years, drug-eluting stents coated with sirolimus or paclitaxel, which has an antiproliferative action against vascular smooth muscle cells, have been developed. Although it has been reported that both drug-eluting stents exhibited significant inhibitory effects on restenosis compared with conventional stents, restenosis is still observed in a little less than approximately 10% of patients (N. Engl. J. Med., Vol. 349, p. 1315 (2003); N. Engl. J. Med., Vol. 350, p. 221 (2004)).

The mitotic kinesins are proteins that are involved in the mitotic spindle regulation, and play an essential role for progression of the mitotic phase in cell cycle. The mitotic kinesin Eg5, one of the mitotic kinesins, is a bipolar homotetramer molecule, and is known to be involved in the formation of the bipolar spindle structure by crosslinking two of microtubules of the same direction and moving them in the direction toward the + (plus) end to cause sliding of two of the antiparallel microtubules, thereby keep − (minus) ends of microtubules at a distance and separate spindle pole bodies [Cell, Vol. 83, p. 1159 (1995); J. Cell Biol., Vol. 150, p. 975 (2000); Jikken Igaku (Experimental Medicine), Vol. 17, p. 439 (1999)]. Therefore, Eg5 inhibitors are considered promising as therapeutic agents of diseases relating to cell proliferation [WO2001/98278; WO2002/56880; WO2002/57244; Trends in Cell Biology, Vol. 12, p. 585 (2002)]. As Eg5 inhibitors, there are known, for example, quinazolin-4-one derivatives (WO2001/30768, WO2003/039460, and the like), triphenylmethane derivatives (WO2002/56880), thiadiazoline derivatives (refer to Patent documents 1 to 4), and the like.

There are further known thiadiazoline derivatives having an antitumor effect (see, Patent document 5).

[Patent document 1] International Patent Publication WO2004/092147
[Patent document 2] International Patent Publication WO2004/111023
[Patent document 3] International Patent Publication WO2004/111024
[Patent document 4] International Patent Publication WO2005/035512
[Patent document 5] International Patent Publication WO2003/051854

DISCLOSURE OF THE INVENTION

Object to be Solved by the Invention

An object of the present invention is to provide a therapeutic and/or prophylactic agent for restenosis comprising a thiadiazoline derivative or a pharmaceutically acceptable salt thereof as an active ingredient.

Means for Solving the Object

The present invention relates to the following (1) to (26).
(1) A therapeutic and/or prophylactic agent for restenosis, which comprises a thiadiazoline derivative represented by the general formula (0):

[Formula 1]

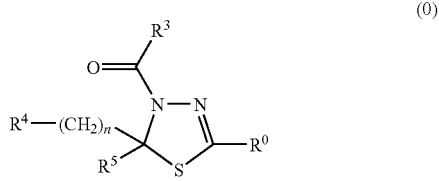

<wherein, n represents an integer of 1 to 3,
$R^0$ represents (i) aryl which may be substituted with one to three substituents selected from the group consisting of halogen, hydroxy, cyano and lower alkyl, or
(ii) $-NR^{COR2}$ (wherein $R^1$ represents a hydrogen atom, $R^2$ represents lower alkyl, or
$R^1$ and $R^2$ are combined together to represent alkylene),
$R^3$ represents lower alkyl,
$R^4$ represents (i) a hydrogen atom,
(ii) $NHR^6$ {wherein $R^6$ represents (a) lower alkyl which may be substituted with one or two substituents selected from the group consisting of hydroxy, lower alkoxy and $NR^{11}R^{12}$ (wherein $R^{11}$ and $R^{12}$ are the same or different, and each represents lower alkanoyl which may be substituted with one or two substituents selected from the group consisting of amino, (lower alkyl)amino and di-(lower alkyl)amino; cycloalkyl; lower alkyl; (lower alkoxy)carbonyl; lower alkoxy; hydroxy or a hydrogen atom); (b) $SO_2R^7$ [wherein $R^7$ represents (1) lower alkyl which may be substituted with one or two substituents selected from the group consisting of (α) (lower alkyl)thio which may be substituted with one or two substituents selected from the group consisting of hydroxy, amino, lower alkoxy, (lower alkyl)amino and di-(lower alkyl)amino; (β) a nitrogen-containing heterocyclic group which may be substituted with one to three substituents selected from the group consisting of lower alkyl which may be substituted with hydroxy, amino, (lower alkyl)amino, or di-(lower alkyl) amino, oxo, hydroxy, sulfanyl, amino, lower alkoxy, methylenedioxy, ethylenedioxy, (lower alkyl)thio, (lower alkyl) amino, di-(lower alkyl)amino, lower alkyl, aryl, formyl and lower alkanoyl; (γ) lower alkoxy; (δ) hydroxy, and (σ) $NR^{11}R^{12}$ (wherein $R^{11}$ and $R^{12}$ have the same meanings as those mentioned above, respectively), (2) amino, (3) (lower alkyl)amino, (4) di-(lower alkyl)amino, or (5) lower alkenyl]; (c) $COR^8$ [wherein $R^8$ represents (1) lower alkyl which may be substituted with one or two substituents selected from the group consisting of hydroxy, lower alkoxy, carboxy, phenyl, hydroxyphenyl, imidazolyl, guanidyl, methylthio and $NR^{11}R^{12}$ (wherein $R^{11}$ and $R^{12}$ have the same meanings as those mentioned above, respectively); (2) a nitrogen-containing aliphatic heterocyclic group which may be substituted with (lower alkoxy)carbonyl or oxo; or (3) lower alkoxy]; (d) cycloalkyl; or (e) a hydrogen atom}, or (iii) CONHR$^9$ [wherein R$^9$ represents lower alkyl which may be substituted with one or two substituents selected from the group consisting of hydroxy, lower alkoxy, carbamoyl, (lower alkyl)carbamoyl, di-(lower alkyl)carbamoyl and NR$^{11}$R$^{12}$ (wherein R$^{11}$ and R$^{12}$ have the same meanings as those mentioned above, respectively)], and R$^5$ represents aryl which may be substituted with one to three substituents selected from the group consisting of halogen, hydroxy, lower alkoxy, nitro, amino, cyano and carboxy>, or a pharmaceutically acceptable salt thereof.

(2) The therapeutic and/or prophylactic agent according to (1), wherein the thiadiazoline derivative is a thiadiazoline derivative represented by the following formula (00):

[Formula 2]

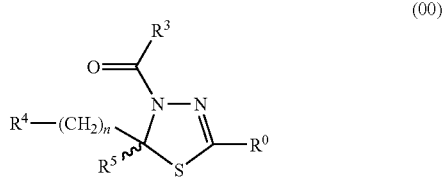

(00)

(wherein R$^0$, R$^3$, R$^4$, R$^5$, and n have the same meanings as those mentioned above, respectively), which shows a negative value as a specific rotation at 20° C. for sodium D line (wavelength: 589.3 nm) when the thiadiazoline derivative or the pharmaceutically acceptable salt thereof is dissolved in methanol.

(3) The therapeutic and/or prophylactic agent according to (1) or (2), wherein
R$^4$ is
(i) a hydrogen atom,
(ii) NHR$^{6A}$ {wherein R$^{6A}$ represents (a) lower alkyl which may be substituted with one or two substituents selected from the group consisting of hydroxy, lower alkoxy and NR$^{11A}$R$^{12A}$ (wherein R$^{11A}$ and R$^{12A}$ are the same or different, and each represents lower alkyl, (lower alkoxy)carbonyl, lower alkoxy, hydroxy, or a hydrogen atom); (b) SO$_2$R$^7$ (wherein R$^7$ has the same meaning as that mentioned above); (c) COR$^{8A}$ [wherein R$^{8A}$ represents (1) lower alkyl which may be substituted with one or two substituents selected from the group consisting of hydroxy, lower alkoxy, carboxy, phenyl, hydroxyphenyl, imidazolyl, guanidyl, methylthio and NR$^{11A}$R$^{12A}$ (wherein R$^{11A}$ and R$^{12A}$ have the same meanings as those mentioned above, respectively); (2) a nitrogen-containing aliphatic heterocyclic group which may be substituted with (lower alkoxy)carbonyl or oxo; or (3) lower alkoxy]; or (d) a hydrogen atom}, or
(iii) CONHR$^{9A}$ [wherein R$^{9A}$ represents lower alkyl which may be substituted with one or two substituents selected from the group consisting of hydroxy, lower alkoxy, carbamoyl, (lower alkyl)carbamoyl, di-(lower alkyl)carbamoyl and NR$^{11A}$R$^{12A}$ (wherein R$^{11A}$ and R$^{12A}$ have the same meanings as those mentioned above, respectively)].

(4) The therapeutic and/or prophylactic agent according to (1) or (2), wherein
R$^4$ is
(i) a hydrogen atom,
(ii) NHR$^{6B}$ {wherein R$^{6B}$ represents (a) lower alkyl which may be substituted with one or two substituents selected from the group consisting of hydroxy and NR$^{11B}$R$^{12B}$ (wherein R$^{11B}$ and R$^{12B}$ are the same or different, and each represents lower alkyl or a hydrogen atom); (b) SO$_2$R$^{7B}$ [wherein R$^{7B}$ represents (1) lower alkyl which may be substituted with one or two substituents selected from the group consisting of (α) (lower alkyl)thio which may be substituted with one or two substituents selected from the group consisting of hydroxy, amino, lower alkoxy, (lower alkyl)amino and di-(lower alkyl)amino; (β) a nitrogen-containing heterocyclic group which may be substituted with one to three substituents selected from the group consisting of lower alkyl which may be substituted with hydroxy, amino, (lower alkyl)amino, or di-(lower alkyl) amino, oxo, hydroxy, sulfanyl, amino, lower alkoxy, methylenedioxy, ethylenedioxy, (lower alkyl)thio, (lower alkyl) amino, di-(lower alkyl)amino, lower alkyl, aryl, formyl and lower alkanoyl; and (γ) NR$^{11BB}$R$^{12BB}$ (wherein R$^{11BB}$ and R$^{12BB}$ are the same or different, and each represents lower alkanoyl which may be substituted with one or two substituents selected from the group consisting of amino, (lower alkyl)amino and di-(lower alkyl)amino, cycloalkyl, lower alkyl, or a hydrogen atom), (2) amino, (3) (lower alkyl)amino, (4) di-(lower alkyl)amino, or (5) lower alkenyl]; (c) COR$^{8B}$ (wherein R$^{8B}$ represents a nitrogen-containing aliphatic heterocyclic group which may be substituted with (lower alkoxy)carbonyl or oxo); or (d) a hydrogen atom}, or
(iii) CONHR$^{9B}$ (wherein R$^{9B}$ represents lower alkyl which may be substituted with one or two substituents selected from the group consisting of hydroxy, lower alkoxy, carbamoyl, (lower alkyl)carbamoyl and di-(lower alkyl)carbamoyl).

(5) The therapeutic and/or prophylactic agent according to (1) or (2), wherein
R$^4$ is
(i) a hydrogen atom,
(ii) NHR$^{6C}$ {wherein R$^{6C}$ represents (a) lower alkyl which may be substituted with one or two substituents selected from the group consisting of hydroxy and NR$^{11B}$R$^{12B}$ (wherein R$^{11B}$ and R$^{12B}$ have the same meanings as those mentioned above, respectively);
(b) SO$_2$R$^{7C}$ [wherein R$^{7C}$ represents (1) lower alkyl which may be substituted with one or two substituents selected from the group consisting of (α) (lower alkyl)thio which may be substituted with one or two substituents selected from the group consisting of hydroxy and amino; (β) a nitrogen-containing heterocyclic group which may be substituted with one to three substituents selected from the group consisting of lower alkyl which may be substituted with hydroxy, oxo, hydroxy, sulfanyl, amino, (lower alkyl) thio and formyl; and (γ) NR$^{11C}$R$^{12C}$ (wherein R$^{11C}$ and R$^{12C}$ are the same or different, and each represents lower alkanoyl which may be substituted with amino, cycloalkyl, lower alkyl, or a hydrogen atom); (2) di-(lower alkyl) amino, or (3) lower alkenyl]; (c) COR$^{8C}$ (wherein R$^{8C}$ represents a nitrogen-containing aliphatic heterocyclic group); or (d) a hydrogen atom}, or
(iii) CONHR$^{9C}$ (wherein R$^{9C}$ represents lower alkyl which may be substituted with one or two substituents selected from the group consisting of hydroxy and carbamoyl).

(6) The therapeutic and/or prophylactic agent according to (1) or (2), wherein R$^4$ is NHR$^{6B}$ (wherein R$^{6B}$ has the same meaning as that mentioned above).

(7) The therapeutic and/or prophylactic agent according to (1) or (2), wherein R$^4$ is NHR$^{6C}$ (wherein R$^{6C}$ has the same meaning as that mentioned above).

(8) The therapeutic and/or prophylactic agent according to (1) or (2), wherein $R^4$ is $NHSO_2R^7$ (wherein $R^7$ has the same meaning as that mentioned above).

(9) The therapeutic and/or prophylactic agent according to (1) or (2), wherein $R^4$ is $NHSO_2R^{7B}$ (wherein $R^{7B}$ has the same meaning as that mentioned above).

(10) The therapeutic and/or prophylactic agent according to (1) or (2), wherein $R^4$ is $NHSO_2R^{7C}$ (wherein $R^{7C}$ has the same meaning as that mentioned above).

(11) The therapeutic and/or prophylactic agent according to (1) or (2), wherein $R^4$ is $CONHR^{9C}$ (wherein $R^{9C}$ has the same meaning as that mentioned above).

(12) The therapeutic and/or prophylactic agent according to (1) or (2), wherein $R^4$ is $NHR^{6D}$ [wherein $R^{6D}$ represents lower alkyl which may be substituted with one or two substituents selected from the group consisting of hydroxy and $NR^{11B}R^{12B}$ (wherein $R^{11B}$ and $R^{12B}$ have the same meanings as those mentioned above, respectively), or a hydrogen atom].

(13) The therapeutic and/or prophylactic agent according to any one of (1) to (12), wherein $R^5$ is phenyl.

(14) The therapeutic and/or prophylactic agent according to any one of (1) to (13), wherein $R^3$ is methyl, ethyl, isopropyl or tert-butyl.

(15) The therapeutic and/or prophylactic agent according to any one of (1) to (14), wherein $R^0$ is $-NR^1COR^2$ (wherein $R^1$ and $R^2$ have the same meanings as those mentioned above, respectively).

(16) The therapeutic and/or prophylactic agent according to (15), wherein $R^1$ is a hydrogen atom.

(17) The therapeutic and/or prophylactic agent according to (16), wherein $R^2$ is methyl or tert-butyl.

(18) The therapeutic and/or prophylactic agent according to (15), wherein $R^1$ and $R^2$ are combined together to represent trimethylene or tetramethylene.

(19) The therapeutic and/or prophylactic agent according to any one of (1) to (14), wherein $R^0$ is aryl which may be substituted with one to three substituents selected from the group consisting of halogen, hydroxy, lower alkyl and cyano.

(20) The therapeutic and/or prophylactic agent according to any one of (1) to (14), wherein $R^0$ is aryl which may be substituted with halogen.

(21) The therapeutic and/or prophylactic agent according to any one of (1) to (20), wherein n is 1 or 2.

(22) The therapeutic and/or prophylactic agent according to (2), wherein the thiadiazoline derivative is a thiadiazoline derivative represented by any one of the following formulas (a) to (r).

[Formula 3]

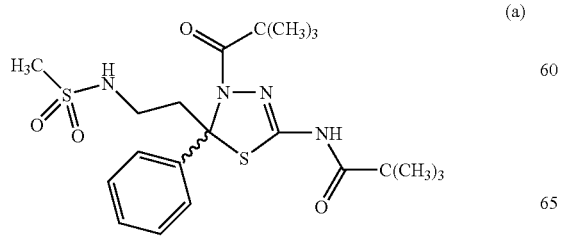

(a)

-continued

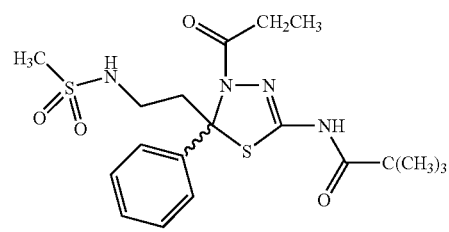

(b)

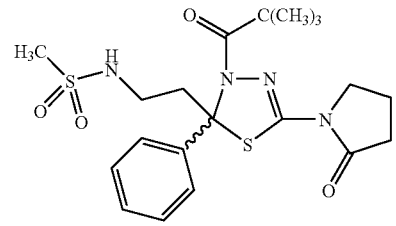

(c)

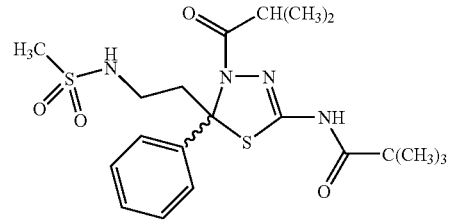

(d)

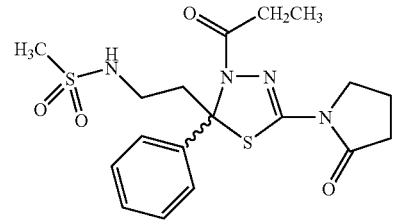

(e)

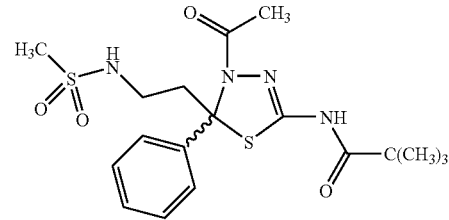

(f)

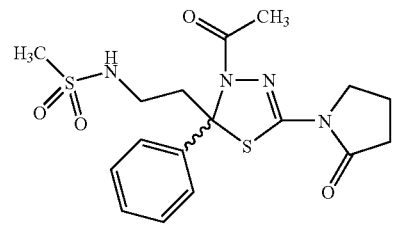

(g)

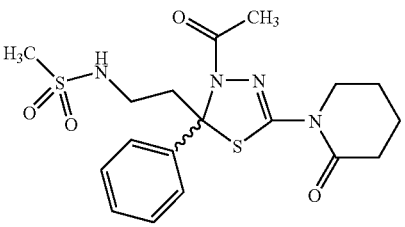

(h)

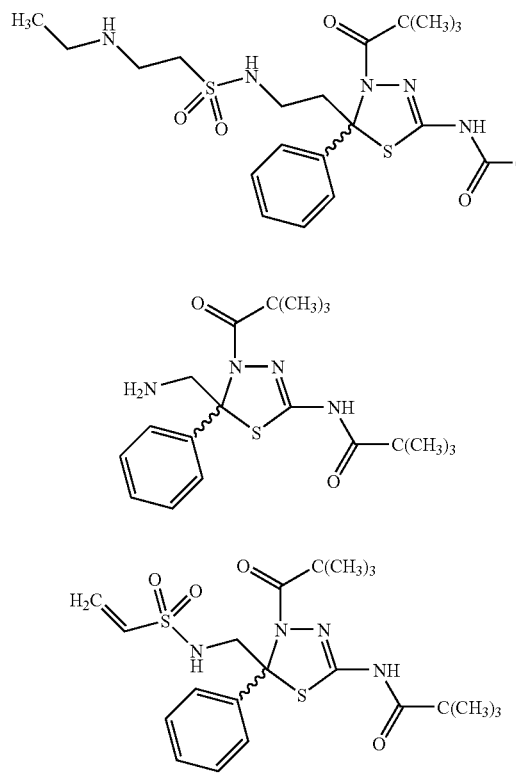
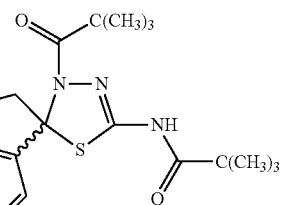
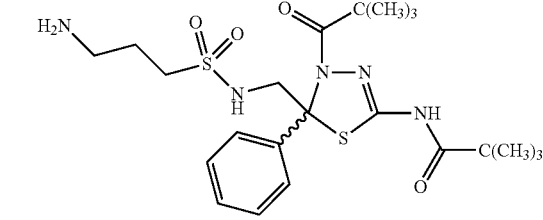
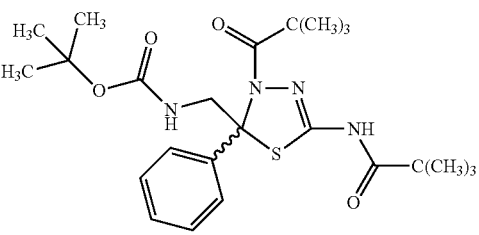
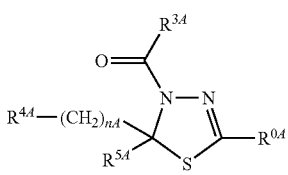
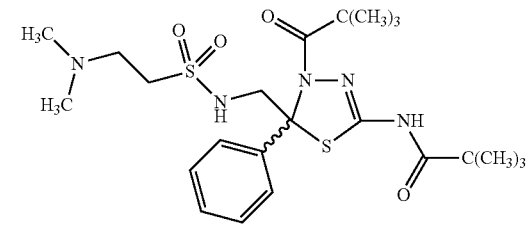
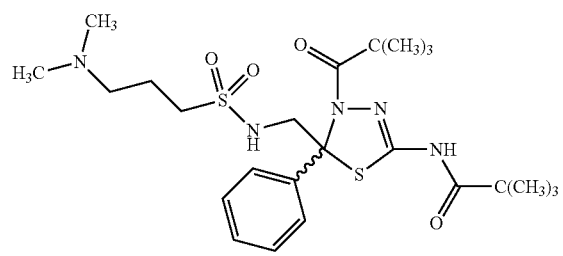

(23) A thiadiazoline derivative represented by the general formula (0A):

[Formula 4]

$$R^{4A}-(CH_2)_{nA} \begin{matrix} O \\ \parallel \\ C-R^{3A} \\ | \\ N-N \\ \diagdown \diagup \\ R^{5A} \quad S \end{matrix} R^{0A}$$ (0A)

<wherein nA, $R^{0A}$, $R^{3A}$ and $R^{5A}$ have the same meanings as those of n, $R^0$, $R^3$ and $R^5$ mentioned above, respectively, $R^{4A}$ represents $NHSO_2R^{7AA}$ [wherein $R^{7AA}$ represents lower alkyl substituted with a nitrogen-containing heterocyclic group which may be substituted with one to three substituents selected from the group consisting of lower alkyl which may be substituted with hydroxy, amino, (lower alkyl)amino, or di-(lower alkyl)amino, oxo, hydroxy, sulfanyl, amino, lower alkoxy, methylenedioxy, ethylenedioxy, (lower alkyl)thio, (lower alkyl)amino, di-(lower alkyl)amino, lower alkyl, aryl, formyl and lower alkanoyl (provided that when $R^{0A}$ is 2,2-dimethylpropanoylamino, $R^{3A}$ is methyl, and nA is 1, $R^{7AA}$ is not morpholinoethyl)]>, or a pharmaceutically acceptable salt thereof.

(24) A method for therapeutic and/or prophylactic treatment of restenosis, which comprises administering an effective amount of the thiadiazoline derivative or the pharmaceutically acceptable salt thereof described in any one of (1) to (23).

(25) Use of the thiadiazoline derivative or the pharmaceutically acceptable salt thereof described in any one of (1) to (23) for the manufacture of a therapeutic and/or prophylactic agent for restenosis.

(26) A therapeutic and/or prophylactic agent for restenosis, which comprises a compound represented by the general formula (IV):

[Formula 5]

(IV)

or a pharmaceutically acceptable salt thereof.

Effect of the Invention

According to the present invention, a therapeutic and/or prophylactic agent for restenosis comprising a thiadiazoline derivative or a pharmaceutically acceptable salt thereof as an active ingredient can be provided.

BEST MODE FOR CARRYING OUT THE INVENTION

Hereinafter, compounds represented by the general formula (0) and compounds represented by the general formula (00) are referred to as "Compound (0)" and "Compound (00)", respectively. The compounds having the other formula numbers are referred to in the same manner.

In the definition of each group of the general formulas (0) and (00):

(i) Examples of the lower alkyl and the lower alkyl moiety in the lower alkoxy, the lower alkanoyl, the (lower alkyl)thio, the (lower alkyl)amino, the di-(lower alkyl)amino, the (lower alkyl)carbamoyl, the di-(lower alkyl)carbamoyl, and the (lower alkoxy)carbonyl include straight or branched alkyl having 1 to 10 carbon atoms, for example, methyl, ethyl, propyl, isopropyl, n-butyl, isobutyl, sec-butyl, tert-butyl, pentyl, isopentyl, neopentyl, hexyl, heptyl, octyl, nonyl, decyl and the like. The two lower alkyl moieties in the di-(lower alkyl)amino and the di-(lower alkyl)carbamoyl may be the same or different.

(ii) Examples of the lower alkenyl include straight or branched alkenyl having 2 to 10 carbon atoms, for example, vinyl, allyl, 1-propenyl, butenyl, pentenyl, hexenyl, heptenyl, octenyl, nonenyl, decenyl and the like.

(iii) Examples of the aryl include aryl having 6 to 14 carbon atoms, for example, phenyl, naphthyl and the like.

(iv) Examples of the alkylene include straight or branched alkylene having 1 to 10 carbon atoms, for example, methylene, ethylene, trimethylene, tetramethylene, pentamethylene, hexamethylene, heptamethylene, octamethylene, nonamethylene, decamethylene, propylene, ethylethylene, methylmethylene, dimethylmethylene and the like.

(v) Examples of the cycloalkyl include cycloalkyl having 3 to 8 carbon atoms, for example, cyclopropyl, cyclobutyl, cyclopentyl, cyclohexyl, cycloheptyl, cyclooctyl and the like.

(vi) Examples of the nitrogen-containing aliphatic heterocyclic group include a 5- or 6-membered monocyclic aliphatic heterocyclic group containing at least one nitrogen atom, a bicyclic or tricyclic condensed aliphatic heterocyclic group comprising 3- to 8-membered rings and containing at least one nitrogen atom and the like, for example, aziridinyl, azetidinyl, pyrrolidinyl, piperidino, piperidinyl, perhydroazepinyl, perhydroazocinyl, imidazolidinyl, pyrazolidinyl, piperazinyl, morpholino, morpholinyl, thiomorpholino, thiomorpholinyl, homopiperazinyl, tetrahydroquinolinyl, tetrahydroisoquinolinyl, dihydroindolinyl, dihydroisoindolinyl, oxazolidinyl, dihydropyrrolyl and the like.

(vii) Examples of the nitrogen-containing heterocyclic group include, besides the aforementioned nitrogen-containing aliphatic heterocyclic groups, for example, a 5- or 6-membered monocyclic aromatic heterocyclic group containing at least one nitrogen atom, a bicyclic or tricyclic condensed aromatic heterocyclic group comprising 3- to 8-membered rings and containing at least one nitrogen atom, and the like, for example, aziridinyl, azetidinyl, pyrrolidinyl, piperidino, piperidinyl, perhydroazepinyl, perhydroazocinyl, imidazolidinyl, pyrazolidinyl, piperazinyl, morpholino, morpholinyl, thiomorpholino, thiomorpholinyl, homopiperazinyl, tetrahydroquinolinyl, tetrahydroisoquinolinyl, dihydroindolinyl, dihydroisoindolinyl, oxazolidinyl, dihydropyrrolyl, pyrrolyl, imidazolyl, pyrazolyl, oxazolyl, isoxazolyl, oxadiazolyl, thiazolyl, isothiazolyl, thiadiazolyl, triazolyl, tetrazolyl, pyridyl, pyridazinyl, pyrimidinyl, pyrazinyl, triazinyl, benzoxazolyl, benzothiazolyl, isoindolyl, indolyl, indazolyl, benzimidazolyl, benzotriazolyl, oxazolopyrimidinyl, thiazolopyrimidinyl, pyrrolopyridinyl, pyrrolopyrimidinyl, imidazopyridinyl, purinyl, quinolinyl, isoquinolinyl, cinnolinyl, phthalazinyl, quinazolinyl, quinoxalinyl, naphthylidinyl, and the like. Among them, a 5- or 6-membered monocyclic nitrogen-containing aliphatic heterocyclic group and a 5- or 6-membered monocyclic nitrogen-containing aromatic heterocyclic group are preferred, and a 5-membered monocyclic nitrogen-containing aliphatic heterocyclic group and a 5-membered monocyclic nitrogen-containing aromatic heterocyclic group are more preferred (viii) Halogen means each atom of fluorine, chlorine, bromine, and iodine.

In each group of Compounds (0) and (00):

Preferred examples of $R^0$ include phenyl, tolyl, fluorophenyl, chlorophenyl, bromophenyl, cyanophenyl, difluorophenyl, $-NR^1COR^2$ (wherein $R^1$ and $R^2$ have the same meanings as those mentioned above, respectively) and the like, and more preferred examples include fluorophenyl, $-NR^1COR^2$ (wherein $R^1$ and $R^2$ have the same meanings as those mentioned above, respectively) and the like. In $-NR^1COR^2$ (wherein $R^1$ and $R^2$ have the same meanings as those mentioned above, respectively) mentioned above:

As $R^1$, a hydrogen atom is preferred.

As $R^2$, methyl, ethyl, propyl, isopropyl, n-butyl, sec-butyl, tert-butyl and the like are preferred, and methyl, tert-butyl and the like are more preferred.

As the alkylene formed by $R^1$ and $R^2$ combined together, trimethylene, tetramethylene, pentamethylene and the like are preferred.

Preferred examples of $R^3$ include methyl, ethyl, propyl, isopropyl, n-butyl, sec-butyl, tert-butyl and the like, and more preferred examples include methyl, ethyl, isopropyl, tert-butyl and the like.

Preferred examples of $R^4$ include a hydrogen atom, $NHR^{6A}$ (wherein $R^{6A}$ has the same meaning as that mentioned above), $CONHR^{9A}$ (wherein $R^{9A}$ has the same meaning as that mentioned above) and the like, more preferred examples include a hydrogen atom, $NHR^{6B}$ (wherein $R^{6B}$ has the same meaning as that mentioned above), $CONHR^{9B}$ (wherein $R^{9B}$ has the same meaning as that mentioned above) and the like, and still more preferred examples include a hydrogen atom, $NHR^{6C}$ (wherein $R^{6C}$ has the same meaning as that mentioned above), $CONHR^{9C}$ (wherein $R^{9C}$ has the same meaning as that mentioned above) and the like. Further, $NHR^{6B}$ (wherein $R^{6B}$ has the same meaning as that mentioned above) and the like are also preferred, $NHR^{6C}$ (wherein $R^{6C}$ has the same meaning as that mentioned above) and the like are also more preferred, and $NHR^{6D}$ (wherein $R^{6D}$ has the same meaning as that mentioned above) and the like are also still more preferred. Further, $NHSO_2R^7$ (wherein $R^7$ has the same meaning as that mentioned above) and the like are preferred, $NHSO_2R^{7B}$ (wherein $R^{7B}$ has the same meaning as that mentioned above) and the like are more preferred, and $NHSO_2R^{7C}$ (wherein $R^{7C}$ has the same meaning as that mentioned above) and the like are still more preferred. More preferred examples of $R^4$ include, for example, $NHSO_2R^{7X}$ [wherein $R^{7X}$ represents methyl, ethyl, propyl, vinyl, aminomethyl, 1-aminoethyl, 2-aminoethyl, 1-aminopropyl, 2-aminopropyl, 3-aminopropyl, methylaminomethyl, 1-(methylamino)ethyl, 2-(methylamino)ethyl, 1-(methylamino)propyl, 2-(methylamino)propyl, 3-(methylamino)propyl, dimethylaminomethyl, 1-(dimethylamino)ethyl, 2-(dimethylamino)ethyl, 1-(dimethylamino)propyl, 2-(dimethylamino)propyl, 3-(dimethylamino)propyl, ethylaminomethyl, 1-(ethylamino)ethyl, 2-(ethylamino)ethyl, 1-(ethylamino)propyl, 2-(ethylamino)propyl, 3-(ethylamino)propyl, diethylaminomethyl, 1-(diethylamino)ethyl, 2-(diethylamino)ethyl, 1-(diethylamino)propyl, 2-(diethylamino)propyl, 3-(diethylamino)propyl, propylaminomethyl, 2-(propylamino)ethyl, 3-(propylamino)propyl, isopropylaminomethyl, 2-(isopropylamino)ethyl, 3-(isopropylamino)propyl, aminomethylthiomethyl, 2-aminoethylthiomethyl, methylaminomethylthiomethyl, 2-dimethylaminoethylthiomethyl, 2-aminomethylthioethyl, 2-(2-aminoethylthio)ethyl, 2-(methylaminomethylthio)ethyl, 2-(2-methylaminoethylthio)ethyl, 2-(dimethylaminomethylthio)ethyl, 2-(2-dimethylaminoethylthio)ethyl, 3-aminomethylthiopropyl, 3-(2-aminoethylthio)propyl, cyclopropylaminomethyl, 2-cyclopropylaminoethyl, 3-cyclopropylaminopropyl, 2-cyclobutylaminoethyl, 2-cyclopentylaminoethyl, 2-cyclohexylaminoethyl, 2-(N-cyclopropyl-N-methylamino)methyl, 2-(N-cyclopropyl-N-ethylaminomethyl)methyl, 2-(N-cyclopropyl-N-methylamino)ethyl, 2-(N-cyclopropyl-N-ethylaminomethyl)ethyl, 2-(2-oxooxazolidinyl)ethyl; 2-pyrazolylethyl, 2-(3-aminopyrazolyl)ethyl, 2-triazolylethyl, 2-imidazolylethyl, 2-(2-methylimidazolyl)ethyl, 2-(2-hydroxymethylimidazolyl)ethyl, 2-(2-isopropylimidazolyl)ethyl, 2-(2-sulfanylimidazolyl)ethyl, 2-(2-methylthioimidazolyl)ethyl, 2-(2-aminoimidazolyl)ethyl, 2-(2-formylimidazolyl)ethyl, 2-pyrrolidinylethyl, 2-(3-hydroxypyrrolidinyl)ethyl, 2-(dihydropyrrolyl)ethyl, 2-(2-oxoimidazolidinyl)ethyl, 2-piperazinylethyl, 2-(2-oxopiperazinyl)ethyl, 2-aminoethylthiomethyl, 2-(2-aminoethylthio)ethyl, 2-hydroxyethylthiomethyl, 2-(2-hydroxyethylthio)ethyl, dimethylamino, diethylamino or the like], $NHR^{6X}$ [wherein $R^{6X}$ represents a hydrogen atom, methyl, ethyl, propyl, isopropyl, n-butyl, aminomethyl, 1-aminoethyl, 2-aminoethyl, 1-aminopropyl, 2-aminopropyl, 3-aminopropyl, methylaminomethyl, 1-(methylamino)ethyl, 2-(methylamino)ethyl, 1-(methylamino)propyl, 2-(methylamino)propyl, 3-(methylamino)propyl, dimethylaminomethyl, 1-(dimethylamino)ethyl, 2-(dimethylamino)ethyl, 1-(dimethylamino)propyl, 2-(dimethylamino)propyl, 3-(dimethylamino)propyl, ethylaminomethyl, 1-(ethylamino)ethyl, 2-(ethylamino)ethyl, 3-(ethylamino)propyl, diethylaminomethyl, 1-(diethylamino)ethyl, 2-(diethylamino)ethyl, 3-(diethylamino)propyl, propylaminomethyl, 2-(propylamino)ethyl, 3-(propylamino)propyl, isopropylaminomethyl, 2-(isopropylamino)ethyl, 3-(isopropylamino)propyl, hydroxymethyl, 2-hydroxyethyl, 3-hydroxypropyl or the like], $NHCOR^{8X}$ (wherein $R^{8X}$ represents methyl, ethyl, propyl, n-butyl, sec-butyl, tert-butyl, n-pentyl, aminomethyl, methylaminomethyl, dimethylaminomethyl, aminoethyl, methylaminoethyl, dimethylaminoethyl, aminopropyl, methylaminopropyl, dimethylaminopropyl, pyrrolidinyl, 2-oxopyrrolidinyl, methoxy, ethoxy, n-butoxy, sec-butoxy, tert-butoxy or the like), $CONHR^{9X}$ [wherein $R^{9X}$ represents methyl, ethyl, propyl, isopropyl, n-butyl, 2-hydroxyethyl, 2-hydroxypropyl, 3-hydroxypropyl, 2-hydroxy-n-butyl, 3-hydroxy-n-butyl, 4-hydroxy-n-butyl, 2-hydroxy-1-(hydroxymethyl)ethyl, 2-hydroxy-1-methylethyl, aminomethyl, 1-aminoethyl, 2-aminoethyl, 1-aminopropyl, 2-aminopropyl, 3-aminopropyl, methylaminomethyl, 1-(methylamino)ethyl, 2-(methylamino)ethyl, 1-(methylamino)propyl, 2-(methylamino)propyl, 3-(methylamino)propyl, dimethylaminomethyl, 1-(dimethylamino)ethyl, 2-(dimethylamino)ethyl, 1-(dimethylamino)propyl, 2-(dimethylamino)propyl, 3-(dimethylamino)propyl, ethylaminomethyl, 1-(ethylamino)ethyl, 2-(ethylamino)ethyl, 3-(ethylamino)propyl, diethylaminomethyl, 1-(diethylamino)ethyl, 2-(diethylamino)ethyl, 3-(diethylamino)propyl, propylaminomethyl, 2-(propylamino)ethyl, 3-(propylamino)propyl, isopropylaminomethyl, 2-(isopropylamino)ethyl, 3-(isopropylamino)propyl, carbamoylmethyl, 2-carbamoylethyl or the like] and the like.

Preferred examples of $R^5$ include phenyl and the like.

n is preferably 1 or 2.

As Compounds (0) and (00), preferred are those having a combination of substituents selected from the preferred substituents mentioned above per group. For example, when $R^0$ is —$NR^1COR^2$ (wherein $R^1$ and $R^2$ have the same meanings as those mentioned above, respectively), preferred are those compounds wherein $R^1$ is a hydrogen atom, $R^2$ is methyl, ethyl, propyl, isopropyl, n-butyl, sec-butyl, tert-butyl or the like, or $R^1$ and $R^2$ are combined together to represent trimethylene, tetramethylene, pentamethylene or the like, $R^3$ is methyl, ethyl, propyl, isopropyl, n-butyl, sec-butyl, tert-butyl or the like, $R^4$ is $NHR^{6A}$ (wherein $R^{6A}$ has the same meaning as that mentioned above), $CONHR^{9A}$ (wherein $R^{9A}$ has the same meaning as that mentioned above) or the like, and $R^5$ is phenyl, more preferred are those compounds wherein $R^1$ is a hydrogen atom, $R^2$ is methyl, tert-butyl or the like, or $R^1$ and $R^2$ are combined together to represent trimethylene, tetramethylene or the like, $R^3$ is methyl, ethyl, isopropyl, tert-butyl or the like, $R^4$ is $NHR^{6C}$ (wherein $R^{6C}$ has the same meaning as that mentioned above), $CONHR^{9C}$ (wherein $R^{9C}$ has the same meaning as that mentioned above) or the like, and $R^5$ is phenyl, still more preferred are those compounds wherein $R^1$ is a hydrogen atom, $R^2$ is tert-butyl or the like, or $R^1$ and $R^2$ are combined together to represent trimethylene, tetramethylene or the like, $R^3$ is methyl, ethyl, isopropyl, tert-butyl or the like, $R^4$ is $NHSO_2R^7$ (wherein $R^7$ has the same meaning as that mentioned above) or the like, and $R^5$ is phenyl, and further preferred are those compounds wherein $R^1$ is a hydrogen atom, $R^2$ is tert-butyl or the like, or $R^1$ and $R^2$ are combined together to represent trimethylene, tetramethylene or the like, $R^3$ is methyl, ethyl, isopropyl, tert-butyl or the like, $R^4$ is $NHSO_2R^{7C}$ (wherein $R^{7C}$ has the same meaning as that mentioned above) or the like, and $R^5$ is phenyl.

Further, when $R^0$ is aryl which may be substituted with one to three substituents selected from the group consisting of halogen, hydroxy, cyano and lower alkyl, preferred are those compounds wherein $R^3$ is methyl, ethyl, isopropyl, tert-butyl or the like, $R^4$ is $NHSO_2R^7$ (wherein $R^7$ has the same meaning as that mentioned above) or the like, and $R^5$ is phenyl, and more preferred are those compounds wherein $R^3$ is methyl, ethyl, isopropyl, tert-butyl or the like, $R^4$ is $NHSO_2R^{7C}$ (wherein $R^{7C}$ has the same meaning as that mentioned above) or the like, and $R^5$ is phenyl Further, as Compound (0), preferred are those compounds showing a negative value as a specific rotation at 20° C. for sodium D line (wavelength: 589.3 nm) when they are dissolved in methanol.

Furthermore, in Compounds (0) and (00), the asymmetric center to which $R^5$ binds is preferably in the R-configuration when n is 1, or the asymmetric center to which $R^5$ binds is preferably in the S-configuration when n is 2 or 3. Namely, Compounds (0) and (00) are preferably compounds having the steric configuration represented by the following formula (Z).

[Formula 6]

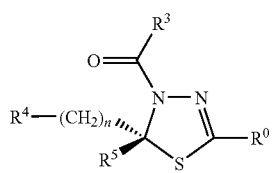

(Z)

Examples of the pharmaceutically acceptable salt of Compound (0) include pharmaceutically acceptable acid addition salts, metal salts, ammonium salts, organic amine addition salts, amino acid addition salts and the like. Examples of the pharmaceutically acceptable acid addition salt of Compound (0) include an inorganic acid salt such as hydrochloride, sulfate and phosphate, an organic acid salt such as acetate, maleate, fumarate and citrate, and the like. Examples of the pharmaceutically acceptable metal salt include an alkali metal salt such as a sodium salt and a potassium salt, an alkaline-earth metal salt such as a magnesium salt and a calcium salt, an aluminium salt, a zinc salt and the like. Examples of the pharmaceutically acceptable ammonium salt include a salt of ammonium, tetramethylammonium or the like. Examples of the pharmaceutically acceptable organic amine addition salt include an addition salt of morpholine, piperidine or the like. Examples of the pharmaceutically acceptable amino acid addition salt include an addition salt of lysine, glycine, phenylalanine, aspartic acid, glutamic acid or the like.

In addition to the pharmaceutically acceptable salt mentioned above, examples of salts of Compound (0) include a trifluoroacetate, a trifluoromethanesulfonate and the like.

Next, the methods of preparing the Compounds (0) and (00) are described as follows.

Among Compounds (0) and (00), Compounds (I) and (II) wherein $R^0$ is $—NR^1COR^2$ (wherein $R^1$ and $R^2$ have the same meanings as those mentioned above, respectively) can be prepared by the following methods.

Preparing Method 1

Compound (I) can be prepared by the methods described in WO2003/051854, WO2004/092147, WO2004/111024 and the like.

Preparing Method 2

Compound (II) can be prepared by subjecting Racemate (Ia) which can be obtained by the methods described in WO2003/051854, WO2004/092147, WO2004/111024 and the like to preparative high performance liquid chromatography using, for example, a column for optical isomer separation [for example, CHIRALPAK AD (Daicel Chemical Industries, Ltd.)] to separate each optical isomer.

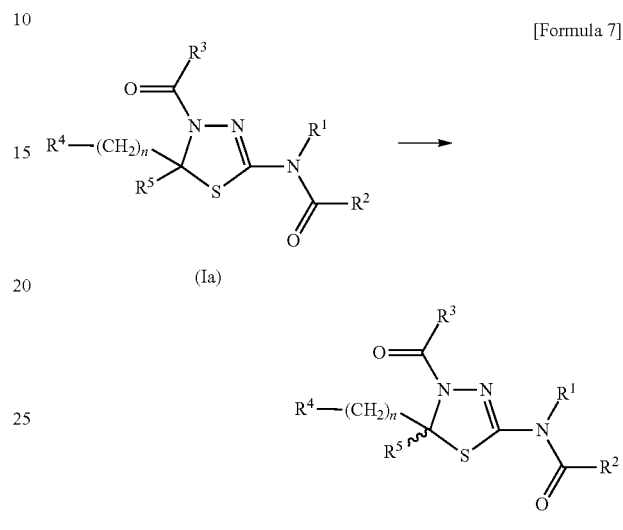

[Formula 7]

(wherein $R^1$, $R^2$, $R^3$, $R^4$, $R^5$, and n have the same meanings as those mentioned above, respectively)

Preparing Method 3

Compound (II) can also be prepared in accordance with the following steps.

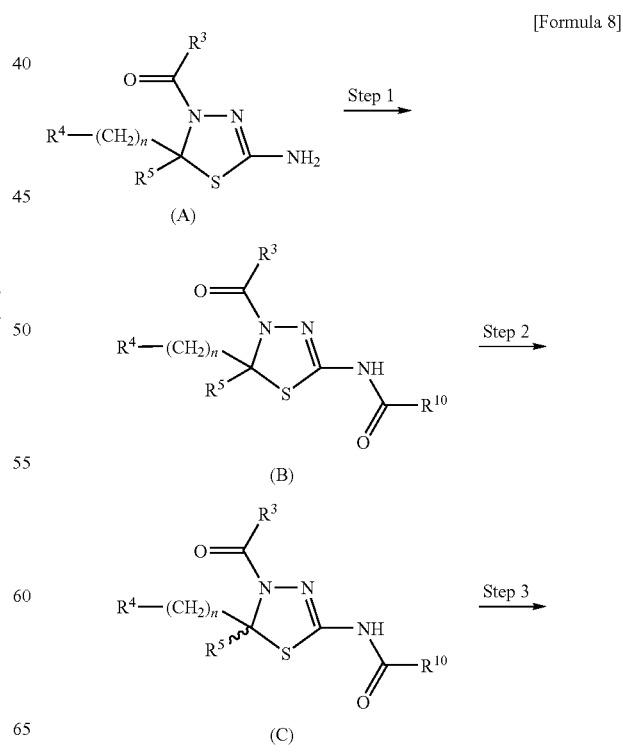

[Formula 8]

-continued

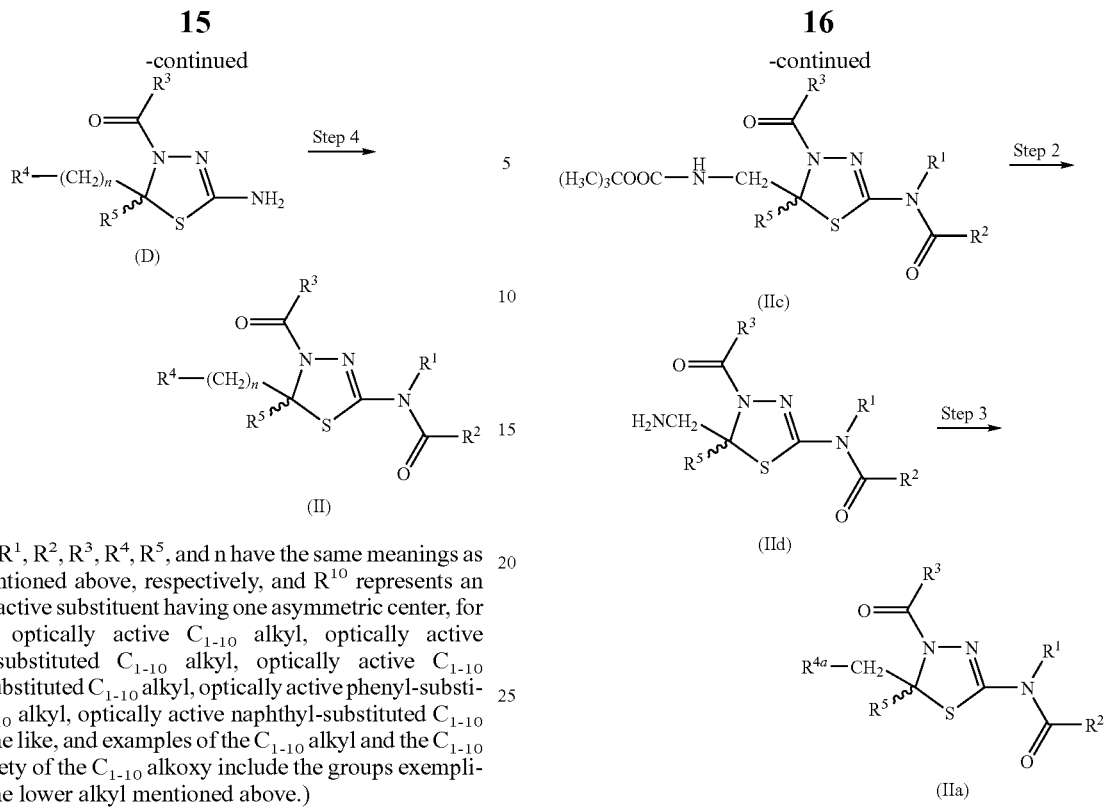

(wherein $R^1$, $R^2$, $R^3$, $R^4$, $R^5$, and n have the same meanings as those mentioned above, respectively, and $R^{10}$ represents an optically active substituent having one asymmetric center, for example, optically active $C_{1-10}$ alkyl, optically active hydroxy-substituted $C_{1-10}$ alkyl, optically active $C_{1-10}$ alkoxy-substituted $C_{1-10}$ alkyl, optically active phenyl-substituted $C_{1-10}$ alkyl, optically active naphthyl-substituted $C_{1-10}$ alkyl or the like, and examples of the $C_{1-10}$ alkyl and the $C_{1-10}$ alkyl moiety of the $C_{1-10}$ alkoxy include the groups exemplified for the lower alkyl mentioned above.)

The compound (A; racemate) obtained by the methods described in WO2003/051854, WO2004/092147, WO2004/111024 or the like is reacted with an optically active acylating agent [$R^{10}$COX (wherein $R^{10}$ has the same meaning as that mentioned above, and X represents chlorine atom, bromine atom, iodine atom or the like); ($R^{10}$CO)$_2$O (wherein $R^{10}$ has the same meaning as that mentioned above), or the like, for example, (R)-(−)-2-phenylpropionyl chloride, (S)-(+)-2-phenylpropionyl chloride and the like] according to, for example, the method described in Shin-Jikken-Kagaku-Koza Vol. 14, p. 1142 (Maruzen, 1978) or the like to obtain a compound (B; mixture of diastereomers) (Step 1). Next, the diastereomers of Compound (B) obtained are separated by silica gel column chromatography, recrystallization, or other means to obtain a compound (C; one diastereomer) (Step 2). Then, Compound (C) obtained is treated with a reducing agent such as sodium borohydride, or the like according to, for example, the method described in WO2003/051854 or the like and thereby converted into Compound (D) (Step 3), and finally, Compound (D) can be, for example, acylated according to, for example, the method described in WO2003/051854 or the like to obtain Compound (II) (Step 4).

Preparing Method 4

Among Compound (II), Compounds (IIc), (IId) and (IIa) wherein n is 1, and $R^4$ is NHCOOC(CH$_3$)$_3$, NH$_2$ or NHR$^6$ (wherein $R^6$ has the same meaning as that mentioned above) can also be prepared in accordance with the following steps.

[Formula 9]

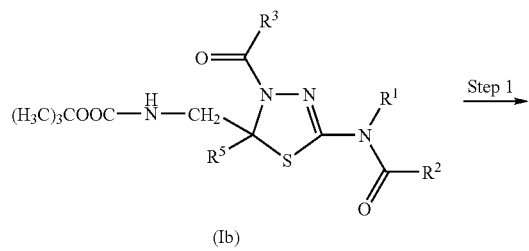

(wherein $R^{4a}$ represents (a) lower alkyl which may be substituted with one or two substituents selected from the group consisting of hydroxy, lower alkoxy and NR$^{11}$R$^{12}$ (wherein R$^{11}$ and R$^{12}$ have the same meaning as those mentioned above); (b) SO$_2$R$^7$ (wherein R$^7$ has the same meaning as that mentioned above); (c)COR$^8$ (wherein R$^8$ has the same meaning as that mentioned above), or (d) cycloalkyl, and $R^1$, $R^2$, $R^3$ and $R^5$ have the same meanings as those mentioned above, respectively, among the groups defined for $R^6$).

The compound (Ib; racemate) obtained by the method described in WO2003/051854, WO2004/092147, WO2004/111024 or the like is subjected to preparative high performance liquid chromatography using a column for optical isomer separation [for example, CHIRALPAK AD (Daicel Chemical Industries, Ltd.)] to obtain a compound (IIc; one enantiomer) (Step 1). Next, Compound (IIc) obtained is treated with an acid such as hydrochloric acid and trifluoroacetic acid according to, for example, the method described in WO2004/111024 or the like to obtain Compound (IId) (Step 2). Then, sulfonylation, acylation, alkylation and the like of Compound (IId) can be performed according to, for example, the method described in WO2004/111024 or the like to prepare Compound (IIa) (Step 3).

Preparing Method 5

Among Compound (I), Compound (IA) wherein R$^1$ is a hydrogen atom, R$^2$ and R$^3$, which are the same, represent lower alkyl, and R$^4$ is tert-butoxycarbonylamino can also be prepared in accordance with the following steps.

[Formula 10]

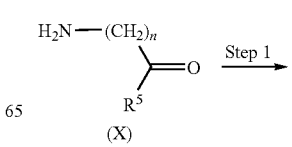

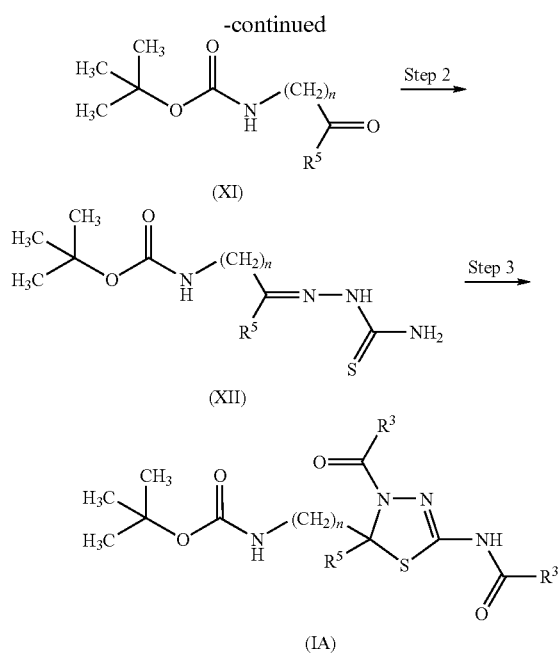

(wherein n, $R^1$, $R^3$ and $R^5$ have the same meaning as those mentioned above, respectively)

Step 1

Compound (XI) can be prepared by the reaction of Compound (X) with di-tert-butyl dicarbonate in a suitable solvent in the presence of a base.

Specifically, for example, Compound (XI) can be prepared by dissolving Compound (X) in a suitable solvent, adding di-tert-butyl dicarbonate and then a base, and allowing them to react at a temperature preferably between 0° C. and 80° C., more preferably between 0° C. and 40° C., for 5 minutes to 72 hours, preferably 30 minutes to 4 hours.

Di-tert-butyl dicarbonate is preferably used in an amount of 1 to 10 equivalents, more preferably 1 to 3 equivalents, still more preferably 1 to 1.2 equivalents, to Compound (X).

Examples of the solvent include, for example, hydrophilic solvents such as methanol, ethanol, acetonitrile, dioxane, N,N-dimethylformamide (DMF), N,N-dimethylacetamide (DMA), N-methylpyrrolidone (NMP) and pyridine, non-hydrophilic organic solvents such as dichloromethane, chloroform, 1,2-dichloroethane, toluene, methyl acetate, ethyl acetate, propyl acetate, isopropyl acetate, butyl acetate, diethyl ether, tetrahydrofuran (THF), and 1,2-dimethoxyethane (DME), water and the like, and they can be used alone or as a mixture. Preferred examples include non-hydrophilic organic solvents, or mixed solvents of a non-hydrophilic organic solvent and water, more preferred examples include organic solvents such as methyl acetate, ethyl acetate, propyl acetate, isopropyl acetate and butyl acetate, and mixed solvents of these organic solvents and water, and still more preferred examples include mixed solvents of ethyl acetate and water (2:1 to 1:2, preferably 4:3 to 3:4, more preferably 5:4 to 1:1, still more preferably 1:1). Further, the total amount of the solvent used is, for example, such an amount that the concentration of Compound (X) should become 10 to 600 g/L, preferably 20 to 200 g/L, more preferably 30 to 80 g/L.

Examples of the base include, for example, sodium hydrogencarbonate, potassium hydrogencarbonate, sodium carbonate, potassium carbonate, potassium hydroxide, sodium hydroxide, lithium hydroxide, sodium methoxide, potassium tert-butoxide, triethylamine, diisopropylethylamine, N-methylmorpholine, pyridine, 1,8-diazabicyclo[5.4.0]-7-undecene (DBU) and the like, preferred examples include sodium hydrogencarbonate, potassium hydrogencarbonate, sodium carbonate, potassium carbonate, potassium hydroxide, sodium hydroxide and the like, and more preferred examples include sodium hydrogencarbonate, potassium carbonate and the like. The base is preferably used in a large excess amount, more preferably in an amount of 1 to 30 equivalents, still more preferably 1 to 5 equivalents, further preferably 1 to 1.2 equivalents, to Compound (X). The base is preferably dissolved in a suitable volume of water, and slowly added as an aqueous solution at a concentration of, for example, 1 to 6 mol/L, preferably 1.5 to 2.5 mol/L, to a solution dissolving Compound (X) and di-tert-butyl dicarbonate with vigorous stirring at a temperature preferably between 0° C. and 40° C., more preferably between 0° C. and 10° C.

Compound (X) can be obtained as a commercial product, or according to the methods described in, for example, J. Med. Chem., Vol. 25, p. 1045 (1982); Synthesis, Vol. 28, p. 615 (1990) and the like.

Step 2

Compound (XII) can be prepared by the reaction of Compound (XI) obtained in Step 1 mentioned above with thiosemicarbazide in a suitable solvent.

Specifically, Compound (XII) can be prepared by dissolving Compound (XI) obtained in Step 1 mentioned above in a suitable solvent, adding dropwise a solution of thiosemicarbazide in aqueous hydrochloric acid preferably at a temperature between –10° C. and 60° C., more preferably between 0° C. and 20° C., stirring the mixture preferably at room temperature, for 5 minutes to 72 hours, preferably 30 minutes to 4 hours, and then for 30 minutes to 24 hours, preferably 30 minutes to 4 hours, under ice cooling, collecting deposited solid, washing and drying the resulting solid.

Examples of the solvent include, for example, hydrophilic solvents such as methanol, ethanol, propanol, 2-propanol, butanol, sec-butanol, tert-butanol, acetonitrile, dioxane, DMF, DMA, NMP and pyridine, non-hydrophilic solvents such as dichloromethane, chloroform, 1,2-dichloroethane, toluene, ethyl acetate, diethyl ether, THF and DME, water and the like, and they are used alone or as a mixture. Preferred examples include hydrophilic solvents or mixed solvents of a hydrophilic solvent and water, more preferred examples include methanol, ethanol, propanol, 2-propanol, butanol, sec-butanol, tert-butanol, mixed solvents of these and water and the like, and still more preferred examples include methanol, ethanol, mixed solvents of these and water and the like. A mixed solvent with water is most preferred, and a mixed solvent of methanol or ethanol and water (for example, 9:1 to 1:9, preferably 8:2 to 5:5, more preferably 7:3 to 6:4 (methanol or ethanol:water)) is especially preferred. The amount of the solvent used is, for example, such an amount that the concentration of Compound (XI) should become 50 to 600 g/L, preferably 80 to 300 g/L, more preferably 100 to 200 g/L.

Thiosemicarbazide is preferably used in an amount of 1 to 5 equivalents, more preferably 1 to 3 equivalents, still more preferably 1.1 to 2.2 equivalents. Moreover, thiosemicarbazide is preferably used as an aqueous solution acidified with hydrochloric acid, and for example, it is dissolved in, for example, 0.5 to 12 mol/L, preferably 0.5 to 6 mol/L, more preferably 2 to 3 mol/L of hydrochloric acid at a concentration of, for example, 100 g to 1 kg/L, preferably 150 to 300 g/L, more preferably 190 to 230 g/L, and used.

Furthermore, more preferably, by adding separately prepared crystals of Compound (XII), if needed, when 20 to 90%, preferably 30 to 80%, more preferably 40 to 60%, or total amount of thiosemicarbazide used was added, crystallization of Compound (XII) produced can be accelerated, and the reaction can be performed more efficiently. Depending on the reaction conditions, stability of Compound (XII) dissolved in the solvent may not be sufficient, and it is preferred that Compound (XII) produced should be immediately crystallized from the reaction solution.

Under the aforementioned preferred reaction conditions, the product (Compound (XII)) deposits as solid in the reaction mixture, and the deposited solid can be collected by, for example, filtration, or other techniques. Further, for washing of the resulting solid, for example, the solvent used for the reaction, water, mixed solvents of these and the like are used, and these washing solvents are preferably cooled before use. It is preferable to perform the washing with ice-cooled water or an ice-cooled mixed solvent of water and methanol (1:2 to 2:1, preferably 1:1).

Drying of the resulting solid is preferably performed, for example, at a temperature between 10° C. and 60° C. under reduced pressure for 30 minutes to 72 hours.

Step 3

Compound (IA) can be prepared by the reaction of Compound (XII) with $R^3COX$ (wherein $R^3$ and X have the same meaning as those mentioned above), or $(R^3CO)_2O$ (wherein $R^3$ has the same meaning as that mentioned above) in a solvent in the presence of a base.

Specifically, for example, Compound (IA) can be prepared by adding Compound (XII) to a suitable solvent, slowly adding $R^3COX$ (wherein $R^3$ and X have the same meaning as those mentioned above) or $(R^3CO)_2O$ (wherein $R^3$ has the same meaning as that mentioned above) to the mixture in the presence of a base at a temperature preferably between 0° C. and 30° C., and allowing them to react at a temperature preferably between 0° C. and 60° C., more preferably between 5° C. and 40° C., for 5 minutes to 72 hours, preferably 30 minutes to 10 hours. Compound (IA) can be isolated by preferably adding hydrochloric acid to the reaction mixture, removing the aqueous phase, if necessary, then adding water dropwise, collecting the deposited solid, washing and drying the resulting solid.

Examples of the solvent include, for example, hydrophilic solvents such as methanol, ethanol, acetone, methyl ethyl ketone, acetonitrile, propionitrile, dioxane, DMF, DMA, NMP and pyridine, non-hydrophilic solvents such as dichloromethane, chloroform, 1,2-dichloroethane, toluene, ethyl acetate, diethyl ether, THF and DME, water and the like, and they can be used alone or as a mixture. Preferred examples include hydrophilic solvents, more preferred examples include acetonitrile, propionitrile, acetone, methyl ethyl ketone, pyridine and the like, and still more preferred examples include acetonitrile. The amount of the solvent used is, for example, such an amount that the concentration of Compound (XII) should become 30 to 600 g/L, preferably 50 to 300 g/L, more preferably 80 to 120 g/L.

Examples of the base include, for example, potassium acetate, sodium hydrogencarbonate, potassium carbonate, potassium hydroxide, sodium hydroxide, sodium methoxide, potassium tert-butoxide, triethylamine, diisopropylethylamine, N-methylmorpholine, pyridine, DBU and the like, and preferred examples include pyridine and the like. The base is used in an amount of 2 to 12 equivalents, preferably 2.5 to 5 equivalents, to Compound (XII).

Examples of $R^3COX$ include, for example, $R^3COCl$, $R^3COBr$ and the like, and it is preferably used in an amount of 2 to 10 equivalents, more preferably 2.5 to 3.5 equivalents, to Compound (XII). $(R^3CO)_2O$ is preferably used in amount of 2 to 10 equivalents, more preferably 2.5 to 3.5 equivalents, to Compound (XII). These are preferably added dropwise to a mixture of Compound (XII), the base and the solvent with stirring under ice cooling.

For obtaining the deposited solid, for example, filtration and other techniques can be used.

For washing of the resulting solid, for example, water or the solvent used for the reaction, a mixed solvent of these or the like can be used, and these are preferably cooled before use.

It is preferable to wash the solid with a cooled mixed solvent of the solvent used for the reaction and water (30:1 to 1:1, preferably 15:1 to 5:1), and successively wash the same with cold water.

Drying of the resulting solid is preferably performed, for example, at a temperature between 10° C. and 70° C. under reduced pressure for 1 to 72 hours.

Preparing Method 6

Among Compound (II), Compound (IIA) wherein $R^1$ is a hydrogen atom, $R^2$ and $R^3$, which are the same, represent lower alkyl, and $R^4$ is tert-butoxycarbonylamino can also be prepared by using Compound (IA) obtained by Preparing method 5 or the like according to, for example, the method described in Preparing method 2.

[Formula 11]

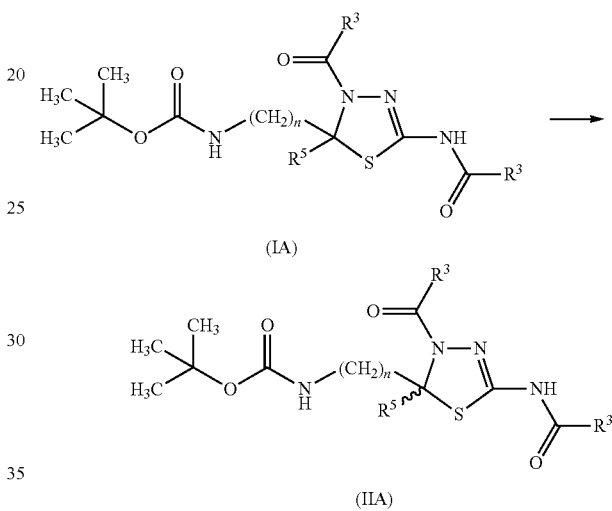

(wherein n, $R^3$ and $R^5$ have the same meaning as those mentioned above, respectively)

Preparing Method 7

Among Compounds (I) and (II), Compounds (IB) and (IIB) wherein $R^1$ is a hydrogen atom, $R^2$ and $R^3$, which are the same, represent lower alkyl, and $R^4$ is amino can also be prepared in accordance with the following step.

[Formula 12]

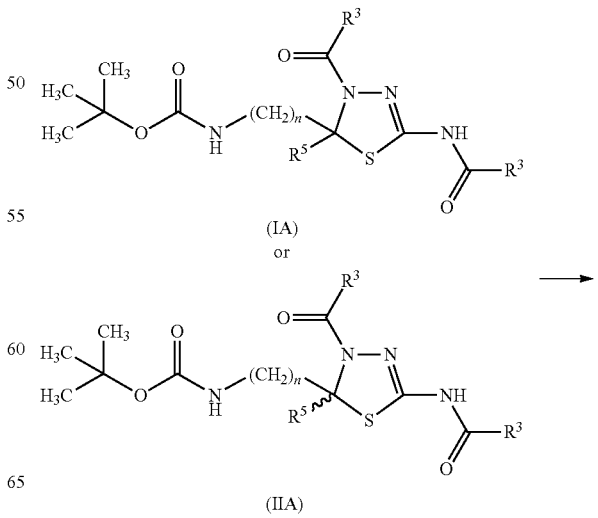

-continued

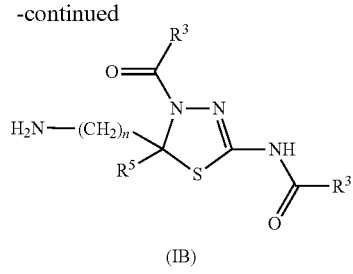

(IB)

or

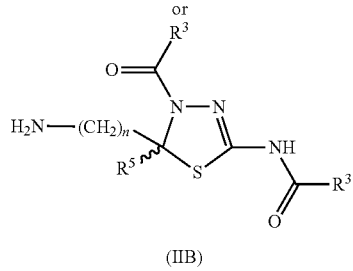

(IIB)

(wherein n, $R^3$ and $R^5$ have the same meanings as those mentioned above, respectively)

Compound (IB) or (IIB) can be prepared by treatment of Compound (IA) or (IIA) obtained by Preparing method 1, 2, 3, 5, 6 or the like with an appropriate acid.

Specifically, for example, hydrochloride of Compound (IB) or (IIB) can be prepared by dissolving Compound (IA) or (IIA) obtained by Preparing method 1, 2, 3, 5, 6 or the like in a suitable solvent, if necessary, and treating it with, for example, a solution containing hydrogen chloride. The treatment is preferably performed at a temperature between 0° C. to 60° C., more preferably between 5° C. and 40° C., for 5 minutes to 72 hours, more preferably 1 to 12 hours, and further stirring for 10 minutes to 4 hours under ice cooling, if necessary. Hydrochloride of Compound (IB) or (IIB) is preferably isolated by, for example, collecting solid deposited in the mixture, washing and drying the solid, if necessary.

Examples of the solution containing hydrogen chloride include, for example, a solution dissolving hydrogen chloride at a concentration of, for example, 1 to 12 mol/L, preferably 1 to 8 mol/L, more preferably 2 to 6 mol/L, in methyl acetate, ethyl acetate, propyl acetate, isopropyl acetate, butyl acetate, methanol, ethanol, dioxane or the like. Preferred examples include, for example, a solution dissolving hydrogen chloride at a concentration of, for example, 1 to 12 mol/L, preferably 1 to 8 mol/L, more preferably 2 to 6 mol/L, in a solvent such as methyl acetate, ethyl acetate, propyl acetate, isopropyl acetate, or butyl acetate, more preferably ethyl acetate, and particularly preferred are 4 mol/L hydrogen chloride in ethyl acetate and the like.

Examples of the solvent for dissolving Compound (IA) or (IIA) include, for example, the same solvents as those for the aforementioned solution containing hydrogen chloride, and specific preferred examples include ethyl acetate and the like.

As the method for obtaining the solid, for example, filtration and other techniques can be used.

Washing of the resulting solid is preferably performed by using a cooled solvent the same as that used for the aforementioned solution containing hydrogen chloride, specifically, preferably by using cold ethyl acetate or the like.

Drying of the resulting solid is performed, for example, preferably at a temperature between 10° C. and 120° C., more preferably 20° C. and 100° C., still more preferably 30° C. and 80° C., for 1 to 72 hours, preferably 1 to 24 hours, under reduced pressure.

Preparing Method 8

Among Compound (I), Compounds (ICa), (ICb) or (ICc) wherein $R^4$ is $NHSO_2R^7$ (wherein $R^7$ has the same meaning as that mentioned above), $NHR^{6E}$ [wherein $R^{6E}$ represents (a) lower alkyl which may have 1 or 2 substituents selected from the group consisting of hydroxy, lower alkoxy and $NR^{11}R^{12}$ (wherein $R^{11}$ and $R^{12}$ have the same meanings as those mentioned above, respectively), or cycloalkyl], or $NHCOR^8$ (wherein $R^8$ has the same meaning as that mentioned above), among the groups defined for $R^6$, can also be prepared in accordance with the following steps.

[Formula 13]

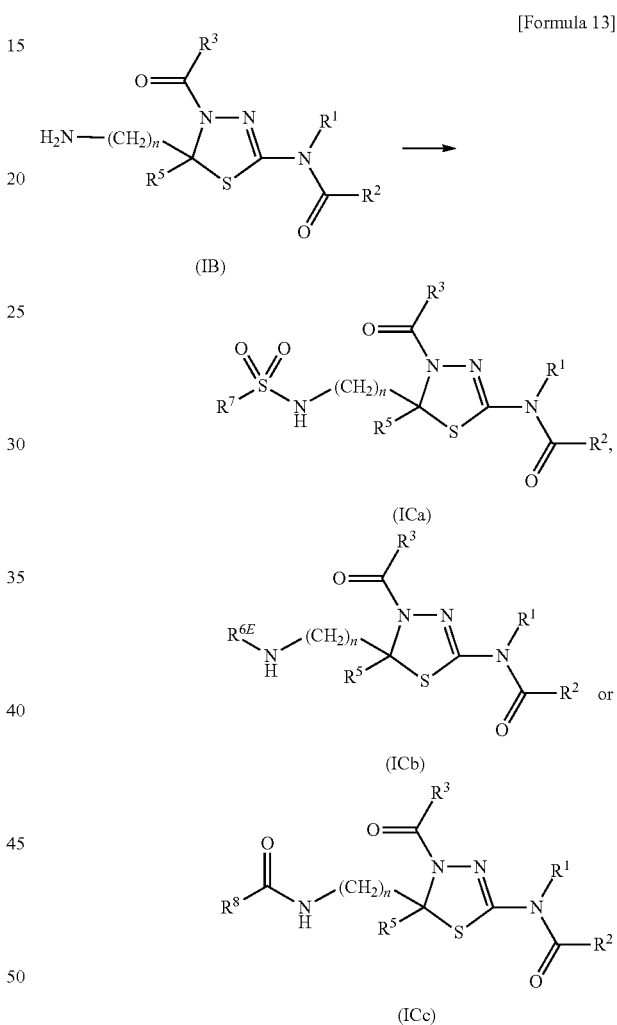

(wherein n, $R^1$, $R^2$, $R^3$, $R^5$, $R^7$, $R^{6E}$, and $R^8$ have the same meanings as those mentioned above, respectively)

Compound (ICa) can be prepared by the reaction of Compound (IB) obtained by Preparing method 1, 2, 4, 7 or the like with 1 to 20 equivalents, preferably 1 to 5 equivalents, of $R^7SO_2X$ (wherein $R^7$ and X have the same meanings as those mentioned above, respectively), or $(R^7SO_2)_2O$ (wherein $R^7$ has the same meaning as that mentioned above) in a suitable solvent in the presence of 0.5 to 20 equivalents, preferably 1 to 5 equivalents, of a base, if necessary, at a temperature between −20° C. and 150° C., preferably −10° C. and 30° C., for 5 minutes to 72 hours.

Examples of the solvent include, for example, dichloromethane, chloroform, 1,2-dichloroethane, toluene, ethyl acetate, acetonitrile, diethyl ether, THF, DME, dioxane, DMF, DMA, NMP, pyridine and the like, and they can be used alone or as a mixture.

Examples of the base include, for example, sodium hydrogencarbonate, potassium carbonate, potassium hydroxide, sodium hydroxide, sodium methoxide, potassium tert-butoxide, triethylamine, diisopropylethylamine, N-methylmorpholine, pyridine, DBU and the like.

Compound (ICb) can be obtained by the reaction of Compound (IB) obtained by Preparing method 1, 2, 4, 7 or the like with 1 to 20 equivalents of $R^{6E}X$ (wherein $R^{6E}$ and X have the same meanings as those mentioned above, respectively) in a suitable solvent in the presence of 0.5 to 20 equivalents of a base, if necessary, at a temperature between $-20°$ C. and $150°$ C. for 5 minutes to 72 hours.

Examples of the solvent include, for example, dichloromethane, chloroform, 1,2-dichloroethane, toluene, ethyl acetate, acetonitrile, diethyl ether, THF, DME, dioxane, DMF, DMA, NMP, pyridine and the like, and they can be used alone or as a mixture.

Examples of the base include, for example, sodium hydrogencarbonate, potassium carbonate, potassium hydroxide, sodium hydroxide, sodium methoxide, potassium tert-butoxide, triethylamine, diisopropylethylamine, N-methylmorpholine, pyridine, DBU and the like.

Moreover, as an alternative method, Compound (ICb) can be prepared by the reaction of Compound (IB) obtained by Preparing method 1, 2, 4, 7 or the like with preferably 1 to 20 equivalents, more preferably 1 to 5 equivalents, of a ketone or aldehyde corresponding to $R^{6E}$ (for example, formaldehyde when $R^{6E}$ is methyl, acetaldehyde when $R^{6E}$ is ethyl, acetone when $R^{6E}$ is isopropyl, and the like) in a suitable solvent in the presence of preferably 1 to 20 equivalents, more preferably 1 to 5 equivalents, of a reducing agent, and preferably 1 to 20 equivalents, more preferably 1 to 5 equivalents, of an acid at a temperature between $-20°$ C. and $150°$ C. for 5 minutes to 72 hours.

Examples of the reducing agent include, for example, sodium borohydride, sodium triacetoxyborohydride, sodium cyanoborohydride and the like.

Examples of the acid include, for example, hydrochloric acid, acetic acid, trifluoroacetic acid and the like.

Examples of the solvent include, for example, methanol, ethanol, dichloromethane, chloroform, 1,2-dichloroethane, toluene, ethyl acetate, acetonitrile, diethyl ether, THF, DME, dioxane, DMF, DMA, NMP, water and the like, and they can be used alone or as a mixture.

Compound (ICc) can be obtained by the reaction of Compound (IB) obtained by Preparing method 1, 2, 4, 7 or the like with 1 to 20 equivalents of $R^8COX$ (wherein $R^8$ and X have the same meanings as those mentioned above, respectively) or $(R^8CO)_2O$ (wherein $R^8$ has the same meaning as that mentioned above) without solvent or in a suitable solvent, if necessary, in the presence of 0.5 to 20 equivalents of a base at a temperature between $-20°$ C. and $150°$ C. for 5 minutes to 72 hours.

Examples of the solvent include, for example, dichloromethane, chloroform, 1,2-dichloroethane, toluene, ethyl acetate, acetonitrile, diethyl ether, THF, DME, dioxane, DMF, DMA, NMP, pyridine and the like, and they can be used alone or as a mixture.

Examples of the base include, for example, sodium hydrogencarbonate, potassium carbonate, potassium hydroxide, sodium hydroxide, sodium methoxide, potassium tert-butoxide, triethylamine, diisopropylethylamine, N-methylmorpholine, pyridine, DBU and the like.

By performing the same procedures as those mentioned above using Compound (IIB) obtained by Preparing method 2, 7 or the like instead of Compound (IB), Compounds (ICa) and (ICb) having the same configuration as that of Compound (IIB) can be obtained.

Preparing Method 9

Among Compound (I), Compound (ID) wherein $R^4$ is $NHSO_2CH_2CH_2R^{7E}$ [wherein $R^{7E}$ represents (α) (lower alkyl)thio which may be substituted with one or two substituents selected from the group consisting of hydroxy, amino, lower alkoxy, (lower alkyl)amino and di-(lower alkyl)amino; (β) a nitrogen-containing heterocyclic group which may be substituted with one to three substituents selected from the group consisting of lower alkyl which may be substituted with hydroxy, oxo, hydroxy, sulfanyl, amino, lower alkoxy, (lower alkyl)thio, (lower alkyl)amino, di-(lower alkyl)amino, formyl and lower alkanoyl; or (δ) $NR^{11}R^{12}$ (wherein $R^{11}$ and $R^{12}$ have the same meanings as those mentioned above, respectively), among the substituents of the lower alkyl defined for $R^7$] can also be prepared in accordance with the following steps.

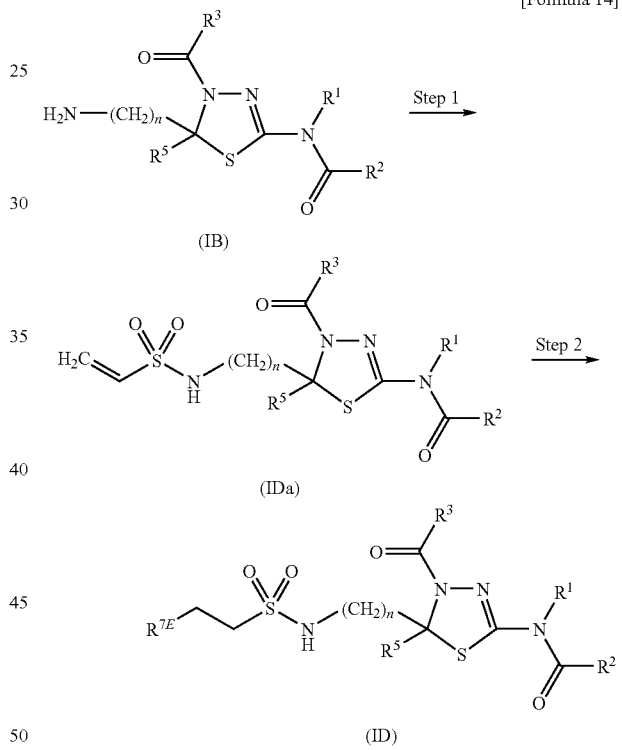

[Formula 14]

(wherein n, $R^1$, $R^2$, $R^3$, $R^5$ and $R^{7E}$ have the same meanings as those mentioned above, respectively)

Step 1

Compound (IDa) can be prepared by the reaction of Compound (IB) obtained by Preparing method 1, 2, 4, 7 or the like with 1 to 20 equivalents, preferably 1 to 5 equivalents of $ClCH_2CH_2SO_2Cl$ without solvent or in a suitable solvent, if necessary, in the presence of preferably 1 to 20 equivalents of a base at a temperature between $-20°$ C. and $150°$ C., preferably $-10°$ C. and $30°$ C., for 5 minutes to 72 hours, preferably 5 minutes to 5 hours. Compound (IB) can also preferably be used as an acid addition salt such as hydrochloride, and in such a case, the base is preferably used in an amount of 2 equivalents or more.

Examples of the solvent include, for example, dichloromethane, chloroform, 1,2-dichloroethane, toluene, ethyl acetate, acetonitrile, diethyl ether, THF, DME, dioxane, DMF, DMA, NMP, N,N'-dimethylimidazolidinone (DMI), pyridine and the like, and they can be used alone or as a mixture. Ethyl acetate, acetonitrile and the like are particularly preferred.

Examples of the base include, for example, sodium hydrogencarbonate, potassium carbonate, potassium hydroxide, sodium hydroxide, sodium methoxide, potassium tert-butoxide, triethylamine, diisopropylethylamine, N-methylmorpholine, pyridine, N-methylpiperidine, N,N'-dimethylpiperazine, DBU and the like.

Step 2

Compound (ID) can be prepared by the reaction of Compound (IDa) obtained in Step 1 mentioned above with 1 equivalent to large excess amount, preferably 5 to 100 equivalents, more preferably 10 to 20 equivalents of $HNR^{11}R^{12}$ (wherein $R^{11}$ and $R^{12}$ have the same meanings as those mentioned above, respectively), a nitrogen-containing heterocyclic compound having at least one nitrogen atom binding to a hydrogen atom, which may be substituted with one to three substituents selected from the group consisting of lower alkyl which may be substituted with hydroxy, oxo, hydroxy, sulfanyl, amino, lower alkoxy, (lower alkyl)thio, (lower alkyl)amino, di-(lower alkyl)amino, formyl and lower alkanoyl, or $R^{7EA}SH$ (wherein $R^{4EA}$ represents a lower alkyl moiety which may have a substituent of ($\alpha$) (lower alkyl)thio which may be substituted with one or two substituents selected from the group consisting of hydroxy, amino, lower alkoxy, (lower alkyl)amino and di-(lower alkyl)amino among the substituents of the lower alkyl defined for $R^7$) without solvent or in a suitable solvent, if necessary, in the presence of 1 to 10 equivalent a base at a temperature between $-10°$ C. and $150°$ C., preferably $-10°$ C. and $40°$ C., for 5 minutes to 72 hours.

Examples of the solvent include, for example, methanol, ethanol, propanol, 2-propanol, butanol, dichloromethane, chloroform, 1,2-dichloroethane, toluene, ethyl acetate, acetonitrile, diethyl ether, THF, DME, dioxane, DMF, DMA, NMP, pyridine, water and the like, and they can be used alone or as a mixture. Methanol, ethanol or the like or a mixed solvent of these and water are preferred.

Examples of the base include, for example, sodium hydrogencarbonate, potassium carbonate, potassium hydroxide, sodium hydroxide, sodium methoxide, potassium tert-butoxide, triethylamine, diisopropylethylamine, N-methylmorpholine, pyridine, DBU and the like.

Among Compound (0), Compound (III) wherein $R^0$ is aryl which may be substituted with one to three substituents selected from the group consisting of halogen, hydroxy, cyano and lower alkyl can be prepared by the following methods.

Preparing Method 10

Compound (III) can be prepared by the method described in WO2005/035512, or a method similar thereto.

Preparing Method 11

Compound (III) can be prepared from Compound (A) obtained by the method described in WO2003/051854, WO2004/092147, WO2004/111024 or the like, or a method similar thereto in accordance with the following steps.

[Formula 15]

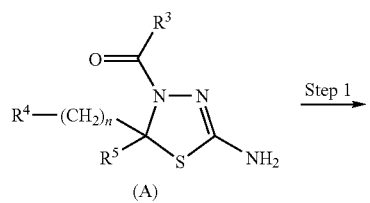

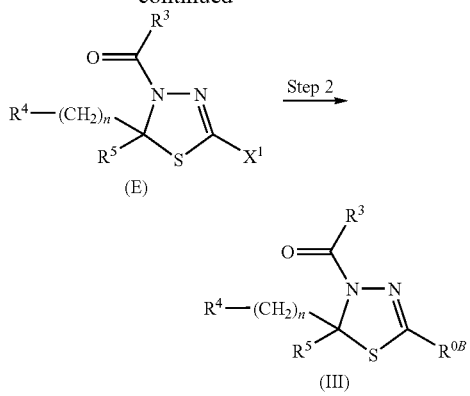

[wherein $X^1$ represents each atom of chlorine, bromine and iodine, $R^3$, $R^4$ and $R^5$ have the same meanings as those mentioned above, respectively, and $R^{OB}$ represents aryl which may be substituted with one to three substituents selected from the group consisting of halogen, hydroxy, cyano and lower alkyl, among the groups defined for $R^0$]

Step 1

Compound (E) can be prepared by the method described in J. Chem. Soc. Chem. Commun.), Vol. 8, p. 873 (1998) or the like, or a method similar thereto.

Specifically, Compound (E) can be prepared by the reaction of Compound (A) with 1 to 30 equivalents of a nitrous acid compound such as sodium nitrite and tert-butyl nitrite without solvent or in a suitable solvent, if necessary, in the presence of 0.1 to 50 equivalents of a suitable acid at a temperature between $-50°$ C. and $100°$ C. for 5 minutes to 48 hours to prepare a corresponding diazonium salt, and the following reaction of the diazonium salt with 1 to 30 equivalents of, for example, a copper halide, iodine and the like in a suitable solvent, if necessary, with addition of 1 to 30 equivalents of potassium iodide at a temperature between $-50°$ C. and $200°$ C. for 5 minutes to 48 hours.

Examples of the suitable solvent used for each reaction include, for example, methanol, ethanol, dichloromethane, chloroform, acetonitrile, toluene, ethyl acetate, THF, 1,4-dioxane, DMF, NMP, water and the like, and they can be used alone or as a mixture. Examples of the suitable acid include, for example, hydrochloric acid, hydrobromic acid, sulfuric acid, acetic acid, trifluoroacetic acid and the like. Examples of the copper halide include, for example, copper chloride, copper bromide, copper iodide and the like. These copper halides can be prepared by, for example, adding sodium chloride, sodium bromide or the like to aqueous copper sulfate, and then performing reduction with sodium nitrite, and the product can also be used in this step as it is without purification.

Furthermore, Compound (E) can also be prepared by the reaction with copper halide in one pot without isolation of diazonium salt. Specifically, Compound (E) can also be prepared by the reaction of Compound (A), 1 to 30 equivalents of the nitrous acid compound exemplified above, 1 to 30 equivalents of the copper halide exemplified above, iodine, potassium iodide and the like as a mixture in the suitable solvent exemplified above at a temperature between $-50°$ C. and $200°$ C. for 5 minutes to 48 hours.

Step 2

Compound (III) can be prepared by the reaction of Compound (E) obtained in Step 1 mentioned above and 1 to 30 equivalents of $(R^{OB})_pM_q(R^A)_r$ (wherein $R^{OB}$ has the same meaning as that mentioned above, M represents each atom of tin, zinc, boron, silicon, aluminum, zirconium, copper, or mercury, $R^4$ represents hydroxy, halogen having the same meaning as that mentioned above, lower alkyl having the same meaning as that mentioned above, lower alkoxy having the same meaning as that mentioned above, aryl having the same meaning as that mentioned above, or aryloxy having the same meaning as that mentioned above, p and q are the same or different, and each represents 1 or 2, and r represents an integer of 0 to 3) in a suitable solvent in the presence of 0.001 to 1 equivalent of a transition metal catalyst at a temperature between −50° C. and 200° C. for 5 minutes to 80 hours. In this reaction, 0.01 to 30 equivalents of a suitable additive may also be added to accelerate the reaction.

Examples of the suitable solvent include, for example, methanol, ethanol, dichloromethane, chloroform, acetonitrile, toluene, ethyl acetate, THF, 1,4-dioxane, DMF, NMP, water and the like, and they can be used alone or as a mixture. Examples of the transition metal catalyst include, for example, palladium catalysts such as palladium acetate, tetrakis(triphenylphosphine)palladium, palladium chloride, palladium bromide, bis(triphenylphosphine)palladium chloride, dichlorobis(acetonitrile)palladium, and bis(dibenzylideneacetone)palladium, nickel catalysts such as nickel chloride, nickel acetylacetonate, bis(1,5-cyclooctadiene) nickel, and nickel bromide, and the like. Examples of the suitable additive include, for example, triphenylphosphine, tri(o-tolyl)phosphine, 1,1'-bis(diphenylphosphino)ferrocene, 1,2-bis(diphenylphosphino)propane, 2,2'-bis(diphenylphosphino)-1,1'-binaphthyl, 1,2-bis(diphenylphosphino)ethane, silver oxide, copper iodide, lithium chloride, cesium fluoride, triethylamine, diethylamine, sodium hydroxide, potassium hydroxide, sodium carbonate, tetrabutylammonium fluoride, and the like, and they can be used alone or as a mixture.

Preparing Method 12

Compound (I0) can be prepared from Compound (F) wherein $R^2$ is a hydrogen atom among Compound (I0), which is obtained by the method described in WO2003/051854, WO2004/092147, WO2004/111024, WO2005/035512 or the like, in accordance with the following steps.

[Formula 16]

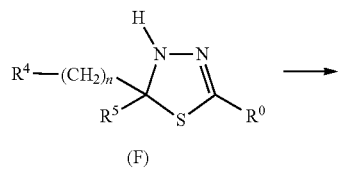

(F)

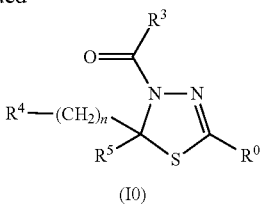

(I0)

(wherein $R^0$, $R^3$, $R^4$ and $R^5$ have the same meanings as those mentioned above, respectively)

Compound (I0) can be obtained by the reaction of Compound (F) and 1 to 30 equivalents of $R^3COX$ (wherein $R^3$ and X have the same meaning as those mentioned above) or $(R^3CO)_2O$ (wherein $R^3$ has the same meaning as that mentioned above) without solvent or in a suitable solvent in the presence or absence of 0.01 to 50 equivalents of a suitable base at a temperature between −50° C. to the boiling point of the solvent used for 5 minutes to 48 hours.

Examples of the suitable solvent include, for example, methanol, ethanol, dichloromethane, acetonitrile, toluene, ethyl acetate, THF, 1,4-dioxane, DMF, NMP and the like, and they can be used alone or as a mixture. Examples of the suitable base include, for example, sodium hydride, lithium hydroxide, cesium fluoride, triethylamine, diethylamine, sodium hydroxide, potassium hydroxide, sodium carbonate, potassium carbonate, triethylamine, diisopropylamine, DBU, 4-dimethylaminopyridine and the like, and they can be used alone or as a mixture.

Among Compounds (0) and (00), stereoisomers such as geometrical isomers and optical isomers, regioisomers, tautomers and the like may be existed. Including these isomers, all possible isomers and the mixtures thereof can be used for the therapeutic and/or prophylactic agent for restenosis of the present invention.

To obtain a salt of Compound (0) or (00), when Compound (0) or (00) is obtained as a salt form, the salt, per se, may be purified. When Compound (0) or (00) is obtained as a free form, Compound (0) or (00) may be dissolved or suspended in an appropriate solvent, and added an appropriate acid or base to form a salt and then be isolated and purified.

In addition, Compound (0), (00) or (IV) or a pharmaceutically acceptable salt thereof may exist in the form of adducts with water or various solvents. These adducts can also be used for the therapeutic and/or prophylactic agent for restenosis of the present invention.

Specific examples of Compounds (0) and (00) are shown in Tables 1 to 9. However, Compounds (0) and (00) used for the therapeutic and/or prophylactic agent for restenosis of the present invention are not limited to these examples.

TABLE 1

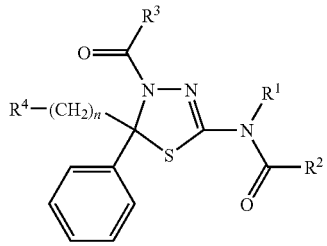

| Ref. Ex. No. | Compound No. | n | $R^1$ | $R^2$ | $R^3$ | $R^4$ |
|---|---|---|---|---|---|---|
| 1 | 1 | 3 | H | $C(CH_3)_3$ | $C(CH_3)_3$ | $NHCH_2CH_2CH_2OH$ |
| 2 | 2 | 3 | H | $C(CH_3)_3$ | $C(CH_3)_3$ | $NHCH_2CH_2N(CH_3)_2$ |

TABLE 1-continued

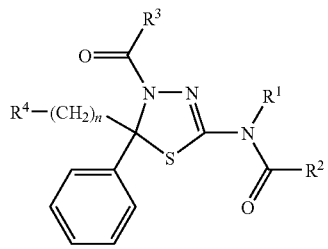

| Ref. Ex. No. | Compound No. | n | R¹ | R² | R³ | R⁴ |
|---|---|---|---|---|---|---|
| 3 | 3 | 2 | H | C(CH₃)₃ | C(CH₃)₃ | NHSO₂CH₃ |
| 4 | 4 | 2 | H | C(CH₃)₃ | CH₂CH₃ | NHSO₂CH₃ |
| 5 | 5 | 2 | CH₂CH₂CH₂ | | C(CH₃)₃ | NHSO₂CH₃ |
| 6 | 6 | 2 | H | C(CH₃)₃ | CH(CH₃)₂ | NHSO₂CH₃ |
| 7 | 7 | 2 | CH₂CH₂CH₂ | | CH₂CH₃ | NHSO₂CH₃ |
| 8 | 8 | 3 | H | C(CH₃)₃ | C(CH₃)₃ | CONHCH₂CH₂OH |
| 9 | 9 | 1 | H | C(CH₃)₃ | C(CH₃)₃ | NHSO₂CH₂CH₂NHCH₂CH₃ |
| 10 | 10 | 1 | H | C(CH₃)₃ | C(CH₃)₃ | NHSO₂CH=CH₂ |
| 11 | 11 | 1 | H | C(CH₃)₃ | C(CH₃)₃ | NH₂ |
| 12 | 12 | 1 | H | C(CH₃)₃ | C(CH₃)₃ | NHSO₂CH₂CH₂N(CH₃)₂ |
| 13 | 13 | 1 | H | C(CH₃)₃ | C(CH₃)₃ | NHSO₂CH₂CH₂CH₂N(CH₃)₂ |
| 14 | 14 | 1 | H | C(CH₃)₃ | C(CH₃)₃ | NHOH |
| 15 | 15 | 1 | H | C(CH₃)₃ | C(CH₃)₃ | NHOCH₃ |
| 16 | 16 | 1 | H | C(CH₃)₃ | C(CH₃)₃ | NHOCH₂CH₃ |
| 17 | 17 | 1 | H | C(CH₃)₃ | C(CH₃)₃ | NHSO₂CH₂CH₂N(OH)CH₂CH₃ |
| 18 | 18 | 1 | H | C(CH₃)₃ | C(CH₃)₃ | NHSO₂CH₂CH₂N(OH) CH₃ |
| 19 | 19 | 1 | H | C(CH₃)₃ | C(CH₃)₃ | NHSO₂CH₂CH₂N(OCH₃) CH₃ |

TABLE 2

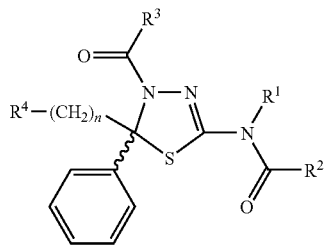

| Ref. Ex. No. | Compound No. | n | R¹ | R² | R³ | R⁴ |
|---|---|---|---|---|---|---|
| 20 | a | 2 | H | C(CH₃)₃ | C(CH₃)₃ | NHSO₂CH₃ |
| 21 | b | 2 | H | C(CH₃)₃ | CH₂CH₃ | NHSO₂CH₃ |
| 22 | c | 2 | CH₂CH₂CH₂ | | C(CH₃)₃ | NHSO₂CH₃ |
| 23 | d | 2 | H | C(CH₃)₃ | CH(CH₃)₂ | NHSO₂CH₃ |
| 24 | e | 2 | CH₂CH₂CH₂ | | CH₂CH₃ | NHSO₂CH₃ |
| 25 | f | 2 | H | C(CH₃)₃ | CH₃ | NHSO₂CH₃ |
| 26* | g | 2 | CH₂CH₂CH₂ | | CH₃ | NHSO₂CH₃ |
| 27 | h | 2 | CH₂CH₂CH₂CH₂ | | CH₃ | NHSO₂CH₃ |
| 28* | i | 2 | H | C(CH₃)₃ | C(CH₃)₃ | NHSO₂CH₂CH₂NHCH₂CH₃ |
| 29* | j | 1 | H | C(CH₃)₃ | C(CH₃)₃ | NH₂ |
| 30* | k | 1 | H | C(CH₃)₃ | C(CH₃)₃ | NHSO₂CH=CH₂ |
| 31 | l | 1 | H | C(CH₃)₃ | C(CH₃)₃ | NHSO₂CH₂CH₂NHCH₂CH₃ |
| 32 | m | 1 | H | C(CH₃)₃ | C(CH₃)₃ | NHSO₂CH₂CH₂N(CH₃)₂ |
| 33 | n | 1 | H | C(CH₃)₃ | C(CH₃)₃ | NHSO₂CH₂CH₂CH₂N(CH₃)₂ |
| 34* | o | 3 | H | C(CH₃)₃ | C(CH₃)₃ | CONHCH₂CH₂OH |
| 35* | p | 2 | H | C(CH₃)₃ | C(CH₃)₃ | NHSO₂CH₂CH₂N(OH)CH₂CH₃ |
| 36* | q | 1 | H | C(CH₃)₃ | C(CH₃)₃ | NHOH |
| 37 | r | 1 | H | C(CH₃)₃ | C(CH₃)₃ | NHOCH₃ |
| 38 | s | 1 | H | C(CH₃)₃ | C(CH₃)₃ | NHOCH₂CH₃ |
| 39 | t | 1 | H | C(CH₃)₃ | C(CH₃)₃ | NHSO₂CH₂CH₂N(OH)CH₂CH₃ |
| 40 | u | 1 | H | C(CH₃)₃ | C(CH₃)₃ | NHSO₂CH₂CH₂N(OH)CH₃ |
| 41 | v | 1 | H | C(CH₃)₃ | C(CH₃)₃ | NHSO₂CH₂CH₂N(OCH₃)CH₃ |
| 42* | w | 1 | H | C(CH₃)₃ | C(CH₃)₃ | NHSO₂CH₂CH₂CH₂NH₂ |
| 43 | x | 1 | H | C(CH₃)₃ | C(CH₃)₃ | NHCOOC(CH₃)₃ |

*Specific rotation was not determined.

TABLE 3

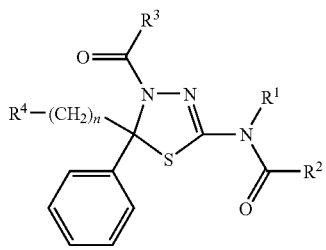

| Ref. Ex. No. | Compound No. | n | R¹ | R² | R³ | R⁴ |
|---|---|---|---|---|---|---|
| 44 | 21 | 2 | H | C(CH₃)₃ | C(CH₃)₃ | NHSO₂CH₂CH₂NHCH₂CH₃ |
| 45 | 22 | 1 | H | C(CH₃)₃ | C(CH₃)₃ | NHCOOC(CH₃)₃ |
| 46 | 23 | 1 | H | C(CH₃)₃ | C(CH₃)₃ | NHSO₂CH₂CH₂NHOH |
| 47 | 24 | 1 | H | C(CH₃)₃ | C(CH₃)₃ | NHSO₂CH₂CH₂SCH₂CH₂NH₂ |
| 48 | 25 | 1 | H | C(CH₃)₃ | C(CH₃)₃ | NHSO₂CH₂SCH₂CH₂NH₂ |
| 49 | 26 | 2 | CH₂CH₂CH₂CH₂ | | CH₃ | NHSO₂CH₃ |

TABLE 4

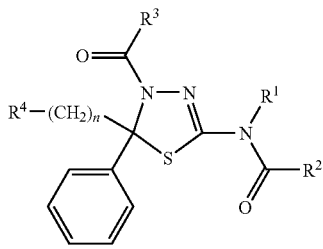

| Ref. Ex. No. | Compound No. | n | R¹ | R² | R³ | R⁴ |
|---|---|---|---|---|---|---|
| 50 | 50 | 1 | H | CH₃ | CH₃ | H |
| 51 | 51 | 1 | H | C(CH₃)₃ | CH₃ | NHSO₂(CH₂)₂NHCH₂CH₃ |
| 52 | 52 | 1 | H | C(CH₃)₃ | C(CH₃)₃ | NHSO₂CH₂CH₂NH₂ |
| 53 | 53 | 1 | H | C(CH₃)₃ | C(CH₃)₃ | NHSO₂N(CH₃)₂ |
| 54 | 54 | 1 | H | C(CH₃)₃ | C(CH₃)₃ | NHSO₂(CH₃)₃NH₂ |
| 55 | 55 | 1 | H | C(CH₃)₃ | C(CH₃)₃ | •—NHSO₂(CH₂)₂—N(H)(cyclopropyl) |
| 56 | 56 | 1 | H | C(CH₃)₃ | C(CH₃)₃ | NHSO₂(CH₂)₂NHCOCH₂NH₂ |
| 57 | 57 | 1 | H | C(CH₃)₃ | C(CH₃)₃ | •—NHSO₂(CH₂)₂—N(CH₂CH₃)(cyclopropyl) |
| 58 | 58 | 1 | H | C(CH₃)₃ | C(CH₃)₃ | NHSO₂(CH₂)₂N(CH₂CH₃)₂ |
| 59 | 59 | 1 | H | C(CH₃)₃ | C(CH₃)₃ | NHSO₂(CH₂)₂NHCH₂CH(CH₃)₂ |
| 60 | 60 | 1 | H | C(CH₃)₃ | C(CH₃)₃ | NHSO₂(CH₂)₂NH(CH₂)₃CH₃ |
| 61 | 61 | 1 | H | C(CH₃)₃ | C(CH₃)₃ | NHSO₂(CH₂)₂N(CH₃)CH₂CH₃ |
| 62 | 62 | 1 | H | C(CH₃)₃ | C(CH₃)₃ | NHSO₂(CH₂)₃N(CH₂CH₃)₂ |
| 63 | 63 | 2 | H | C(CH₃)₃ | C(CH₃)₃ | •—N(H)—CO—(S)-pyrrolidin-2-yl |
| 64 | 64 | 3 | H | C(CH₃)₃ | C(CH₃)₃ | NHCH₂CH₂OH |
| 65 | 65 | 3 | H | C(CH₃)₃ | C(CH₃)₃ | NHCH₃ |
| 66 | 66 | 3 | H | C(CH₃)₃ | C(CH₃)₃ | NHCH₂CH₃ |
| 67 | 67 | 3 | CH₂CH₂CH₂CH₂ | | C(CH₃)₃ | NH₂ |
| 68 | 68 | 3 | H | C(CH₃)₃ | CH₃ | NH₂ |
| 69 | 69 | 3 | CH₂CH₂CH₂ | | CH₃ | NH₂ |
| 70 | 70 | 3 | CH₂CH₂CH₂CH₂ | | CH₃ | NH₂ |

TABLE 4-continued

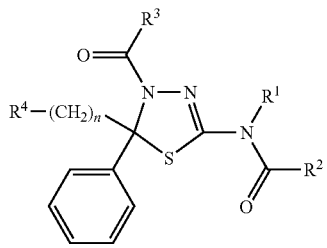

| Ref. Ex. No. | Compound No. | n | R¹ | R² | R³ | R⁴ |
|---|---|---|---|---|---|---|
| 71 | 71 | 2 | H | $C(CH_3)_3$ | $C(CH_3)_3$ | $CONHCH_2CONH_2$ |
| 72 | 72 | 1 | H | $C(CH_3)_3$ | $C(CH_3)_3$ | $NHSO_2(CH_2)_2NHCH(CH_3)_2$ |

TABLE 5

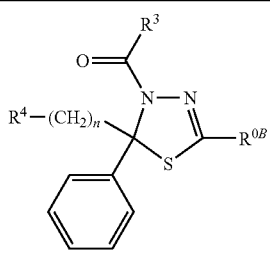

| Ref. Ex. No. | Compound No. | n | $R^{OB}$ | R³ | R⁴ |
|---|---|---|---|---|---|
| 73 | 73 | 1 | 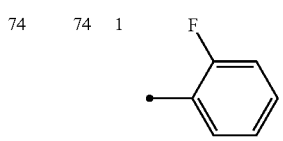 | $CH_3$ | $NHSO_2CH_3$ |
| 74 | 74 | 1 | 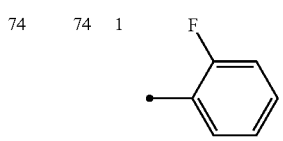 | $CH_3$ | $NHSO_2CH_2CH_2NH_2$ |

TABLE 5-continued

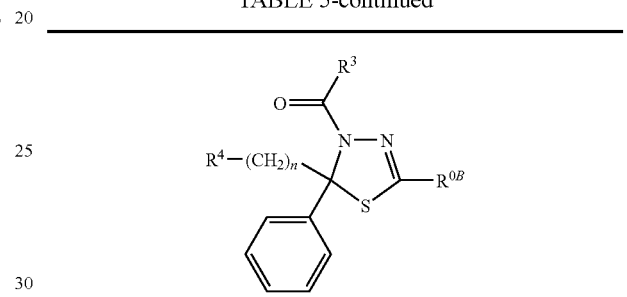

| Ref. Ex. No. | Compound No. | n | $R^{OB}$ | R³ | R⁴ |
|---|---|---|---|---|---|
| 75 | 75 | 1 |  | $CH_3$ | $NHSO_2CH_2CH_2N(CH_3)_2$ |

TABLE 6

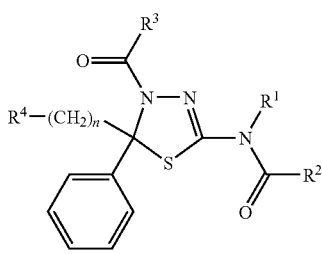

| Ref. Ex. No. | Compound No. | n | R¹ | R² | R³ | R⁴ |
|---|---|---|---|---|---|---|
| 76 | 76 | 1 | H | $C(CH_3)_3$ | $CH_3$ | $NHSO_2(CH_2)_2S(CH_2)_2NH_2$ |
| 77 | 77 | 1 | H | $C(CH_3)_3$ | $CH_3$ | $NHSO_2(CH_2)_2S(CH_2)_2N(CH_2CH_3)_2$ |
| 78 | 78 | 1 | H | $C(CH_3)_3$ | $CH_3$ | $NHSO_2(CH_2)_2S(CH_2)_2OH$ |
| 79 | 79 | 1 | H | $C(CH_3)_3$ | $CH_3$ | $NHSO_2(CH_2)_2S(CH_2)_2NHCH_2CH_3$ |
| 80 | 80 | 1 | H | $C(CH_3)_3$ | $CH_3$ | $NHSO_2(CH_2)_2S(CH_2)_3NH_2$ |
| 81 | 81 | 1 | H | $C(CH_3)_3$ | $CH_3$ | $NHSO_2(CH_2)_2S(CH_2)_2NH_2$ |
| 82 | 82 | 1 | $CH_2CH_2CH_2$ | | $CH_3$ | $NHSO_2(CH_2)_2S(CH_2)_2NH_2$ |
| 83 | 83 | 1 | $CH_2CH_2CH_2CH_2$ | | $CH_3$ | $NHSO_2(CH_2)_2S(CH_2)_2NH_2$ |

TABLE 6-continued

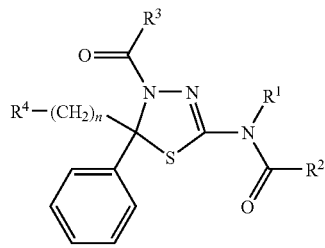

| Ref. Ex. No. | Compound No. | n | R¹ | R² | R³ | R⁴ |
|---|---|---|---|---|---|---|
| 84 | 84 | 1 | H | $C(CH_3)_3$ | $C(CH_3)_3$ | •—$NHSO_2(CH_2)_2$—S—(2-pyridyl) |
| 85 | 85 | 1 | H | $C(CH_3)_3$ | $C(CH_3)_3$ | •—$NHSO_2(CH_2)_2$—S—(4-hydroxypyrimidin-2-yl) |
| 86 | 86 | 1 | H | $C(CH_3)_3$ | $C(CH_3)_3$ | •—$NHSO_2(CH_2)_2$—O—(5-methyl-1H-pyrazol-3-yl) |

TABLE 7

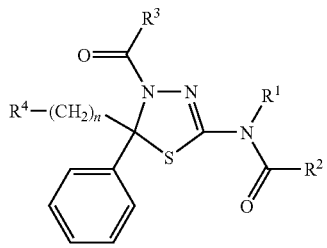

| Ref. Ex. No. | Compound No. | n | R¹ | R² | R³ | R⁴ |
|---|---|---|---|---|---|---|
| 87 | 87 | 1 | $CH_2CH_2CH_3$ | | $CH_3$ | $NHSO_2CH_2S(CH_2)_2NH_2$ |
| 88 | 88 | 1 | $CH_2CH_2CH_2CH_3$ | | $CH_3$ | $NHSO_2CH_2S(CH_2)_2NH_2$ |
| 89 | 89 | 1 | H | $C(CH_3)_3$ | $C(CH_3)_3$ | $NHSO_2CH_2S(CH_2)_2N(CH_3)_2$ |
| 90 | 90 | 1 | H | $C(CH_3)_3$ | $CH_3$ | $NHSO_2CH_2S(CH_2)_2NH_2$ |
| 91 | 91 | 3 | H | $C(CH_3)_3$ | $C(CH_3)_3$ | $NHSO_2(CH_2)_2S(CH_2)_2NH_2$ |
| 92 | 92 | 1 | H | $C(CH_3)_3$ | $C(CH_3)_3$ | $NHSO_2(CH_2)_3OH$ |
| 93 | 93 | 1 | H | $C(CH_3)_3$ | $CH_3$ | $NHSO_2(CH_2)_2OH$ |
| 94 | 94 | 1 | H | $C(CH_3)_3$ | $C(CH_3)_3$ | $NHSO_2(CH_2)_3S(CH_2)_2NH_2$ |
| 95 | 95 | 3 | H | $C(CH_3)_3$ | $C(CH_3)_3$ | $NH_2$ |

TABLE 8

[Structure: 1,3,4-thiadiazoline core with R⁴—CH₂ and phenyl at C5, N3—C(O)R³, C2=N—N(R¹)—C(O)R²]

| Ex. No. | Compound No. | R¹ | R² | R³ | R⁴ |
|---|---|---|---|---|---|
| 15 | 100 | H | C(CH₃)₃ | C(CH₃)₃ | —NHSO₂(CH₂)₂—N(piperazine)N—COCH₃ |
| 16 | 101 | H | C(CH₃)₃ | CH₃ | —NHSO₂(CH₂)₂—N(piperidine)-4-OH |
| 17 | 102 | H | C(CH₃)₃ | C(CH₃)₃ | —NHSO₂(CH₂)₂—N(piperidine) |
| 18 | 103 | H | C(CH₃)₃ | C(CH₃)₃ | —NHSO₂(CH₂)₂—N(morpholine) |
| 19 | 104 | H | C(CH₃)₃ | C(CH₃)₃ | —NHSO₂(CH₂)₂—N(thiomorpholine) |
| 20 | 105 | H | C(CH₃)₃ | C(CH₃)₃ | —NHSO₂(CH₂)₂—N(piperazin-2-one) |
| 21 | 106 | H | C(CH₃)₃ | C(CH₃)₃ | —NHSO₂(CH₂)₂—N(1,4-dioxa-8-azaspiro[4.5]decane) |
| 22 | 107 | H | C(CH₃)₃ | C(CH₃)₃ | —NHSO₂(CH₂)₂—N(4-oxopiperidine) |
| 23 | 108 | H | C(CH₃)₃ | C(CH₃)₃ | —NHSO₂(CH₂)₂—N(oxazolidin-2-one) |
| 24 | 109 | H | C(CH₃)₃ | C(CH₃)₃ | —NHSO₂(CH₂)₂—N(imidazole) |
| 25 | 110 | H | C(CH₃)₃ | C(CH₃)₃ | —NHSO₂(CH₂)₂—N(pyrazole) |

TABLE 8-continued
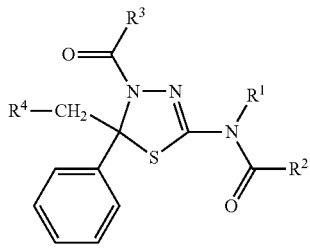
| Ex. No. | Compound No. | R¹ | R² | R³ | R⁴ |
|---|---|---|---|---|---|
| 26 | 111 | H | C(CH₃)₃ | C(CH₃)₃ | 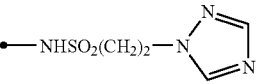 |
| 27 | 112 | H | C(CH₃)₃ | C(CH₃)₃ | 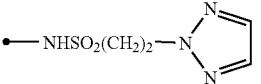 |
| 28 | 113 | H | C(CH₃)₃ | C(CH₃)₃ | 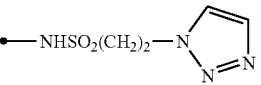 |
| 29 | 114 | H | C(CH₃)₃ | C(CH₃)₃ | 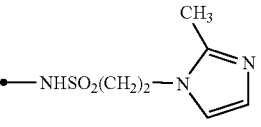 |
| 30 | 115 | H | C(CH₃)₃ | CH₃ | 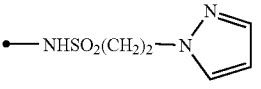 |
| 31 | 116 | CH₂CH₂CH₂CH₂ | | CH₃ | 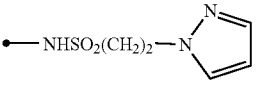 |
| 32 | 117 | H | C(CH₃)₃ | C(CH₃)₃ | 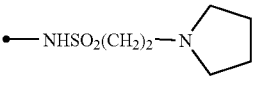 |
| 33 | 118 | H | C(CH₃)₃ | C(CH₃)₃ | 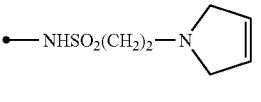 |
| 34 | 119 | H | C(CH₃)₃ | C(CH₃)₃ | 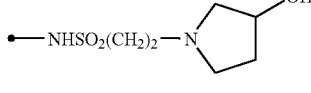 |
| 35 | 120 | H | C(CH₃)₃ | C(CH₃)₃ | 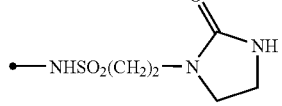 |

TABLE 8-continued
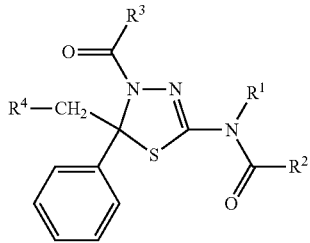
| Ex. No. | Compound No. | R¹ | R² | R³ | R⁴ |
|---|---|---|---|---|---|
| 36 | 121 | H | C(CH₃)₃ | C(CH₃)₃ | 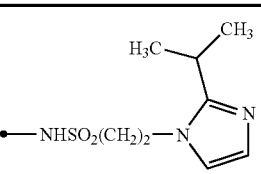 |
| 37 | 122 | H | C(CH₃)₃ | C(CH₃)₃ | 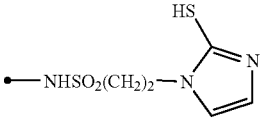 |
| 38 | 123 | H | C(CH₃)₃ | C(CH₃)₃ | 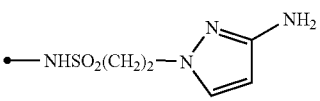 |
| 39 | 124 | H | C(CH₃)₃ | C(CH₃)₃ | 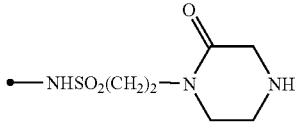 |
| 40 | 125 | H | C(CH₃)₃ | C(CH₃)₃ | 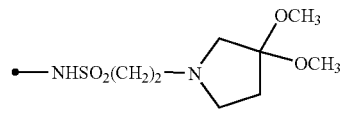 |
| 41 | 126 | H | C(CH₃)₃ | C(CH₃)₃ | 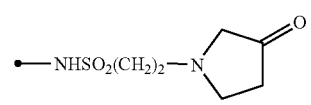 |
| 42 | 127 | H | C(CH₃)₃ | C(CH₃)₃ | 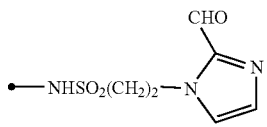 |
| 43 | 128 | H | C(CH₃)₃ | C(CH₃)₃ | 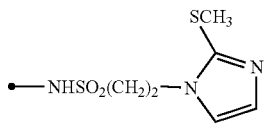 |
| 44 | 129 | H | C(CH₃)₃ | CH₃ | 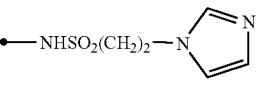 |
| 45 | 130 | H | C(CH₃)₃ | CH₃ | 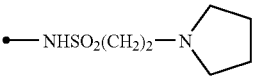 |

TABLE 8-continued
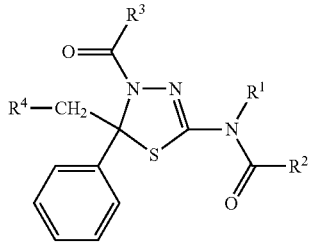
| Ex. No. | Compound No. | R¹ | R² | R³ | R⁴ |
|---|---|---|---|---|---|
| 46 | 131 | H | C(CH₃)₃ | C(CH₃)₃ | 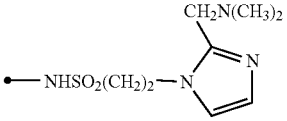 |
| 47 | 132 | H | C(CH₃)₃ | C(CH₃)₃ | 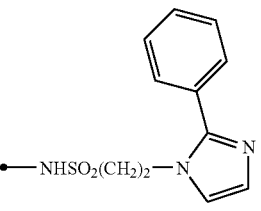 |
| 48 | 133 | H | C(CH₃)₃ | C(CH₃)₃ | 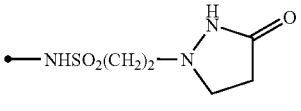 |
| 49 | 134 | H | C(CH₃)₃ | C(CH₃)₃ | 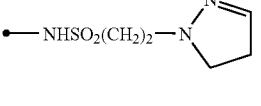 |
| 50 | 135 | H | C(CH₃)₃ | C(CH₃)₃ | 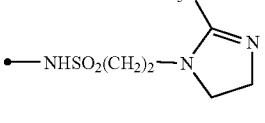 |
| 51 | 136 | H | C(CH₃)₃ | C(CH₃)₃ | 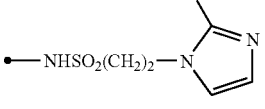 |
| 52 | 137 | H | C(CH₃)₃ | C(CH₃)₃ | 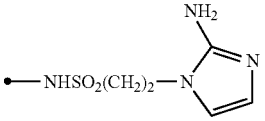 |
| 53 | 138 | H | C(CH₃)₃ | CH₃ | 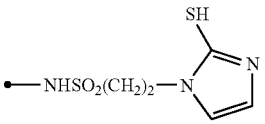 |

TABLE 9

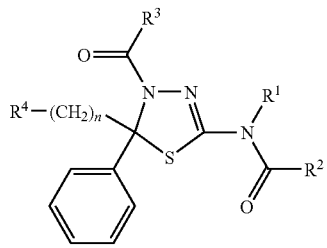

| Ex. No. | Compound No. | n | R¹ | R² | R³ | R⁴ |
|---|---|---|---|---|---|---|
| 54 | 139 | 1 | H | C(CH$_3$)$_3$ | C(CH$_3$)$_3$ | •—NHSO$_2$(CH$_2$)$_3$—phthalimidyl |

Next, pharmacological activities of Compounds (0) and (00) will be specifically explained by the following test example.

TEST EXAMPLE 1

Cell Growth Inhibition Tests Against Human Vascular Smooth Muscle Cells

As human vascular smooth muscle cells, normal human aortic smooth muscle cells (Cambrex, catalog No. C-2571) were used. HuMedia-SB2 basal medium (Kurabo Industries, Ltd., catalog No. KS-2150S) containing 5% fetal bovine serum (Kurabo Industries, Ltd., catalog No. KS-6150), 0.5 ng/mL human recombinant epidermal growth factor (Kurabo Industries, Ltd., catalog No. KS-6150), 2 ng/mL human recombinant basic fibroblast growth factor (Kurabo Industries, Ltd., catalog No. KS-6150), 5 μg/mL insulin (Kurabo Industries, Ltd., catalog number KS-6150), 50 μg/mL gentamycin (Kurabo Industries, Ltd., catalog No. KS-6150), and 50 ng/mL amphotericin B (Kurabo Industries, Ltd., catalog No. KS-6150) was used for cell culture. The cells were cultured at 37° C. in a 5% carbon dioxide atmosphere.

The normal human aortic smooth muscle cells (1000 cells/well) were seeded in each well of 96-well plates (Nunc, catalog No. 167008), and cultured overnight. Test compounds diluted stepwise were added, and the cells were further cultured for 72 hours (final volume: 100 μL/well). Fifty μL XTT labeling mixture of Cell Proliferation Kit II (XTT) (Roche Diagnostics, catalog No. 1465015) was added to each well, and the plates were incubated at 37° C. After 4 hours, absorbance at 490 nm (reference wavelength: 655 nm) was measured with a plate reader (Molecular Device, SpectraMax 340PC$^{384}$). Growth ratios of the cells in the wells treated with the test compound was calculated based on the growth ratio of the cells in the control well treated with solvent (dimethyl sulfoxide (DMSO)) for 72 hours, which was defined as 100%. From a plot of test compound concentrations and the cell growth ratios at the concentrations, the concentration of 50% growth inhibition, the GI$_{50}$ value, was calculated.

Compounds 1, 2, a, b, d, e, h, j, l, m, n and o showed growth inhibitory activities less than 10 μmol/L in terms of the GI$_{50}$ value against the normal human aortic smooth muscle cells. Further, Compounds i, k, 8, 24, 25, 50 to 75, 78, 95, 108 to 111, 113, 114, 117 to 124, 127, 128, 130, and 136 to 138 also showed growth inhibitory activities less than 10 μmol/L in terms of the GI$_{50}$ value.

Furthermore, Compound m and the like showed more potent inhibitory activities compared with Compound 12 and the like, which are corresponding racemic mixtures.

From the results of this test, it is considered that Compounds (0) and (00) show cell growth inhibitory activity against the normal human aortic smooth muscle cells, namely, they are considered useful as therapeutic and/or prophylactic agents for restenosis.

Compound (0), (00) or (IV), or a pharmaceutically acceptable salt thereof can be administered alone. However, usually, Compound (0), (00) or (IV), or a pharmaceutically acceptable salt thereof is preferably provided in various pharmaceutical preparations. Furthermore, these pharmaceutical preparations are used for animals and humans.

The pharmaceutical preparations according to the present invention may comprise Compound (0), (00) or (IV), or a pharmaceutically acceptable salt thereof alone as an active ingredient. Alternatively, the pharmaceutical preparations may comprise a mixture of Compound (0), (00) or (IV), or a pharmaceutically acceptable salt thereof with other arbitrary medicinal ingredient(s). Furthermore, these pharmaceutical preparations are prepared by mixing the active ingredient(s) with one or more pharmaceutically acceptable carrier(s) and then employing any method well-known in the technical field of pharmaceutics.

As for administration routes, it is preferred to select the most effective route of administration. Examples of the administration routes include oral administration or parenteral administration such as intravenous administration and the like. Application for stents is also possible.

As for the dosage form, for example, tablets, injections or the like are included. Examples of the dosage form also include drug-eluting stents comprising stents coated with a medicine.

For example, the tablet suitable for oral administration can be prepared with, for example, excipients such as lactose and mannitol; disintegrants such as starch; lubricants such as magnesium stearate; binders such as hydroxypropylcellulose; surfactants such as a fatty acid ester; plasticizers such as glycerol; and the like.

Preparations suitable for parenteral administration preferably comprise a sterilized aqueous preparation containing the active compound and being isotonic to blood of a recipient. For example, when an injection is prepared, a solution for injection is prepared by using a carrier consisting of a salt solution, glucose solution, a mixture of salt solution and glucose solution, or the like.

Also in these parenteral preparations, one or more kinds of auxiliary components selected from excipients, disintegrants, lubricants, binders, surfactants, plasticizers which are exemplified for the oral administration, diluents, preservatives, flavors and the like may be added.

Compound (0), (00) or (IV), or a pharmaceutically acceptable salt thereof is generally administered systemically or locally in the form of an oral or parenteral preparation when used for the aforementioned purpose. The dose and the frequency of administration may vary depending on the administration form, the age and body weight of a patient, nature and severity of the condition to be treated, and the like. When oral administration is performed, generally 0.01 to 1,000 mg/kg, preferably 0.05 to 500 mg/kg per single administration for an adult may be administered once a day or a few times a day, or once every several days to 1 or 2 weeks. When parenteral administration such as intravenous administration is performed, 0.001 to 1,000 mg/kg, preferably 0.01 to 300 mg/kg, per single administration for an adult may be administered once a day or a few times a day, or once every several days to 1 to 3 weeks. Examples of the administration method also include rapid intravenous injection, continuous intravenous administration for 1 to 24 hours a day, and the like. However, the dose and the frequency of administration may vary depending on the aforementioned various conditions and the like.

EXAMPLES

The present invention will be explained in detail with reference to the following examples and reference examples.

The spectra of proton nuclear magnetic resonance ($^1$H NMR) used in Examples were measured at 270 or 300 MHz, and exchangeable hydrogen may not always be clearly observed depending on the compound and the measurement conditions. For the descriptions of the multiplicity of signals, those generally applied are used, and the symbol "br" represents an apparent broad signal.

Example 1

Tablets (Compound 3)

Tablets having the following composition are prepared in a conventional manner. Compound 3 (40 g), lactose (286.8 g) and potato starch (60 g) are mixed, and 10% aqueous solution of hydroxypropylcellulose (120 g) is added to the mixture. Resulting mixture is kneaded, granulated and dried in a conventional manner, and then the granules are sized to obtain granules for tablet pressing. Magnesium stearate (1.2 g) is added to the granules for tablet pressing and mixed. Tablet formation is performed with a compressing machine having a punch of 8 mm a diameter (Kikusui, RT-15) to obtain tablets (containing 20 mg/tablet of active ingredient).

TABLE 13

| Formulation | |
|---|---|
| Compound 3 | 20 mg |
| Lactose | 143.4 mg |
| Potato starch | 30 mg |

TABLE 13-continued

| Formulation | |
|---|---|
| Hydroxypropylcellulose | 6 mg |
| Magnesium stearate | 0.6 mg |
| | 200 mg |

Example 2

Tablets (Compound 4)

Tablets having the following composition are prepared in a conventional manner. Compound 4 (40 g), lactose (286.8 g) and potato starch (60 g) are mixed, and 10% aqueous solution of hydroxypropylcellulose (120 g) is added to the mixture. Resulting mixture is kneaded, granulated and dried in a conventional manner, and then the granules are sized to obtain granules for tablet pressing. Magnesium stearate (1.2 g) is added to the granules for tablet pressing and mixed. Tablet formation is performed with a compressing machine having a punch of 8 mm a diameter (Kikusui, RT-15) to obtain tablets (containing 20 mg/tablet of active ingredient).

TABLE 14

| Formulation | |
|---|---|
| Compound 4 | 20 mg |
| Lactose | 143.4 mg |
| Potato starch | 30 mg |
| Hydroxypropylcellulose | 6 mg |
| Magnesium stearate | 0.6 mg |
| | 200 mg |

Example 3

Tablets (Compound 7)

Tablets having the following composition are prepared in a conventional manner. Compound 7 (40 g), lactose (286.8 g) and potato starch (60 g) are mixed, and 10% aqueous solution of hydroxypropylcellulose (120 g) is added to the mixture. Resulting mixture is kneaded, granulated and dried in a conventional manner, and then the granules are sized to obtain granules for tablet pressing. Magnesium stearate (1.2 g) is added to the granules for tablet pressing and mixed. Tablet formation is performed with a compressing machine having a punch of 8 mm a diameter (Kikusui, RT-15) to obtain tablets (containing 20 mg/tablet of active ingredient).

TABLE 15

| Formulation | |
|---|---|
| Compound 7 | 20 mg |
| Lactose | 143.4 mg |
| Potato starch | 30 mg |
| Hydroxypropylcellulose | 6 mg |
| Magnesium stearate | 0.6 mg |
| | 200 mg |

Example 4

Injection (Compound 3)

Injection having the following composition is prepared in a conventional manner. Compound 3 (1 g) and D-mannitol (5 g) are added to distilled water for injection and mixed, and hydrochloric acid and aqueous sodium hydroxide are added to the mixture to adjust to pH 7, and then the total volume is made 1000 mL with distilled water for injection. The resulting mixture is aseptically filled in glass vials in a volume of 2 mL each to obtain injection (containing 2 mg/vial of the active ingredient).

TABLE 16

| Formulation | |
| --- | --- |
| Compound 3 | 2 mg |
| D-Mannitol | 10 mg |
| Hydrochloric acid | Optimum amount |
| Aqueous sodium hydroxide | Optimum amount |
| Distilled water for injection | Optimum amount |
| | 2.00 mL |

Example 5

Injection (Compound 9)

Injection having the following composition is prepared in a conventional manner. Compound 9 (1 g) and D-mannitol (5 g) are added to distilled water for injection and mixed, and hydrochloric acid and aqueous sodium hydroxide are added to the mixture to adjust to pH 7, and then the total volume is made 1000 mL with distilled water for injection. The resulting mixture is aseptically filled in glass vials in a volume of 2 mL each to obtain injection (containing 2 mg/vial of the active ingredient).

TABLE 17

| Formulation | |
| --- | --- |
| Compound 9 | 2 mg |
| D-Mannitol | 10 mg |
| Hydrochloric acid | Optimum amount |
| Aqueous sodium hydroxide | Optimum amount |
| Distilled water for injection | Optimum amount |
| | 2.00 mL |

Example 6

Injection (Compound 12)

Injection having the following composition is prepared in a conventional manner. Compound 12 (1 g) and D-mannitol (5 g) are added to distilled water for injection and mixed, and hydrochloric acid and aqueous sodium hydroxide are added to the mixture to adjust to pH 7, and then the total volume is made 1000 mL with distilled water for injection. The resulting mixture is aseptically filled in glass vials in a volume of 2 mL each to obtain injection (containing 2 mg/vial of the active ingredient).

TABLE 18

| Formulation | |
| --- | --- |
| Compound 12 | 2 mg |
| D-Mannitol | 10 mg |
| Hydrochloric acid | Optimum amount |
| Aqueous sodium hydroxide | Optimum amount |
| Distilled water for injection | Optimum amount |
| | 2.00 mL |

Example 7

Tablets (Compound a)

Tablets having the following composition are prepared in a conventional manner. Compound a (40 g), lactose (286.8 g) and potato starch (60 g) are mixed, and 10% aqueous solution of hydroxypropylcellulose (120 g) is added to the mixture. Resulting mixture is kneaded, granulated and dried in a conventional manner, and then the granules are sized to obtain granules for tablet pressing. Magnesium stearate (1.2 g) is added to the granules for tablet pressing and mixed. Tablet formation is performed with a compressing machine having a punch of 8 mm a diameter (Kikusui, RT-15) to obtain tablets (containing 20 mg/tablet of active ingredient).

TABLE 19

| Formulation | |
| --- | --- |
| Compound a | 20 mg |
| Lactose | 143.4 mg |
| Potato starch | 30 mg |
| Hydroxypropylcellulose | 6 mg |
| Magnesium stearate | 0.6 mg |
| | 200 mg |

Example 8

Tablets (Compound d)

Tablets having the following composition are prepared in a conventional manner. Compound d (40 g), lactose (286.8 g) and potato starch (60 g) are mixed, and 10% aqueous solution of hydroxypropylcellulose (120 g) is added to the mixture. Resulting mixture is kneaded, granulated and dried in a conventional manner, and then the granules are sized to obtain granules for tablet pressing. Magnesium stearate (1.2 g) is added to the granules for tablet pressing and mixed. Tablet formation is performed with a compressing machine having a punch of 8 mm a diameter (Kikusui, RT-15) to obtain tablets (containing 20 mg/tablet of active ingredient).

TABLE 20

| Formulation | |
| --- | --- |
| Compound d | 20 mg |
| Lactose | 143.4 mg |
| Potato starch | 30 mg |
| Hydroxypropylcellulose | 6 mg |
| Magnesium stearate | 0.6 mg |
| | 200 mg |

Example 9

Tablets (Compound e)

Tablets having the following composition are prepared in a conventional manner. Compound e (40 g), lactose (286.8 g) and potato starch (60 g) are mixed, and 10% aqueous solution of hydroxypropylcellulose (120 g) is added to the mixture. Resulting mixture is kneaded, granulated and dried in a conventional manner, and then the granules are sized to obtain granules for tablet pressing. Magnesium stearate (1.2 g) is added to the granules for tablet pressing and mixed. Tablet formation is performed with a compressing machine having a punch of 8 mm a diameter (Kikusui, RT-15) to obtain tablets (containing 20 mg/tablet of active ingredient).

TABLE 21

| Formulation | |
| --- | --- |
| Compound e | 20 mg |
| Lactose | 143.4 mg |
| Potato starch | 30 mg |
| Hydroxypropylcellulose | 6 mg |
| Magnesium stearate | 0.6 mg |
| | 200 mg |

Example 10

Tablets (Compound l)

Tablets having the following composition are prepared in a conventional manner. Compound 1 (40 g), lactose (286.8 g) and potato starch (60 g) are mixed, and 10% aqueous solution of hydroxypropylcellulose (120 g) is added to the mixture. Resulting mixture is kneaded, granulated and dried in a conventional manner, and then the granules are sized to obtain granules for tablet pressing. Magnesium stearate (1.2 g) is added to the granules for tablet pressing and mixed. Tablet formation is performed with a compressing machine having a punch of 8 mm a diameter (Kikusui, RT-15) to obtain tablets (containing 20 mg/tablet of active ingredient).

TABLE 22

| Formulation | |
| --- | --- |
| Compound l | 20 mg |
| Lactose | 143.4 mg |
| Potato starch | 30 mg |
| Hydroxypropylcellulose | 6 mg |
| Magnesium stearate | 0.6 mg |
| | 200 mg |

Example 11

Tablets (Compound m)

Tablets having the following composition are prepared in a conventional manner. Compound m (40 g), lactose (286.8 g) and potato starch (60 g) are mixed, and 10% aqueous solution of hydroxypropylcellulose (120 g) is added to the mixture. Resulting mixture is kneaded, granulated and dried in a conventional manner, and then the granules are sized to obtain granules for tablet pressing. Magnesium stearate (1.2 g) is added to the granules for tablet pressing and mixed. Tablet formation is performed with a compressing machine having a punch of 8 mm a diameter (Kikusui, RT-15) to obtain tablets (containing 20 mg/tablet of active ingredient).

TABLE 23

| Formulation | |
| --- | --- |
| Compound m | 20 mg |
| Lactose | 143.4 mg |
| Potato starch | 30 mg |
| Hydroxypropylcellulose | 6 mg |
| Magnesium stearate | 0.6 mg |
| | 200 mg |

Example 12

Injection (Compound a)

Injection having the following composition is prepared in a conventional manner. Compound a (1 g) and D-mannitol (5 g) are added to distilled water for injection and mixed, and hydrochloric acid and aqueous sodium hydroxide are added to the mixture to adjust to pH 7, and then the total volume is made 1000 mL with distilled water for injection. The resulting mixture is aseptically filled in glass vials in a volume of 2 mL each to obtain injection (containing 2 mg/vial of the active ingredient).

TABLE 24

| Formulation | |
| --- | --- |
| Compound a | 2 mg |
| D-Mannitol | 10 mg |
| Hydrochloric acid | Optimum amount |
| Aqueous sodium hydroxide | Optimum amount |
| Distilled water for injection | Optimum amount |
| | 2.00 mL |

Example 13

Injection (Compound l)

Injection having the following composition is prepared in a conventional manner. Compound 1 (1 g) and D-mannitol (5 g) are added to distilled water for injection and mixed, and hydrochloric acid and aqueous sodium hydroxide are added to the mixture to adjust the mixture to pH 7, and then the total volume is made 1000 mL with distilled water for injection. The resulting mixture is aseptically filled in glass vials in a volume of 2 mL each to obtain injection (containing 2 mg/vial of the active ingredient).

TABLE 25

| Formulation | |
| --- | --- |
| Compound l | 2 mg |
| D-Mannitol | 10 mg |
| Hydrochloric acid | Optimum amount |
| Aqueous sodium hydroxide | Optimum amount |
| Distilled water for injection | Optimum amount |
| | 2.00 mL |

Example 14

Injection (Compound m)

Injection having the following composition is prepared in a conventional manner. Compound m (1 g) and D-mannitol (5 g) are added to distilled water for injection and mixed, and hydrochloric acid and aqueous sodium hydroxide are added to the mixture to adjust to pH 7, and then the total volume is made 1000 mL with distilled water for injection. The resulting mixture is aseptically filled in glass vials in a volume of 2 mL each to obtain injection (containing 2 mg/vial of the active ingredient).

TABLE 26

| Formulation | |
| --- | --- |
| Compound m | 2 mg |
| D-Mannitol | 10 mg |
| Hydrochloric acid | Optimum amount |
| Aqueous sodium hydroxide | Optimum amount |
| Distilled water for injection | Optimum amount 2.00 mL |

Examples 15 to 53

Compounds 100 to 138

Compounds 100 to 138 were synthesized in the same manner as that of Reference Example 47 by subjecting Compound 10 {N-[4-(2,2-dimethylpropionyl)-5-ethenesulfonylaminomethyl-5-phenyl-4,5-dihydro-1,3,4-thiadiazol-2-yl]-2,2-dimethylpropanamide} obtained in Reference Example 10, N-[4-acetyl-5-ethenesulfonylaminomethyl-5-phenyl-4,5-dihydro-1,3,4-thiadiazol-2-yl]-2,2-dimethylpropanamide, or N-{2-[3-acetyl-5-(2-oxopiperidino)-2-phenyl-2,3-dihydro-1,3,4-thiadiazol-2-yl]methyl}vinylsulfonamide obtained by the method described in WO2004/092147 and a corresponding sulfanyl compound to the Michael addition reaction, respectively, and then subjecting the resultant to a reaction for removal of protective group or the like if necessary.

TABLE 27

| Ex. No. | Compound No. | APCI-MS m/z | Yield % |
| --- | --- | --- | --- |
| 15 | 100 | — | 57 |
| 16 | 101 | 526 (M + 1)⁺ | — |
| 17 | 102 | 552 (M + 1)⁺ | — |
| 18 | 103 | 554 (M + 1)⁺ | — |
| 19 | 104 | 570 (M + 1)⁺ | — |
| 20 | 105 | 567 (M + 1)⁺ | — |
| 21 | 106 | 610 (M + 1)⁺ | — |
| 22 | 107 | 566 (M + 1)⁺ | — |
| 23 | 108 | 554 (M + 1)⁺ | 79 |
| 24 | 109 | 535 (M + 1)⁺ | 77 |
| 25 | 110 | 535 (M + 1)⁺ | 85 |
| 26 | 111 | 536 (M + 1)⁺ | 85 |
| 27 | 112 | 536 (M + 1)⁺ | 54 |
| 28 | 113 | 536 (M + 1)⁺ | 22 |
| 29 | 114 | 550 (M + 1)⁺ | 57 |
| 30 | 115 | 494 (M + 1)⁺ | 16 |
| 31 | 116 | 492 (M + 1)⁺ | 5 |
| 32 | 117 | 538 (M + 1)⁺ | 72 |
| 33 | 118 | 536 (M + 1)⁺ | 36 |
| 34 | 119 | 554 (M + 1)⁺ | 81 |
| 35 | 120 | 554 (M + 1)⁺ | 88 |
| 36 | 121 | 578 (M + 1)⁺ | 92 |
| 37 | 122 | 568 (M + 1)⁺ | 46 |
| 38 | 123 | 550 (M + 1)⁺ | 43 |
| 39 | 124 | 567 (M + 1)⁺ | 70 |
| 40 | 125 | 598 (M + 1)⁺ | 68 |
| 41 | 126 | 552 (M + 1)⁺ | 88 |
| 42 | 127 | 564 (M + 1)⁺ | 17 |
| 43 | 128 | 582 (M + 1)⁺ | 89 |
| 44 | 129 | 494 (M + 1)⁺ | 10 |
| 45 | 130 | 497 (M + 1)⁺ | 83 |
| 46 | 131 | 593 (M + 1)⁺ | 79 |
| 47 | 132 | 612 (M + 1)⁺ | 36 |
| 48 | 133 | 553 (M + 1)⁺ | 75 |
| 49 | 134 | 537 (M + 1)⁺ | 64 |
| 50 | 135 | 552 (M + 1)⁺ | 33 |
| 51 | 136 | 566 M + 1)⁺ | 36 |
| 52 | 137 | 551 (M + 1)⁺ | 34 |
| 53 | 138 | 526 (M + 1)⁺ | 28 |

Example 54

Compound 139

Compound 139 was synthesized according to the method described in WO2004/092147.
Compound 139 APCI-MS m/z: 628 (M+1)⁺.

Reference Examples 1 to 13

Compounds 1 to 13

Compounds 1 to 13 were synthesized according to the method described in WO2003/051854 or WO2004/111024, respectively.

Reference Examples 14 to 19

Compounds 14 to 19

Compounds 14 to 19 were synthesized according to the method described in WO2003/051854 or WO2004/111024, respectively.

Reference Examples 20

Compound a (−)-N-[4-(2,2-Dimethylpropionyl)-5-(2-methanesulfonylaminoethyl)-5-phenyl-4,5-dihydro-1,3,4-thiadiazol-2-yl]-2,2-dimethylpropanamide Step 1: (S)-(+)-2-Phenylpropionic acid (4.88 g, 32.5 mmol) was dissolved in dichloromethane (20 mL), and thionyl chloride (30 mL) was added, then the mixture was stirred at room temperature for 4 hours. The mixture was concentrated under reduced pressure, and then the resulting residue was dissolved in dichloromethane (10 mL) (dichloromethane solution). Next, N-{2-[5-amino-3-(2,2-dimethylpropionyl)-2-phenyl-2,3-dihydro-1,3,4-thiadiazol-2-yl]ethyl}methanesulfonamide (4.93 g, 12.8 mmol) obtained according to the method described in WO2003/051854 was dissolved in dichloromethane (15 mL) and pyridine (3.1 mL), and the aforementioned dichloromethane solution was added. After the mixture was stirred at room temperature for 1.5 hours, water was added, and the mixture was extracted with chloroform. The organic layer was washed with 1 mol/L hydrochloric acid, water, and saturated brine, dried over anhydrous sodium sulfate, and concentrated under reduced pressure. To the residue were added chloroform (50 mL) and diisopropyl ether (10 mL), and the mixture was stirred. The deposited powder was collected by filtration, and purified by silica gel column chromatography (chloroform/acetone/n-hexane/ethyl acetate=9/1/1/1, 9/1/6.5/3.5, 9/1/7/3, and then 9/1/5/5) respectively to give one diastereomer of N-[4-(2,2-dimethylpropionyl)-5-(2-methanesulfonylaminoethyl)-5-phenyl-4,5-dihydro-1,3,4-thiadiazol-2-yl]-2-phenylpropanamide (2.48 g, 38%) as a fraction eluted first and another diastereomer of N-[4-(2,2-dimethylpropionyl)-5-(2-methanesulfonylaminoethyl)-5-phenyl-4,5-dihydro-1,3,4-thiadiazol-2-yl]-2-phenylpropanamide (2.80 g, 43%) as a fraction eluted later.

One diastereomer of N-[4-(2,2-dimethylpropionyl)-5-(2-methanesulfonylaminoethyl)-5-phenyl-4,5-dihydro-1,3,4-thiadiazol-2-yl]-2-phenylpropanamide eluted first: $^1$H NMR (270 MHz, CDCl$_3$) δ (ppm): 1.26 (s, 9H), 1.53 (d, J=7.1 Hz, 3H), 2.60 (m, 1H), 2.93 (s, 3H), 3.20 (m, 1H), 3.36 (m, 1H), 3.57 (m, 1H), 3.67 (q, J=7.1 Hz, 1H), 4.45 (br t, 1H), 7.20-7.49 (m, 10H), 7.75 (s, 1H).

APCI-MS m/z: 515 (M−H)$^-$.

Another diastereomer of N-[4-(2,2-dimethylpropionyl)-5-(2-methanesulfonylamino-ethyl)-5-phenyl-4,5-dihydro-1,3,4-thiadiazol-2-yl]-2-phenylpropanamide eluted later:

$^1$H NMR (270 MHz, CDCl$_3$) δ (ppm): 1.25 (s, 9H), 1.51 (d, J=7.1 Hz, 3H), 2.56 (m, 1H), 2.96 (s, 3H), 3.23 (m, 1H), 3.37 (m, 1H), 3.62 (m, 1H), 3.63 (q, J=7.1 Hz, 1H), 4.67 (br t, J=5.9 Hz, 1H), 7.17-7.52 (m, 10H), 7.99 (s, 1H).

APCI-MS m/z: 515 (M−H)$^-$.

Step 2: The one diastereomer of N-[4-(2,2-dimethylpropionyl)-5-(2-methanesulfonyl-aminoethyl)-5-phenyl-4,5-dihydro-1,3,4-thiadiazol-2-yl]-2-phenylpropanamide (2.28 g, 4.41 mmol) eluted first obtained in Step 1 mentioned above was dissolved in methanol (100 mL), and cerium chloride heptahydrate (1.64 g, 4.41 mmol) and sodium borohydride (6.68 g, 0.176 mmol) were added, then the mixture was stirred at room temperature for 40 minutes. The mixture was further stirred at room temperature for 2 hours with adding sodium borohydride (20.04 g, 0.5297 mmol) and methanol (250 mL), divided into 3 portions, respectively, to the mixture, and then concentrated under reduced pressure. To the residue were added ethyl acetate and 1 mol/L hydrochloric acid, and the mixture was extracted with ethyl acetate. The organic layer was washed with saturated brine, dried over anhydrous sodium sulfate, and concentrated under reduced pressure. The residue was purified by silica gel column chromatography (chloroform/acetone/n-hexane/ethyl acetate=9/1/7/3→9/1/5/5). This procedure was repeatedly performed, and the resulting crude product (0.802 g, 2.09 mmol in total) was dissolved in a mixed solvent of ethanol (20 mL) and n-hexane (200 mL). Then the deposited solid was filtered off, and the filtrate was concentrated to give optically active N-{2-[5-amino-3-(2,2-dimethylpropionyl)-2-phenyl-2,3-dihydro-1,3,4-thiadiazol-2-yl]ethyl}methanesulfonamide (0.647 g, 23%).

Step 3: The optically active N-{2-[5-amino-3-(2,2-dimethylpropionyl)-2-phenyl-2,3-dihydro-1,3,4-thiadiazol-2-yl]ethyl}methanesulfonamide (90 mg, 0.23 mmol) obtained in Step 2 mentioned above was dissolved in dichloromethane (4 mL), and pyridine (0.224 mL, 2.77 mmol) and trimethylacetyl chloride (0.288 mL, 2.33 mmol) were added, then the mixture was stirred at room temperature for 3.5 hours. To the reaction mixture were added water and 1 mol/L hydrochloric acid, and the mixture was extracted with ethyl acetate. The organic layer was washed with saturated brine, dried over anhydrous sodium sulfate, and concentrated under reduced pressure. After the residue was purified by silica gel column chromatography (n-hexane/ethyl acetate=3/1→2/1), to the resulting syrup were added ethanol and then n-hexane. The supernatant was separated by decantation to give the deposited solid. Subsequently, to the solid was added diisopropyl ether, and the mixture was stirred to pulverize the resulting solid and thereby give Compound a {(−)-N-[4-(2,2-dimethylpropionyl)-5-(2-methanesulfonylaminoethyl)-5-phenyl-4,5-dihydro-1,3,4-thiadiazol-2-yl]-2,2-dimethylpropanamide} (60 mg, 55%).

$^1$H NMR (300 MHz, CDCl$_3$) δ (ppm): 1.30 (s, 9H), 1.34 (s, 9H), 2.56-2.65 (m, 1H), 2.94 (s, 3H), 3.21-3.44 (m, 2H), 3.58-3.70 (m, 1H), 4.45 (br s, 1H), 7.28-7.37 (m, 5H), 7.97 (br s, 1H).

APCI-MS m/z: 467 (M−1)$^-$.

Melting point: 204.0-206.0° C.

Specific rotation: A solution of the resulting compound in methanol gave a negative value as a specific rotation for sodium D line (wavelength: 589.3 nm) at 20° C.

Reference Example 21

Compound b (−)-N-[5-(2-Methanesulfonylaminoethyl)-5-phenyl-4-propionyl-4,5-dihydro-1,3,4-thiadiazol-2-yl]-2,2-dimethylpropanamide Step 1: In the same manner as that in Step 1 of Example 20, from N-[2-(5-amino-2-phenyl-3-propionyl-2,3-dihydro-1,3,4-thiadiazol-2-yl)ethyl]methanesulfonamide (10.7 g, 30.0 mmol) obtained according to the method described in WO2003/051854, and (R)-(−)-2-phenylpropionyl chloride prepared from (R)-(−)-2-phenylpropionic acid (10.5 g, 69.9 mmol) and thionyl chloride, N-[5-(2-methanesulfonylaminoethyl)-5-phenyl-4-propionyl-4,5-dihydro-1,3,4-thiadiazol-2-yl]-2-phenylpropanamide was obtained as a diastereomer mixture (13.3 g, 92%). A part of this mixture (3.89 g, 7.96 mmol) was purified by silica gel column chromatography (chloroform/acetonitrile/n-hexane/ethyl acetate=9/1/1/1) to give one diastereomer of N-[5-(2-methanesulfonylaminoethyl)-5-phenyl-4-propionyl-4,5-dihydro-1,3,4-thiadiazol-2-yl]-2-phenylpropanamide (0.861 g, 22%) as a fraction that eluted later, and another diastereomer of N-[5-(2-methanesulfonylaminoethyl)-5-phenyl-4-propionyl-4,5-dihydro-1,3,4-thiadiazol-2-yl]-2-phenylpropanamide (0.802 g, 20%) as a fraction that eluted first.

Step 2: In the same manner as that in Step 2 of Reference Example 20, from the one diastereomer of N-[5-(2-methanesulfonylaminoethyl)-5-phenyl-4-propionyl-4,5-dihydro-1,3,4-thiadiazol-2-yl]-2-phenylpropanamide (4.41 g, 9.03 mmol) eluted later obtained in Step 1 mentioned above, cerium chloride heptahydrate (3.37 g, 9.05 mmol) and sodium borohydride (3.42 g, 90.5 mmol), optically active N-[2-(5-amino-2-phenyl-3-propionyl-2,3-dihydro-1,3,4-thiadiazol-2-yl)ethyl]methanesulfonamide (2.16 g, 67%) was obtained.

Step 3: In the same manner as that in Step 3 of Example 20, from the optically active N-[2-(5-amino-2-phenyl-3-propionyl-2,3-dihydro-1,3,4-thiadiazol-2-yl)ethyl]methane-sulfonamide (0.0480 g, 0.135 mmol) obtained in Step 2 mentioned above, pyridine (32.7 μL, 0.405 mmol) and trimethylacetyl chloride (41.7 μL, 0.338 mmol), Compound b {(−)-N-[5-(2-methanesulfonylaminoethyl)-5-phenyl-4-propionyl-4,5-dihydro-1,3,4-thia-diazol-2-yl]-2,2-dimethylpropanamide} (0.0504 g, 84%) was obtained.

¹H NMR (270 MHz, CDCl₃) δ (ppm): 1.13 (t, J=6.0 Hz, 3H), 1.28 (s, 9H), 2.66 (m, 3H), 2.97 (s, 3H), 3.35 (m, 2H), 3.61 (m, 1H), 4.58 (br s, 1H), 7.32 (m, 5H), 8.08 (br s, 1H).

APCI-MS m/z: 441 (M+1)⁺.

Melting point: 107.0-110.0° C.

Specific rotation: A solution of the resulting compound in methanol gave a negative value as a specific rotation for sodium D line (wavelength: 589.3 nm) at 20° C.

Reference Example 22

Compound c (−)-N-{2-[3-(2,2-Dimethylpropionyl)-5-(2-oxopyrrolidin-1-yl)-2-phenyl-2,3-dihydro-1,3,4-thiadiazol-2-yl]ethyl}methanesulfonamide The optically active N-{2-[5-amino-3-(2,2-dimethylpropionyl)-2-phenyl-2,3-dihydro-1,3,4-thiadiazol-2-yl]ethyl}methanesulfonamide (0.647 g, 1.68 mmol) obtained in Step 2 of Reference Example 20 was dissolved in dichloromethane (25 mL), and pyridine (0.41 mL, 5.1 mmol) and 4-bromobutyryl chloride (0.49 mL, 4.2 mmol) were added, then the mixture was stirred at room temperature for 2 hours. To the reaction mixture was added water, and the mixture was extracted with chloroform. The organic layer was washed with 0.5 mol/L hydrochloric acid and brine, dried over anhydrous sodium sulfate, and concentrated under reduced pressure. The residue was dissolved in dimethyl sulfoxide (DMSO, 6 mL), and sodium acetate (0.331 g, 4.04 mmol) was added, then the mixture was heated to 100° C. over 14 minutes with stirring. After cooling, to the mixture was added water, and the mixture was extracted with ethyl acetate. The organic layer was washed with brine, dried over anhydrous sodium sulfate, and concentrated under reduced pressure. The residue was purified by flash column chromatography (n-hexane/ethyl acetate=3/1→1/1), and recrystallized from acetone to give Compound c {(−)-N-{2-[3-(2,2-dimethylpropionyl)-5-(2-oxopyrrolidin-1-yl) -2-phenyl-2,3-dihydro-1,3,4-thiadiazol-2-yl]ethyl}methanesulfonamide} (0.649 g, 85%).

¹H NMR (270 MHz, CDCl₃) δ (ppm): 1.34 (s, 9H), 2.23 (m, 2H), 2.56 (m, 2H), 2.61 (m, 1H), 2.97 (s, 3H), 3.27 (m, 1H), 3.40 (m, 1H), 3.63 (m, 1H), 3.98 (m, 2H), 4.01 (br t, J=3.5 Hz, 1H), 7.20-7.37 (m, 5H).

APCI-MS m/z: 453 (M+1)⁺.

Melting point: 107.0-110.0° C.

Specific rotation: A solution of the resulting compound in methanol gave a negative value as a specific rotation for sodium D line (wavelength: 589.3 nm) at 20° C.

Reference Example 23

Compound d (−)-N-[4-Isobutyryl-5-(2-methanesulfonylaminoethyl)-5-phenyl-4,5-dihydro-1,3,4-thia-diazol-2-yl]-2,2-dimethylpropanamide Step 1: N-[4-Isobutyryl-5-(2-methanesulfonylaminoethyl)-5-phenyl-4,5-dihydro-1,3,4-thiadiazol-2-yl]-2,2-dimethylpropanamide (2.32 g, 5.10 mmol) obtained according to the method described in WO2003/051854 was subjected to preparative high performance liquid chromatography (HPLC) [column: CHIRALPAK AD (Daicel Chemical Industries, Ltd.], elution solvent: 12% isopropyl alcohol/n-hexane, flow rate: 6 mL/minute, column temperature: 25° C.] to give fractions for retention times of 10.2 minutes and 11.2 minutes. Among them, the fraction of 11.2 minutes was concentrated, and the residue was recrystallized from n-pentane and ethanol to give Compound d {(−)-N-[4-iso-butyryl-5-(2-methanesulfonylaminoethyl)-5-phenyl-4,5-dihydro-1,3,4-thiadiazol-2-yl]-2,2-dimethylpropanamide} (0.707 g, 30%) as white crystals.

¹H NMR (270 MHz, CDCl₃) δ (ppm): 1.15 (2 x d, J=7.0 Hz, 6H), 1.29 (s, 9H), 2.57-2.67 (m, 1H), 2.96 (s, 3H), 3.23-3.44 (m, 3H), 3.37-3.68 (m, 1H), 4.46 (br s, 1H), 7.25-7.38 (m, 5H), 8.00 (br s, 1H).

APCI-MS m/z: 453 (M−1)⁻.

Melting point: 162.0-164.0° C.

Specific rotation: A solution of the resulting compound in methanol gave a negative value as a specific rotation for sodium D line (wavelength: 589.3 nm) at 20° C.

Reference Example 24

Compound e (−)-N-{2-[5-(2-Oxopyrrolidin-1-yl)-2-phenyl-3-propionyl-2,3-dihydro-1,3,4-thiadiazol-2-yl]ethyl}methanesulfonamide The optically active N-[2-(5-amino-2-phenyl-3-propionyl-2,3-dihydro-1,3,4-thiadiazol-2-yl)ethyl]methanesulfonamide (1.01 g, 2.83 mmol) obtained in Step 2 of Reference Example 21 and pyridine (330 µL, 4.08 mmol) were dissolved in dichloromethane (40 mL), and 4-bromobutyryl chloride (390 µL, 3.40 mmol) was added at 0° C., then the mixture was stirred at room temperature for 2 hours. To the mixture was added 1 mol/L hydrochloric, and the mixture was extracted with chloroform. The organic layer was dried over anhydrous sodium sulfate, and concentrated under reduced pressure. To the residue were added DMSO (10 mL) and sodium acetate (560 mg, 6.83 mmol), and the mixture was stirred at 100° C. for 5 minutes. After cooling, water and 1 mol/L hydrochloric acid were added, and the mixture was extracted with ethyl acetate. The organic layer was dried over anhydrous sodium sulfate, and concentrated under reduced pressure. The residue was purified by silica gel column chromatography (chloroform/methanol=20/1) to give Compound e {(−)-N-{2-[5-(2-oxopyrrolidin-1-yl)-2-phenyl-3-propionyl-2,3-dihydro-1,3, 4-thiadiazol-2-yl]ethyl}-methanesulfonamide} (878 mg, 73%).

¹H NMR (270 MHz, CDCl₃) δ (ppm): 1.15 (t, J=6.6 Hz, 3H), 2.22 (m, 2H), 2.55-2.67 (m, 3H), 2.94 (s, 3H), 3.31-3.47 (m, 4H), 3.61 (m, 1H), 3.91-3.98 (m, 2H), 5.0 (br s, 1H), 7.20-7.35 (m, 5H).

APCI-MS m/z: 423 (M−1)⁻.

Melting point: 188.0-191.0° C.

Specific rotation: A solution of the resulting compound in methanol gave a negative value as a specific rotation for sodium D line (wavelength: 589.3 nm) at 20° C.

Reference Example 25

Compound f (−)-N-[4-Acetyl-5-(2-methanesulfonylaminoethyl)-5-phenyl-4,5-dihydro-1,3,4-thiadiazol-2-yl]-2,2-dimethylpropanamide Step 1: Methanesulfonamide (0.476 g, 5.00 mmol) was dissolved in N,N-dimethyl-formamide (DMF, 10 mL), and 60% sodium hydride (0.275 g, 5.00 mmol) was added at 0° C., then the mixture was stirred at the same temperature for 20 minutes. Subsequently, to the mixture was added 3-chloropropiophenone (843 mg, 5.00 mol), and the mixture was stirred at the same temperature for 2 hours, and then further stirred at room temperature for 15 hours. To the mixture was added water, and the mixture was extracted with ethyl acetate. The organic layer was washed with brine, dried over anhydrous sodium sulfate, and concentrated under reduced pressure. The residue was purified by silica gel column chromatography (chloroform/methanol=20/1) to give N-methanesulfonyl-3-aminopropiophenone (240 mg, 21%).

Subsequently, in the same manner as that of the method described in WO2003/051854, N-methanesulfonyl-3-aminopropiophenone=thiosemicarbazone (219 mg, 45%) was obtained from N-methanesulfonyl-3-aminopropiophenone (388 mg, 1.71 mmol) obtained above and thiosemicarbazide (156 mg, 1.71 mmol).

Step 2: N-Methanesulfonyl-3-aminopropiophenone=thiosemicarbazone (9.83 g, 32.7 mmol) obtained in Step 1 mentioned above was dissolved in acetic anhydride (38 mL), and the solution was stirred at 130° C. for 10 minutes, and further stirred at 70° C. for 2 hours, and then at room temperature for 5 hours. The deposited solid was collected by filtration to give N-[4-acetyl-5-(2-methanesulfonylaminoethyl)-5-phenyl-4,5-dihydro-1,3,4-thiadiazol-2-yl]acetamide (11.3 g, 73%).

Step 3: In the same manner as that of the method described in WO2003/051854, from N-[4-acetyl-5-(2-methanesulfonylaminoethyl)-5-phenyl-4,5-dihydro-1,3,4-thiadiazol-2-yl]acetamide (5.22 g, 13.6 mmol) obtained in Step 2 mentioned above, sodium borohydride (5.14 g, 136 mmol), and cerium chloride heptahydrate (5.07 g, 13.6 mmol), N-[2-(3-acetyl-5-amino-2-phenyl-2,3-dihydro-1,3,4-thiadiazol-2-yl)ethyl]methane-sulfonamide was obtained.

Next, (R)-(−)-2-phenylpropionyl chloride prepared from (R)-(−)-2-phenylpropionic acid (4.65 g, 3.10 mmol) and thionyl chloride (30 mL), and N-[2-(3-acetyl-5-amino-2-phenyl-2,3-dihydro-1,3,4-thiadiazol-2-yl)ethyl]methane-sulfonamide obtained above were treated in pyridine (5.0 mL, 61.8 mmol) in the same manner as that in Step 1 of Example 20, and the resultant was purified by silica gel column chromatography (chloroform/n-hexane/ethyl acetate/methanol=20/3/2/1) to give one diastereomer of N-[4-acetyl-5-(2-methanesulfonylaminoethyl)-5-phenyl-4,5-dihydro-1,3,4-thiadiazol-2-yl]-2-phenylpropanamide (0.75 g, 12%) as a fraction eluted first, and another diastereomer of N-[4-acetyl-5-(2-methanesulfonylaminoethyl)-5-phenyl-4,5-dihydro-1,3,4-thiadiazol-2-yl]-2-phenylpropanamide (0.82 g, 13%) as a fraction eluted later.

Step 4: In the same manner as that in Step 2 of Reference Example 20, from another diastereomer of N-[4-acetyl-5-(2-methanesulfonylaminoethyl)-5-phenyl-4,5-dihydro-1,3,4-thiadiazol-2-yl]-2-phenylpropanamide (0.632 g, 1.33 mmol) eluted later obtained in Step 3 mentioned above, cerium chloride heptahydrate (0.496 g, 1.33 mmol) and sodium borohydride (0.503 g, 13.3 mmol), optically active N-[2-(3-acetyl-5-amino-2-phenyl-2,3-dihydro-1,3,4-thiadiazol-2-yl)ethyl]methanesulfonamide (232 mg, 51%) was obtained.

Step 5: In the same manner as that in Step 3 of Reference Example 20, from the optically active N-[2-(3-acetyl-5-amino-2-phenyl-2,3-dihydro-1,3,4-thiadiazol-2-yl)ethyl]-methanesulfonamide (0.0393 g, 0.115 mmol) obtained in Step 4 mentioned above, pyridine (44.7 μL, 0.552 mmol) and trimethylacetyl chloride (56.7 μL, 0.460 mmol), Compound f {(−)-N-[4-acetyl-5-(2-methanesulfonylaminoethyl)-5-phenyl-4,5-dihydro-1,3,4-thiadiazol-2-yl]-2,2-dimethylpropanamide} (0.0420 g, 86%) was obtained.

$^1$H NMR (270 MHz, CDCl$_3$) δ (ppm): 1.28 (s, 9H), 2.30 (s, 3H), 2.55-2.68 (m, 1H), 2.97 (s, 3H), 3.30-3.43 (m, 2H), 3.59-3.68 (m, 1H), 4.44 (br s, 1H), 7.27-7.39 (m, 5H), 8.00 (br s, 1H).

APCI-MS m/z: 425 (M−1)$^-$.

Melting point: 187.0-190.0° C.

Specific rotation: A solution of the resulting compound in methanol gave a negative value as a specific rotation for sodium D line (wavelength: 589.3 nm) at 20° C.

Reference Example 26

Compound g

N-{2-[3-Acetyl-5-(2-oxopyrrolidin-1-yl)-2-phenyl-2,3-dihydro-1,3,4-thiadiazol-2-yl]-ethyl}methanesulfonamide In the same manner as that in Reference Example 22, from the optically active N-[2-(3-acetyl-5-amino-2-phenyl-2,3-dihydro-1,3,4-thiadiazol-2-yl)ethyl]-methane-sulfonamide (0.0300 g, 0.0876 mmol) obtained in Step 4 of Reference Example 25, pyridine (33.6 μL, 0.420 mmol), 4-bromobutyryl chloride (40.6 μL, 0.350 mmol) and sodium acetate (0.0575 g, 0.701 mmol), Compound g {N-{2-[3-acetyl-5-(2-oxopyrrolidin-1-yl)-2-phenyl-2,3-dihydro-1,3,4-thiadiazol-2-yl]ethyl}methane-sulfonamide} (0.0301 g, 84%) was obtained.

$^1$H NMR (270 MHz, CDCl$_3$) δ (ppm): 2.15 (m, 2H), 2.33 (s, 3H), 2.50-2.67 (m, 3H), 2.97 (s, 3H), 3.31-3.44 (m, 2H), 3.60-3.65 (m, 1H), 3.87-3.97 (m, 2H), 4.46 (br s, 1H), 7.24-7.38 (m, 5H).

APCI-MS m/z: 409 (M−1)$^-$.

Melting point: 137.0-140.0° C.

Reference Example 27

Compound h (−)-N-{2-[3-Acetyl-5-(2-oxopiperidino)-2-phenyl-2,3-dihydro-1,3,4-thiadiazol-2-yl]ethyl}methanesulfonamide In the same manner as that in Reference Example 22, from the optically active N-[2-(3-acetyl-5-amino-2-phenyl-2,3-dihydro-1,3,4-thiadiazol-2-yl)ethyl]-methane-sulfonamide (0.0260 g, 0.0759 mmol) obtained in Step 4 of Reference Example 25, pyridine (29.3 μL, 0.365 mmol), 5-bromovaleryl chloride (40.7 μL, 0.304 mmol) and sodium acetate (0.0498 g, 0.607 mmol), Compound h {(−)-N-{2-[3-acetyl-5-(2-oxopiperidino)-2-phenyl-2,3-dihydro-1,3,4-thiadiazol-2-yl]ethyl}methanesulfonamide} (0.0241 g, 75%) was obtained.

$^1$H NMR (270 MHz, CDCl$_3$) δ (ppm): 1.82-1.98 (m, 4H), 2.33 (s, 3H), 2.52-2.62 (m, 3H), 2.95 (s, 3H), 3.27-3.38 (m, 2H), 3.59-3.70 (m, 1H), 3.84-3.92 (m, 2H), 4.62 (br s, 1H), 7.23-7.37 (m, 5H).

APCI-MS m/z: 423 (M−1)$^-$.

Melting point: 169.0-171.0° C.

Specific rotation: A solution of the resulting compound in methanol gave a negative value as a specific rotation for sodium D line (wavelength: 589.3 nm) at 20° C.

Reference Example 28

Compound i

N-{4-(2,2-Dimethylpropionyl)-5-[2-(2-ethylaminoethanesulfonylamino)-ethyl]-5-phenyl-4,5-dihydro-1,3,4-thiadiazol-2-yl}-2,2-dimethylpropanamide Step 1: Palladium(II) acetate (125 mg, 0.559 mmol) and triphenylphosphine (317 mg, 1.21 mmol) were dissolved in tetrahydrofuran (THF, 50 mL). To the resulting solution were added N-tert-butoxycarbonyl-β-alanine (2.07 g, 10.9 mmol), phenylboronic acid (1.61 g, 13.2 mmol), distilled water (0.477 mL, 26.5 mmol) and trimethylacetic anhydride (3.23 mL, 15.9 mmol), and the mixture was stirred at 60° C. for 24 hours. The mixture was filtered, saturated aqueous sodium hydrogencarbonate was added to the filtrate, and the mixture was extracted with ethyl acetate. The organic layer was washed with brine, dried over anhydrous sodium sulfate, and concentrated under reduced pressure. The residue was purified by silica gel column chromatography (hexane/ethyl acetate=9/1→4/1) to give (3-oxo-3-phenylpropyl)carbamic acid tert-butyl ester (1.85 g, 68%).

Step 2: (3-Oxo-3-phenylpropyl)carbamic acid tert-butyl ester (513 mg, 2.06 mmol) obtained in Step 1 mentioned above was dissolved in methanol (40 mL). To the resulting solution was added thiosemicarbazide hydrochloride (562 mg, 4.40 mmol), and the mixture was stirred at room temperature for 8 hours. To the mixture was added water, and the mixture was extracted with ethyl acetate. The organic layer was washed with brine, dried over anhydrous sodium sulfate, and concentrated under reduced pressure to give a pale yellow solid (513 mg). Apart of the resulting solid (198 mg) was dissolved in dichloromethane (10 mL). To the resulting solution were added pyridine (0.300 mL, 3.73 mmol) and trimethylacetyl chloride (0.415 mL, 3.37 mmol), and the mixture was stirred at room temperature for 22 hours. To the mixture was added saturated aqueous sodium hydrogencarbonate, and the mixture was further stirred at room temperature for 1 hour, and extracted with ethyl acetate. The organic layer was washed with brine, dried over anhydrous sodium sulfate, and concentrated under reduced pressure. The residue was purified by preparative silica gel thin layer chromatography (n-hexane/ethyl acetate=2/1) to give {2-[3-(2,2-dimethylpropionyl)-5-(2,2-dimethylpropionylamino)-2-phenyl-2,3-dihydro-1,3,4-thiadiazol-2-yl]ethyl}-carbamic acid tert-butyl ester (319 mg, 100%).

APCI-MS m/z: 491(M+H)$^+$.

Step 3: {2-[3-(2,2-Dimethylpropionyl)-5-(2,2-dimethylpropionylamino)-2-phenyl-2,3-dihydro-1,3,4-thiadiazol-2-yl]ethyl}carbamic acid tert-butyl ester (274 mg, 0.557 mmol) obtained in Step 2 mentioned above was dissolved in dichloromethane (10 mL). To the resulting solution was added trifluoroacetic acid (1.0 mL), and the mixture was stirred at room temperature for 3 hours, and then concentrated under reduced pressure. To the residue was added diisopropyl ether, and the mixture was stirred for 3 hours. The deposited white solid was collected by filtration to give trifluoroacetate of N-[5-(2-aminoethyl)-4-(2,2-dimethylpropionyl)-5-phenyl-4,5-dihydro-1,3,4-thiadiazol-2-yl]-2,2-dimethylpropanamide (252 mg, 90%).

APCI-MS m/z: 391(M+H)$^+$.

Step 4: The trifluoroacetate of N-[5-(2-aminoethyl)-4-(2,2-dimethylpropionyl)-5-phenyl-4,5-dihydro-1,3,4-thiadiazol-2-yl]-2,2-dimethylpropanamide (0.25 g, 0.53 mmol) obtained in Step 3 mentioned above was dissolved in methanol (5 mL), and the solution was loaded on a column filled with ion exchange silica gel [SCX (Varian, BONDESIL SCX 40 μM)]. After SCX was washed with methanol, a fraction eluted with a 1% hydrogen chloride—methanol solution was collected, and the fraction was concentrated under reduced pressure to give hydrochloride of N-[5-(2-aminoethyl)-4-(2,2-dimethylpropionyl)-5-phenyl-4,5-dihydro-1,3,4-thiadiazol-2-yl]-2,2-dimethyl-propanamide (0.19 g) as a white solid.

The hydrochloride obtained above was dissolved in dichloromethane (10 mL), and 2-chloroethanesulfonyl chloride (0.14 mL, 2.2 mmol) and triethylamine (0.62 mL, 4.6 mmol) were added at 0° C., then the mixture was stirred at the same temperature for 4 hours, and then at room temperature for 10 hours. To the mixture was added saturated aqueous sodium hydrogencarbonate, and the mixture was extracted with ethyl acetate. The organic layer was washed with saturated aqueous ammonium chloride and brine, dried over anhydrous sodium sulfate, and concentrated under reduced pressure. The residue was purified by preparative silica gel thin layer chromatography (n-hexane/ethyl acetate=2/1) to give N-[4-(2,2-dimethylpropionyl)-5-(2-ethenesulfonylaminoethyl)-5-phenyl-4,5-dihydro-1,3,4-thiadiazol-2-yl]-2,2-dimethylpropanamide (0.17 g, 65%).

$^1$H NMR (300 MHz, CDCl$_3$) δ (ppm): 1.30 (s, 9H), 1.32 (s, 9H), 2.48-2.62 (m, 1H), 3.10-3.64 (m, 3H), 4.45 (br t, J=5.7 Hz, 1H), 5.95 (d, J=9.6 Hz, 1H), 6.26 (d, J=16.2 Hz, 1H), 6.52 (dd, J=9.6, 16.2 Hz, 1H), 7.22-7.37 (m, 5H), 7.91 (br s, 1H).

Step 5: N-[4-(2,2-Dimethylpropionyl)-5-(2-ethenesulfonylaminoethyl)-5-phenyl-4,5-dihydro-1,3,4-thiadiazol-2-yl]-2,2-dimethylpropanamide (0.16 g, 0.33 mmol) obtained in Step 4 mentioned above was dissolved in acetonitrile (10 mL), and 70% aqueous ethylamine (1.0 mL, 12 mmol) was added, then the mixture was stirred at room temperature for 3 hours. The reaction mixture was concentrated under reduced pressure, and the residue was purified by preparative silica gel thin layer chromatography (chloroform/methanol/concentrated aqueous ammonia=100/10/1) to give N-{4-(2,2-dimethylpropionyl)-5-[2-(2-ethylaminoethanesulfonyl-amino)ethyl]-5-phenyl-4,5-dihydro-1,3,4-thiadiazol-2-yl}-2,2-dimethylpropanamide} (0.15 g, 86%).

Step 6: N-{4-(2,2-dimethylpropionyl-5-[2-(2-ethylaminoethanesulfonyl-amino)ethyl]-5-phenyl-4,5-dihydro-1,3,4-thiadiazol-2-yl}-2,2-dimethylpropanamide (0.15 g, 0.29 mmol) obtained in Step 5 mentioned above was subjected to preparative high performance liquid chromatography (HPLC) [column: CHIRALCEL OD, φ20×250 mm (Daicel Chemical Industries, Ltd.), elution solvent: hexane/ethanol=80/20 (containing 0.1% diethylamine), flow rate: 6.0 mL/minute] to give a fraction for a retention time of 9.0 minutes among fractions for retention times of 7.5 minutes and 9.0 minutes. The resulting fraction was concentrated to give Compound i {N-{4-(2,2-dimethylpropionyl)-5-[2-(2-ethylaminoethanesulfonylamino)ethyl]-5-phenyl-4,5-dihydro-1,3,4-thiadiazol-2-yl}-2,2-dimethylpropanamide} (33 mg, 22% as a white solid.

$^1$H NMR (270 MHz, CDCl$_3$) δ (ppm): 1.11 (t, J=7.1 Hz, 3H), 1.30 (s, 9H), 1.33 (s, 9H), 2.67 (q, J=7.1 Hz, 2H), 2.53-2.70 (m, 1H), 3.00-3.76 (m, 8H), 7.22-7.38 (m, 5H), 7.92 (br s, 1H).

APCI-MS m/z: 526 (M+H)$^+$.

Reference Example 29

Compound j

N-[5-Aminomethyl-4-(2,2-dimethylpropionyl)-5-phenyl-4,5-dihydro-1,3,4-thiadiazol-2-yl]-2,2-dimethylpropanamide Step 1: [3-(2,2-Dimethylpropionyl)-5-(2,2-dimethylpropionylamino)-2-phenyl-2,3-dihydro-1,3,4-thiadiazol-2-ylmethyl]carbamic acid tert-butyl ester obtained according to the method described in WO2004/092147 was subjected to high performance liquid chromatography (HPLC) [column: CHIRALPAK AD φ4.6×250 mm (Daicel Chemical Industries, Ltd.), elution solvent: hexane/ethanol=80/20, flow rate: 1.0 mL/minute], and a fraction for a retention time of 5.76 minutes was collected among fractions for retention times of 4.63 minutes and 5.76 minutes to give optically active [3-(2,2-dimethylpropionyl)-5-(2,2-dimethylpropionylamino)-2-phenyl-2,3-dihydro-1,3,4-thiadiazol-2-ylmethyl]carbamic acid tert-butyl ester.

Step 2: The optically active [3-(2,2-dimethylpropionyl)-5-(2,2-dimethylpropionyl-amino)-2-phenyl-2,3-dihydro-1,3,4-thiadiazol-2-ylmethyl]carbamic acid tert-butyl ester (5.91 g, 12.4 mmol) obtained in Step 1 mentioned above was dissolved in ethyl acetate (20 mL), and 1 mol/L hydrogen chloride/ethyl acetate solution (40 mL) was added, then the mixture was stirred at room temperature for 1 hour. The deposited crystals were collected by filtration, and the resulting crystals were dried under reduced pressure with heating to give hydrochloride of Compound j {N-[5-amino-methyl-4-(2,2-dimethylpropionyl)-5-phenyl-4,5-dihydro-1,3,4-thiadiazol-2-yl]-2,2-dimethylpropanamide} (4.72 g, 92%).

APCI-MS m/z: 377(M+H)$^+$.

Melting point: 175.0-182.0° C.

Reference Example 30

Compound k

N-[4-(2,2-Dimethylpropionyl)-5-ethenesulfonylaminomethyl-5-phenyl-4,5-dihydro-1,3,4-thiadiazol-2-yl]-2,2-dimethylpropanamide The hydrochloride of Compound j {N-[5-aminomethyl-4-(2,2-dimethyl-propionyl)-5-phenyl-4,5-dihydro-1,3,4-thiadiazol-2-yl]-2,2-dimethylpropanamide} (0.502 g, 1.22 mmol) obtained in Reference Example 29 was dissolved in ethyl acetate (20 mL), and chloroethanesulfonyl chloride (0.203 mL, 1.22 mmol) was added, then the mixture was stirred at room temperature for 2 minutes. The mixture was cooled to 0° C., and triethylamine (0.680 mL, 4.88 mmol) was added, then the mixture was stirred at the same temperature for 30 minutes. To the mixture were added water and 1.0 mol/L hydrochloric acid, and the mixture was extracted with chloroform. The organic layer was washed with water and brine, dried over anhydrous sodium sulfate, and concentrated under reduced pressure. The residue was purified by preparative silica gel thin layer chromatography (hexane/ethyl acetate=3/2) to give Compound k {N-[4-(2,2-dimethylpropionyl)-5-ethenesulfonylaminomethyl-5-phenyl-4,5-dihydro-1,3,4-thiadiazol-2-yl]-2,2-dimethylpropanamide} (0.408 g, 72%).

$^1$H NMR (300 MHz, CDCl$_3$) δ (ppm): 1.29 (s, 9H), 1.33 (s, 9H), 3.85 (dd, J=13.5, 4.8 Hz, 1H), 4.49 (dd, J=13.5, 8.1 Hz, 1H), 5.29 (br s, 1H), 5.93 (br d, J=9.9 Hz, 1H), 6.27 (br d, J=16.5 Hz, 1H), 6.53 (br dd, J=16.4, 9.6 Hz, 1H), 7.27-7.34 (m, 5H), 8.06 (br s, 1H).

APCI-MS m/z: 466 (M)$^+$.

Reference Example 31

Compound l (−)-N-[4-(2,2-Dimethylpropionyl)-5-(2-ethylaminoethanesulfonylaminomethyl)-5-phenyl-4,5-dihydro-1,3,4-thiadiazol-2-yl]-2,2-dimethylpropanamide Compound k {N-[4-(2,2-dimethylpropionyl)-5-ethenesulfonylaminomethyl-5-phenyl-4,5-dihydro-1,3,4-thiadiazol-2-yl]-2,2-dimethylpropanamide} (1.50 g, 3.21 mmol) obtained in Reference Example 30 was dissolved in acetonitrile (60 mL), and 70% aqueous ethylamine (13.9 mL) was added, then the mixture was stirred at room temperature for 1 hour. The mixture was concentrated under reduced pressure, and the resulting residue was dissolved in ethanol. To the solution was added water, and the deposited solid was collected by filtration to give Compound 1 {(−)-N-[4-(2,2-dimethylpropionyl)-5-(2-ethylaminoethanesulfonylaminomethyl)-5-phenyl-4,5-dihydro-1,3,4-thiadiazol-2-yl]-2,2-dimethylpropanamide} (0.830 g, 51%).

$^1$H NMR (300 MHz, CDCl$_3$) δ (ppm): 1.09 (t, J=7.0 Hz, 3H), 1.28 (s, 9H), 1.34 (s, 9H), 2.63 (q, J=7.0 Hz, 2H), 3.03-3.12 (m, 2H), 3.16-3.24 (m, 2H), 4.02 (d, J=13.2 Hz, 1H), 4.58 (d, J=13.2 Hz, 1H), 7.27-7.35 (m, 6H), 8.02 (br s, 1H).

APCI-MS m/z: 512 (M+1)$^+$.

Melting point: 169.0-171.0° C.

Specific rotation: A solution of the resulting compound in methanol gave a negative value as a specific rotation for sodium D line (wavelength: 589.3 nm) at 20° C.

Reference Example 32

Compound m (−)-N-[5-(2-Dimethylaminoethanesulfonylaminomethyl)-4-(2,2-dimethylpropionyl)-5-phenyl-4,5-dihydro-1,3,4-thiadiazol-2-yl]-2,2-dimethylpropanamide Step 1: In the same manner as that in Reference Example 31, from N-[4-(2,2-dimethylpropionyl)-5-ethenesulfonylaminomethyl-5-phenyl-4,5-dihydro-1,3,4-thiadiazol-2-yl]-2,2-dimethylpropanamide (0.05 g, 0.11 mmol) obtained according to the method described in WO2003/051854 and a 2 mol/L dimethylamine/methanol solution (0.10 mL), N-[5-(2-dimethylaminoethanesulfonylaminomethyl)-4-(2,2-dimethylpropionyl)-5-phenyl-4,5-dihydro-1,3,4-thiadiazol-2-yl]-2,2-dimethyl propanamide (0.02 g, 35%) was obtained.

Step 2: N-[5-(2-Dimethylaminoethanesulfonylaminomethyl)-4-(2,2-dimethylpropionyl)-5-phenyl-4,5-dihydro-1,3,4-thiadiazol-2-yl]-2,2-dimethylpropanamide (50 mg) obtained in Step 1 mentioned above was subjected to preparative high performance liquid chromatography (HPLC) [column: CHIRALPAK AD φ20×250 mm (Daicel Chemical Industries, Ltd.), elution solvent: hexane/ethanol=91/9, flow rate: 5.0 mL/minute], and fractions for retention times of 22 minutes and 33 minutes were collected, respectively. Among them, the fraction of 33 minutes was concentrated to give Compound m {(−)-N-[5-(2-dimethylaminoethanesulfonylaminomethyl)-4-(2,2-dimethylpropionyl)-5-phenyl-4,5-dihydro-1,3,4-thiadiazol-2-yl]-2,2-dimethylpropanamide} (17 mg, 34%).

$^1$H NMR (300 MHz, CDCl$_3$) δ (ppm): 1.28 (s, 9H), 1.34 (s, 9H), 2.25 (s, 6H), 2.73 (br q, J=6.3 Hz, 1H), 2.84 (br q, J=6.2 Hz, 1H), 3.18 (br t, J=6.6 Hz, 2H), 4.02 (d, J=13.2 Hz, 1H), 4.58 (d, J=13.2 Hz, 1H), 5.85 (br s, 1H), 7.27-7.35 (m, 5H), 8.02 (br s, 1H).

APCI-MS m/z: 512 (M+1)$^+$.

Melting point: 101.0-104.0° C.

Specific rotation: A solution of the resulting compound in methanol gave a negative value as a specific rotation for sodium D line (wavelength: 589.3 nm) at 20° C.

Reference Example 33

Compound n (−)-N-[5-(3-Dimethylaminopropanesulfonylaminomethyl)-4-(2,2-dimethylpropionyl)-5-phenyl-4,5-dihydro-1,3,4-thiadiazol-2-yl]-2,2-dimethylpropanamide Step 1: The hydrochloride of Compound j {N-[5-aminomethyl-4-(2,2-dimethyl-propionyl)-5-phenyl-4,5-dihydro-1,3,4-thiadiazol-2-yl]-2,2-dimethylpropanamide} (1.00 g, 2.42 mmol) obtained in Reference Example 29 was suspended in dichloromethane (25 mL), and triethylamine (1.35 mL, 9.69 mmol) and 3-chloropropanesulfonyl chloride (0.442 mL, 3.63 mmol) were added under ice cooling, then the mixture was stirred at room temperature for 22 hours. To the mixture were added water and 1 mol/L hydrochloric acid, and the mixture was extracted with chloroform. The organic layer was washed with saturated aqueous sodium hydrogencarbonate and brine, dried over anhydrous sodium sulfate, and concentrated under reduced pressure. The residue was triturated with a mixed solvent of diisopropyl ether and ethyl acetate to give N-[5-(3-chloropropanesulfonylaminomethyl)-4-(2,2-dimethylpropionyl)-5-phenyl-4,5-dihydro-1,3,4-thiadiazol-2-yl]-2,2-dimethylpropanamide (0.880 g, 70%).

$^1$H NMR (270 MHz, CDCl$_3$) δ (ppm): 1.29 (s, 9H), 1.35 (s, 9H), 2.25 (m, 2H), 3.22 (m, 2H), 3.63 (m, 2H), 4.01 (dd, J=5.1, 13.7 Hz, 1H), 4.60 (dd, J=8.0, 13.7 Hz, 1H), 5.19 (dd, J=5.1, 8.0 Hz, 1H), 7.23-7.41 (m, 5H), 7.94 (s, 1H).

ESI-MS m/z: 515, 517 (M−H)$^−$.

Step 2: N-[5-(3-Chloropropanesulfonylaminomethyl)-4-(2,2-dimethylpropionyl)-5-phenyl-4,5-dihydro-1,3,4-thiadiazol-2-yl]-2,2-dimethyl-propanamide (1.50 g, 2.90 mmol) obtained in Step 1 mentioned above, sodium iodide (8.69 g, 58.0 mmol) and sodium azide (1.89 g, 29.0 mmol) were suspended in DMF (20 mL), and the suspension was stirred at 90° C. for 4 hours. To the mixture was added water, and the mixture was extracted with ethyl acetate. The organic layer was washed with brine, dried over anhydrous sodium sulfate, and concentrated under reduced pressure. The residue was triturated with diethyl ether to give N-[5-(3-azidopropanesulfonylaminomethyl)-4-(2,2-dimethyl-propionyl)-5-phenyl-4,5-dihydro-1,3,4-thiadiazol-2-yl]-2,2-dimethyl-propanamide (1.82 g).

Next, the resulting N-[5-(3-azidopropanesulfonylaminomethyl)-4-(2,2-dimethylpropionyl)-5-phenyl-4,5-dihydro-1,3,4-thiadiazol-2-yl]-2,2-dimethylpropanamide was dissolved in THF (53 mL), and water (10.6 mL) and triphenylphosphine (1.24 g, 4.73 mmol) were added, then the mixture was stirred at room temperature for 16 hours. The mixture was concentrated under reduced pressure, and water and saturated aqueous sodium hydrogencarbonate were added, then the mixture was extracted with ethyl acetate. The organic layer was extracted with aqueous hydrochloric acid, and the aqueous layer was made basic by adding saturated aqueous sodium hydrogencarbonate, and then extracted with ethyl acetate. The resulting organic layer was concentrated under reduced pressure to give N-[5-(3-aminopropanesulfonylaminomethyl)-4-(2,2-dimethylpropionyl)-5-phenyl-4,5-dihydro-1,3,4-thiadiazol-2-yl]-2,2-dimethylpropanamide (1.29 g, 89%).

$^1$H NMR (300 MHz, CDCl$_3$) δ (ppm): 1.29 (s, 9H), 1.33 (s, 9H), 1.96 (m, 2H), 2.85 (t, J=6.6 Hz, 2H), 3.19 (t, J=7.5 Hz, 2H), 3.99 (d, J=13.7 Hz, 1H), 4.61 (d, J=13.7 Hz, 1H), 7.24-7.39 (m, 5H).

APCI-MS m/z: 498 (M+H)$^+$.

Step 3: N-[5-(3-Aminopropanesulfonylaminomethyl)-4-(2,2-dimethylpropionyl)-5-phenyl-4,5-dihydro-1,3,4-thiadiazol-2-yl]-2,2-dimethylpropanamide (1.00 g, 2.01 mmol) obtained in Step 2 mentioned above was dissolved in dichloroethane (40 mL), and 37% aqueous formalin (1.63 mL, 0.201 mmol), acetic acid (1.15 mL, 20.1 mmol) and sodium triacetoxyborohydride (4.26 g, 20.1 mmol) were added, then the mixture was stirred at room temperature for 13 hours. To the mixture were added water and saturated aqueous sodium hydrogencarbonate, and the mixture was extracted with chloroform. The organic layer was washed with brine, dried over anhydrous sodium sulfate, and concentrated under reduced pressure. The residue was purified by silica gel column chromatography (chloroform/methanol=9/1→4/1→7/3) to give Compound n {(−)-N-[5-(3-dimethylaminopropanesulfonylaminomethyl)-4-(2,2-dimethylpropionyl)-5-phenyl-4,5-dihydro-1,3,4-thiadiazol-2-yl]-2,2-dimethylpropanamide} (0.910 mg, 86%).

$^1$H NMR (270 MHz, CDCl$_3$) δ (ppm): 1.29 (s, 9H), 1.33 (s, 9H), 1.96 (m, 2H), 2.20 (s, 6H), 2.36 (t, J=6.7 Hz, 2H), 3.12 (m, 2H), 3.96 (d, J=13.4 Hz, 1H), 4.59 (m, 1H), 5.57 (br, 1H), 7.23-7.38 (m, 5H), 7.96 (br, 1H).

APCI-MS m/z: 526 (M+H)$^+$.

Melting point: 92.0-95.0° C.

Specific rotation: A solution of the resulting compound in methanol gave a negative value as a specific rotation for sodium D line (wavelength: 589.3 nm) at 20° C.

Reference Example 34

Compound o

4-[3-(2,2-Dimethylpropionyl)-5-(2,2-dimethylpropionylamino)-2-phenyl-2,3-dihydro-1,3,4-thiadiazol-2-yl]-N-(2-hydroxyethyl)butanamide Step 1: In the same manner as that of the method described in to WO2003/051854, from 4-[3-(2,2-dimethylpropionyl)-5-(2,2-dimethylpropionylamino)-2-phenyl-2,3-dihydro-1,3,4-thiadiazol-2-yl]butanoic acid methyl ester (11.2 g, 25.9 mmol) obtained according to the method described in WO2003/051854 and sodium borohydride (2.94 g, 77.6 mmol), 4-[5-amino-3-(2,2-dimethylpropionyl)-2-phenyl-2,3-dihydro-1,3,4-thiadiazol-2-yl]butanoic acid methyl ester (1.54 g, 17%) was obtained.

APCI-MS m/z: 364 (M+H)$^+$.

Step 2: In the same manner as that in Step 1 of Reference Example 20, from 4-[5-amino-3-(2,2-dimethylpropionyl)-2-phenyl-2,3-dihydro-1,3,4-thiadiazol-2-yl]butanoic acid methyl ester (1.54 g, 4.24 mmol) obtained in Step 1 mentioned above, (S)-(+)-2-phenylpropionic acid (1.99 g, 13.2 mmol), thionyl chloride (20 mL) and pyridine (1.80 mL, 22.0 mmol), a diastereomer mixture was obtained. The resulting diastereomer mixture was purified by silica gel column chromatography (chloroform/acetone=60/12) to give one diastereomer of N-[3-(2,2-dimethylpropionyl)-2-phenyl-5-(2-phenylpropionylamino)-2,3-dihydro-1,3,4-thiadiazol-2-yl]butanoic acid methyl ester (0.679 g, 32%) as a fraction eluted first.

$^1$H NMR (300 MHz, CDCl$_3$) δ (ppm): 1.24 (s, 9H), 1.54 (d, J=8.0 Hz, 3H), 1.42-1.67 (m, 1H), 1.99-2.15 (m, 1H), 2.20-2.32 (m, 1H), 2.38-2.46 (m, 2H), 3.03-3.16 (m, 1H), 3.62-3.71 (m, 1H), 3.67 (s, 3H), 7.18-7.47 (m, 10H), 7.64 (br s, 1H).

APCI-MS m/z: 496 (M+H)$^+$.

Step 3: Sodium hydroxide (0.240 g, 6.01 mmol) was dissolved in water (4.0 mL), and dioxane (8.0 mL) was added, then the mixture was stirred. To the resulting solution was added the one diastereomer of N-[3-(2,2-dimethylpropionyl)-2-phenyl-5-(2-phenylpropionylamino)-2,3-dihydro-1,3,4-thiadiazol-2-yl]butanoic acid methyl ester (0.992 g, 2.00 mmol) obtained in Step 2 mentioned above, and the mixture was stirred at room temperature for 5 hours. To the mixture were added 1 mol/L hydrochloric acid (20 mL) and water (30 mL), and deposited white solid was collected by filtration. The resulting solid was washed with water and diisopropyl ether, and dried under reduced pressure to give 4-[3-(2,2-dimethylpropionyl)-2-phenyl-5-(2-phenyl-propionyl-amino)-2,3-dihydro-1,3,4-thiadiazol-2-yl]butanoic acid (9.60 g, 99%).

APCI-MS m/z: 481 (M+H)$^+$.

Step 4: To 4-[3-(2,2-dimethylpropionyl)-2-phenyl-5-(2-phenylpropionylamino)-2,3-dihydro-1,3,4-thiadiazol-2-yl] butanoic acid (1.03 g, 2.14 mmol) obtained above were added oxalyl chloride (0.223 mL, 2.57 mmol) and DMF (17 μL, 0.214 mmol) at 0° C., and the mixture was stirred at the same temperature for 1 hour. The mixture was concentrated under reduced pressure, to the residue was added dichloromethane (20 mL), and the mixture was stirred at 0° C. Then, ethanolamine (1.2 mL, 21.4 mmol) was added to the mixture, and the mixture was stirred at room temperature for 3 hours. To the mixture were added 1 mol/L hydrochloric acid (20 mL) and water (30 mL), and the mixture was extracted with chloroform. The organic layer was washed with brine, dried over anhydrous sodium sulfate, and concentrated under reduced pressure. To the resulting residue was added diisopropyl ether, and the deposited white solid was collected by filtration. The resulting solid was washed with water and diisopropyl ether, and dried under reduced pressure to give 4-[3-(2,2-dimethylpropionyl)-2-phenyl-5-(2-phenylpropionylamino)-2,3-dihydro-1,3,4-thiadiazol-2-yl]-N-(2-hydroxyethyl)butanamide (1.10 g, 99%).

APCI-MS m/z: 525 (M+H)$^+$.

Step 5: To 4-[3-(2,2-dimethylpropionyl)-2-phenyl-5-(2-phenylpropionylamino)-2,3-dihydro-1,3,4-thiadiazol-2-yl]-N-(2-hydroxyethyl)butanamide (1.21 g, 2.31 mmol) obtained in Step 4 mentioned above was added dichloromethane (20 mL), and the mixture was stirred at 0° C. Then, to the mixture were added pyridine (0.470 mL, 5.77 mmol) and tert-butyldimethylsilyl chloride (869 mg, 5.77 mmol), and the mixture was stirred at room temperature for 3 hours. To the mixture were added 1 mol/L hydrochloric acid (20 mL) and water (30 mL), and the mixture was extracted with chloroform. The organic layer was washed with brine, dried over anhydrous sodium sulfate, and concentrated under reduced pressure. To the resulting residue was added diisopropyl ether, and the deposited white solid was collected by filtration. The resulting solid was washed with water and diisopropyl ether, and dried under reduced pressure to give N-[2-(tert-butyldimethylsiloxy)ethyl]-4-[3-(2,2-dimethylpropionyl)-2-phenyl-5-(2-phenylpropionylamino)-2,3-dihydro-1,3,4-thiadiazol-2-yl]butanamide (1.25 g, 85%).

APCI-MS m/z: 638 (M+H)$^+$.

Step 6: In the same manner as that in Step 2 of Reference Example 20, from N-[2-(tert-butyldimethylsiloxy)ethyl]-4-[3-(2,2-dimethylpropionyl)-2-phenyl-5-(2-phenylpropionylamino)-2,3-dihydro-1,3,4-thiadiazol-2-yl]butanamide (0.376 g, 0.588 mmol obtained in Step 5 mentioned above and sodium borohydride (0.111 g, 2.94 mmol), optically active 4-[5-amino-3-(2,2-dimethylpropionyl)-2-phenyl-2,3-dihydro-1,3,4-thiadiazol-2-yl]-N-[2-(tert-butyldimethylsiloxy) ethyl]butanamide (0.113 g, 38%) was obtained.

$^1$H NMR (270 MHz, CDCl$_3$) δ (ppm): 0.03 (s, 3H), 0.07 (s, 3H), 0.86 (s, 9H), 0.90 (s, 9H), 2.15-2.28 (m, 1H), 2.49-2.58 (m, 1H), 2.62-2.82 (m, 2H), 3.07-3.13 (m, 1H), 3.27-3.47 (m, 3H), 3.59-3.72 (m, 2H), 4.21 (br s, 2H), 5.97 (m, 1H), 7.22-7.44 (m, 5H).

APCI-MS m/z: 507 (M+H)$^+$.

Step 7: In the same manner as that in Step 3 of Reference Example 20, from the optically active 4-[5-amino-3-(2,2-dimethylpropionyl)-2-phenyl-2,3-dihydro-1,3,4-thiadiazol-2-yl]-N-[2-(tert-butyldimethylsiloxy)ethyl]butanamide (0.0683 g, 0.135 mmol) obtained in Step 6 mentioned above, pyridine (131 μL, 1.62 mmol) and trimethylacetyl chloride (0.166 mL, 1.35 mmol), optically active N-[2-(tert-butyldimethylsiloxy)ethyl]-4-[3-(2,2-dimethylpropionyl)-5-(2,2-dimethylpropionylamino)-2-phenyl-2,3-dihydro-1,3,4-thiadiazol-2-yl]butanamide (68.0 mg, 83%) was obtained.

Step 8: The optically active N-[2-(tert-butyldimethylsiloxy)ethyl]-4-[3-(2,2-dimethyl-propionyl)-5-(2,2-dimethylpropionylamino)-2-phenyl-2,3-dihydro-1,3,4-thiadiazol-2-yl]butanamide (71.0 mg, 0.117 mmol) obtained in Step 7 mentioned above was dissolved in THF (1 mL), to the solution was added a 1 mol/L solution of tetrabutylammonium fluoride in THF (0.16 mL), and the mixture was stirred at room temperature for 50 minutes. To the mixture was added water (1 mL), and the mixture was extracted with ethyl acetate. The organic layer was washed with brine, dried over anhydrous sodium sulfate, and concentrated under reduced pressure. The residue was purified by column chromatography (chloroform/methanol=9/1) to give Compound o {4-[3-(2,2-dimethylpropionyl)-5-(2,2-dimethylpropionylamino)-2-phenyl-2,3-dihydro-1,3,4-thiadiazol-2-yl]-N-(2-hydroxyethyl)butanmide} (47.6 mg, 85%) as white solid.

$^1$H NMR (300 MHz, CDCl$_3$) δ (ppm): 1.28 (s, 9H), 1.33 (s, 9H), 1.56 (m, 1H), 2.22-2.51 (m, 4H), 3.15 (m, 1H), 3.35 (m, 1H), 3.45 (m, 1H), 3.61-3.76 (m, 2H), 6.31 (br s, 1H), 7.41-7.72 (m, 5H), 8.05 (br s, 1H).

APCI-MS m/z: 477 (M+H)$^+$.

Reference Examples 35 to 41

Compounds p to v

Compounds p to v can be synthesized according to any one of the methods described in any one of of Reference Examples 20 to 34, respectively.

Reference Example 42

Compound w

N-[5-(3-Aminopropanesulfonylaminomethyl)-4-(2,2-dimethylpropionyl)-5-phenyl-4,5-dihydro-1,3,4-thiadiazol-2-yl]-2,2-dimethylpropanamide Step 1: The hydrochloride of Compound j {N-[5-aminomethyl-4-(2,2-dimethyl-propionyl)-5-phenyl-4,5-dihydro-1,3,4-thiadiazol-2-yl]-2,2-dimethylpropanamide} (1.00 g, 2.42 mmol) obtained in Reference Example 29 was suspended in dichloromethane (25 mL), and triethylamine (1.35 mL, 9.69 mmol) and 3-chloropropanesulfonyl chloride (0.442 mL, 3.63 mmol) were added under ice cooling, then the mixture was stirred at room temperature for 22 hours. To the mixture were added water and 1 mol/L hydrochloric acid, and the mixture was extracted with chloroform. The organic layer was washed with saturated aqueous sodium hydrogencarbonate and brine, dried over anhydrous sodium sulfate, and concentrated under reduced pressure. The residue was triturated with a mixed solvent of diisopropyl ether and ethyl acetate to give optically active N-[5-(3-chloropropanesulfonylaminomethyl)-4-(2,2-dimethyl-propionyl)5-phenyl-4,5-dihydro-1,3,4-thiadiazol-2-yl]-2,2-dimethylpropanamide (0.880 g, 70%).

$^1$H NMR (270 MHz, CDCl$_3$) δ (ppm): 1.29 (s, 9H), 1.35 (s, 9H), 2.25 (m, 2H), 3.22 (m, 2H), 3.63 (m, 2H), 4.01 (dd, J=5.1, 13.7 Hz, 1H), 4.60 (dd, J=8.0, 13.7 Hz, 1H), 5.19 (dd, J=5.1, 8.0 Hz, 1H), 7.23-7.41 (m, 5H), 7.94 (s, 1H).

ESI-MS m/z: 515, 517 (M−H)$^-$.

Step 2: The optically active N-[5-(3-chloropropanesulfonylaminomethyl)-4-(2,2-dimethylpropionyl)-5-phenyl-4,5-dihydro-1,3,4-thiadiazol-2-yl]-2,2-dimethylpropanamide (1.50 g, 2.90 mmol) obtained in Step 1 mentioned above, sodium iodide (8.69 g, 58.0 mmol) and sodium azide (1.89 g, 29.0 mmol) were suspended in DMF (20 mL), and the suspension was stirred at 90° C. for 4 hours. To the mixture was added water, and the mixture was extracted with ethyl acetate. The organic layer was washed with brine, dried over anhydrous sodium sulfate, and concentrated under reduced pressure. The residue was triturated with diethyl ether to give optically active N-[5-(3-azidopropanesulfonylaminomethyl)-4-(2,2-dimethylpropionyl)-5-phenyl-4,5-dihydro-1,3,4-thiadiazol-2-yl]-2,2-dimethylpropanamide (1.82 g).

Next, the resulting optically active N-[5-(3-azidopropanesulfonylamino-methyl)-4-(2,2-dimethylpropionyl)-5-phenyl-4,5-dihydro-1,3,4-thiadiazol-2-yl]-2,2-dimethylpropanamide was dissolved in THF (53 mL), and water (10.6 mL) and triphenylphosphine (1.24 g, 4.73 mmol) were added, then the mixture was stirred at room temperature for 16 hours. The mixture was concentrated under reduced pressure, and water and saturated aqueous sodium hydrogencarbonate were added, then the mixture was extracted with ethyl acetate. The organic layer was extracted with aqueous hydrochloric acid, and the aqueous layer was made basic by adding saturated aqueous sodium hydrogencarbonate, and then extracted with ethyl acetate. The resulting organic layer was concentrated under reduced pressure to give Compound w {N-[5-(3-aminopropanesulfonylaminomethyl)-4-(2,2-dimethylpropionyl)-5-phenyl-4,5-dihydro-1,3,4-thiadiazol-2-yl]-2,2-dimethylpropanamide} (1.29 g, 89%).

$^1$H NMR (300 MHz, CDCl$_3$) δ (ppm): 1.29 (s, 9H), 1.33 (s, 9H), 1.96 (m, 2H), 2.85 (t, J=6.6 Hz, 2H), 3.19 (t, J=7.5 Hz, 2H), 3.99 (d, J=13.7 Hz, 1H), 4.61 (d, J=13.7 Hz, 1H), 7.24-7.39 (m, 5H).

APCI-MS m/z: 498 (M+H)$^+$.

Reference Example 43

Compound x

[(2R)-3-(2,2-Dimethylpropionyl)-5-(2,2-dimethylpropionylamino)-2-phenyl-2,3-dihydro-1,3,4-thiadiazol-2-ylmethyl]carbamic acid tert-butyl ester Compound 22

{[3-(2,2-Dimethylpropionyl)-5-(2,2-dimethylpropionylamino)-2-phenyl-2,3-dihydro-1,3,4-thiadiazol-2-ylmethyl]carbamic acid tert-butyl ester} obtained in Reference Example 45 was subjected to high performance liquid chromatography (HPLC) [column: CHIRALPAK AD φ4.6×250 mm (Daicel Chemical Industries, Ltd.), elution solvent: hexane/ethanol=80/20, flow rate: 1.0 mL/minute], and a fraction for a retention time of 5.76 minutes was collected among fractions for retention times of 4.63 minutes and 5.76 minutes to give Compound x {[(2R)-3-(2,2-dimethylpropionyl)-5-(2,2-dimethyl-propionylamino)-2-phenyl-2,3-dihydro-1,3,4-thiadiazol-2-ylmethyl]-carbamic acid tert-butyl ester}.

Reference Example 44

Compound 21

N-{4-(2,2-Dimethylpropionyl)-5-[2-(2-ethylaminoethanesulfonylamino)-ethyl]-5-phenyl-4,5-dihydro-1,3,4-thiadiazol-2-yl}-2,2-dimethylpropanamide Step 1: Palladium(II) acetate (125 mg, 0.559 mmol) and triphenylphosphine (317 mg, 1.21 mmol) were dissolved in tetrahydrofuran (THF, 50 mL). To the resulting solution were added N-tert-butoxycarbonyl-B-alanine (2.07 g, 10.9 mmol), phenylboronic acid (1.61 g, 13.2 mmol), distilled water (0.477 mL, 26.5 mmol) and trimethylacetic anhydride (3.23 mL, 15.9 mmol), and the mixture was stirred at 60° C. for 24 hours. The mixture was filtered, saturated aqueous sodium hydrogencarbonate was added to the filtrate, and the mixture was extracted with ethyl acetate. The organic layer was washed with brine, dried over anhydrous sodium sulfate, and concentrated under reduced pressure. The residue was purified by silica gel column chromatography (hexane/ethyl acetate=9/1→4/1) to give (3-oxo-3-phenylpropyl)carbamic acid tert-butyl ester (1.85 g, 68%).

Step 2: (3-Oxo-3-phenylpropyl)carbamic acid tert-butyl ester (513 mg, 2.06 mmol) obtained in Step 1 mentioned above was dissolved in methanol (40 mL). To the resulting solution was added thiosemicarbazide hydrochloride (562 mg, 4.40 mmol), and the mixture was stirred at room temperature for 8 hours. To the mixture was added water, and the mixture was extracted with ethyl acetate. The organic layer was washed with brine, dried over anhydrous sodium sulfate, and concentrated under reduced pressure to give a pale yellow solid (513 mg). Apart of the resulting solid (198 mg) was dissolved in dichloromethane (10 mL). To the resulting solution were added pyridine (0.300 mL, 3.73 mmol) and trimethylacetyl chloride (0.415 mL, 3.37 mmol), and the mixture was stirred at room temperature for 22 hours. To the mixture was added saturated aqueous sodium hydrogencarbonate, and the mixture was further stirred at room temperature for 1 hour, and extracted with ethyl acetate. The organic layer was washed with brine, dried over anhydrous sodium sulfate, and concentrated under reduced pressure. The residue was purified by preparative silica gel thin layer chromatography (n-hexane/ethyl acetate=2/1) to give {2-[3-(2,2-dimethylpropionyl)-5-(2,2-dimethylpropionylamino)-2-phenyl-2,3-dihydro-1,3,4-thiadiazol-2-yl]ethyl}-carbamic acid tert-butyl ester (319 mg, 100%).

APCI-MS m/z: 491(M+H)$^+$.

Step 3: {2-[3-(2,2-Dimethylpropionyl)-5-(2,2-dimethylpropionylamino)-2-phenyl-2,3-dihydro-1,3,4-thiadiazol-2-yl]ethyl}carbamic acid tert-butyl ester (274 mg, 0.557 mmol) obtained in Step 2 mentioned above was dissolved in dichloromethane (10 mL). To the resulting solution was added trifluoroacetic acid (1.0 mL), and the mixture was stirred at room temperature for 3 hours, and then concentrated under reduced pressure. To the residue was added diisopropyl ether, and the mixture was stirred for 3 hours. The deposited white solid was collected by filtration to give trifluoroacetate of N-[5-(2-aminoethyl)-4-(2,2-dimethylpropionyl)-5-phenyl-4,5-dihydro-1,3,4-thiadiazol-2-yl]-2,2-dimethylpropanamide (252 mg, 90%).

APCI-MS m/z: 391(M+H)$^+$.

Step 4: The trifluoroacetate of N-[5-(2-aminoethyl)-4-(2,2-dimethylpropionyl)-5-phenyl-4,5-dihydro-1,3,4-thiadiazol-2-yl]-2,2-dimethylpropanamide (0.25 g, 0.53 mmol) obtained in Step 3 mentioned above was dissolved in methanol (5 mL), and the solution was loaded on a column filled with ion exchange silica gel [SCX (Varian, BONDESIL SCX 40 μM)]. After SCX was washed with methanol, a fraction eluted with a 1% hydrogen chloride—methanol solution was collected, and the fraction was concentrated under reduced pressure to give hydrochloride of N-[5-(2-aminoethyl)-4-(2,2-dimethylpropionyl)-5-phenyl-4,5-dihydro-1,3,4-thiadiazol-2-yl]-2,2-dimethyl-propanamide (0.19 g) as a white solid.

The hydrochloride obtained above was dissolved in dichloromethane (10 mL), and 2-chloroethanesulfonyl chloride (0.14 mL, 2.2 mmol) and triethylamine (0.62 mL, 4.6 mmol) were added at 0° C., then the mixture was stirred at the same temperature for 4 hours, and then at room temperature for 10 hours. To the mixture was added saturated aqueous sodium hydrogencarbonate, and the mixture was extracted with ethyl acetate. The organic layer was washed with saturated aqueous ammonium chloride and brine, dried over anhydrous sodium sulfate, and concentrated under reduced pressure. The residue was purified by preparative silica gel thin layer chromatography (n-hexane/ethyl acetate=2/1) to give N-[4-(2,2-dimethylpropionyl)-5-(2-ethenesulfonylaminoethyl)-5-phenyl-4,5-dihydro-1,3,4-thiadiazol-2-yl]-2,2-dimethylpropanamide (0.17 g, 65%).

$^1$H NMR (300 MHz, CDCl$_3$) δ (ppm): 1.30 (s, 9H), 1.32 (s, 9H), 2.48-2.62 (m, 1H), 3.10-3.64 (m, 3H), 4.45 (br t, J=5.7 Hz, 1H), 5.95 (d, J=9.6 Hz, 1H), 6.26 (d, J=16.2 Hz, 1H), 6.52 (dd, J=9.6, 16.2 Hz, 1H), 7.22-7.37 (m, 5H), 7.91 (br s, 1H).

Step 5: N-[4-(2,2-Dimethylpropionyl)-5-(2-ethenesulfonylaminoethyl)-5-phenyl-4,5-dihydro-1,3,4-thiadiazol-2-yl]-2,2-dimethylpropanamide (0.16 g, 0.33 mmol) obtained in Step 4 mentioned above was dissolved in acetonitrile (10 mL), and 70% aqueous ethylamine (1.0 mL, 12 mmol) was added, then the mixture was stirred at room temperature for 3 hours. The reaction mixture was concentrated under reduced pressure, and the residue was purified by preparative silica gel thin layer chromatography (chloroform/methanol/concentrated aqueous ammonia=100/10/1) to give Compound 21 {N-{4-(2,2-dimethylpropionyl)-5-[2-(2-ethylaminoethanesulfonyl-amino)ethyl]-5-phenyl-4,5-dihydro-1,3,4-thiadiazol-2-yl}-2,2-dimethylpropanamide} (0.15 g, 86%).

Reference Example 45

Compound 22

[3-(2,2-Dimethylpropionyl)-5-(2,2-dimethylpropionylamino)-2-phenyl-2,3-dihydro-1,3,4-thiadiazol-2-ylmethyl]carbamic acid tert-butyl ester Step 1: 2-Aminoacetophenone hydrochloride (400 g, 2.33 mol) was dissolved in a mixed solvent of water (2.8 L) and ethyl acetate (3.6 L), and di-tert-butyl dicarbonate (534 g, 2.45 mol) together with ethyl acetate (400 mL) were added under ice cooling. Aqueous potassium carbonate (322 g/1.2 L) was dropped to the solution with vigorously stirring over 1 hour. After the mixture was stirred for 1.5 hours under ice cooling, the temperature was elevated to 30° C., and the mixture was stirred for 1 hour at 30° C. Disappearance of the starting material was confirmed by analysis based on high performance liquid chromatography (HPLC), and then the organic layer was separated and washed with brine (800 mL). The organic layer was concentrated under reduced pressure to give 2-(tert-butoxycarbonylamino)acetophenone (610 g) as a slightly yellow oil. This compound was used for the following step without further purification.

$^1$H NMR (300 MHz, DMSO-d$_6$) δ (ppm): 7.96 (br d, J=7.4 Hz, 2H), 7.61 (tt, J=7.4, 1.6 Hz, 1H), 7.49 (br t, J=7.4 Hz, 2H), 5.54 (br s, 1H), 4.66 (d, J=4.6 Hz, 2H), 1.48 (s, 9H).

Step 2: 2-(tert-Butoxycarbonylamino)acetophenone (610 g) obtained above was dissolved in methanol (4.0 L), and the solution was cooled on ice. Thiosemicarbazide (425 g, 4.66 mol) was dissolved in diluted hydrochloric acid (concentrated hydrochloric acid (388 mL) and water (1612 mL)), and an about half volume of this solution (1 L) was added dropwise to the aforementioned solution over 10 minutes. Then, seed crystals of 2-(tert-butoxycarbonylamino)acetophenone thiosemicarbazone (400 mg) prepared in Reference Example A were added, and then the remaining thiosemicarbazide solution was added dropwise over 30 minutes. The mixture was further stirred at room temperature for 1 hour, and water (2.0 L) was added, then the mixture was stirred at 5° C. for 1 hour. The deposited solid was collected by filtration, and washed with cooled 50% aqueous methanol (1.2 L) and then with cold water (800 mL). The resulting solid was dried at 50° C. for 24 hours under reduced pressure to give 2-(tert-butoxycarbonylamino)acetophenone thiosemicarbazone as a white solid (694 g, yield: 92.1% (for two steps)).

$^1$H NMR (300 MHz, DMSO-d$_6$) δ (ppm): 10.6 (br s, 1H), 8.37 (br s, 1H), 8.03-7.83 (m, 3H), 7.67 (br t, J=4.1 Hz, 1H), 7.42-7.30 (m, 3H), 4.17 (br d, J=4.1 Hz, 2H), 1.38 (s, 9H).

Step 3: 2-(tert-Butoxycarbonylamino)acetophenone thiosemicarbazone obtained above (690 g, 2.24 mol) was suspended in acetonitrile (6.9 L), and pyridine (619 g) was added, then the mixture was cooled on ice. To the mixture was added dropwise pivaloyl chloride (809 g) over 25 minutes. After the mixture was stirred at room temperature for 5.5 hours, 1 mol/L hydrochloric acid (1.2 L) was added, and the mixture was stirred for several minutes, and then the aqueous phase was removed. To the organic layer was added water (690 mL) dropwise over 40 minutes with stirring. The solid deposited during the dropping, and the resulting suspension was further stirred at 5° C. for 1 hour. The deposited solid was collected by filtration, and washed with cooled acetonitrile/water (10:1, 2.0 L) and then with cold water (1.4 L). The resulting solid was dried under reduced pressure at 25° C. for 32 hours to give the title compound 22 {[3-(2,2-dimethylpropionyl)-5-(2,2-dimethylpropionylamino)-2-phenyl-2,3-dihydro-1,3,4-thiadiazol-2-ylmethyl]carbamic acid tert-butyl ester} as a white solid (1031 g, yield: 95.4%).

$^1$H NMR (300 MHz, DMSO-d$_6$) δ (ppm): 10.89 (s, 1H), 7.40-7.20 (m, 5H), 6.74 (br dd, J=6.8, 6.1 Hz, 1H), 4.37 (dd, J=14.5, 6.8 Hz, 1H), 3.98 (dd, J=14.5, 6.1 Hz, 1H), 1.37 (s, 9H), 1.29 (s, 9H), 1.17 (s, 9H).

Reference Example 46

Compound 23

N-{4-(2,2-Dimethylpropionyl)-5-[2-(hydroxyamino) ethanesulfonylaminomethyl]-5-phenyl-4,5-dihydro-[1,3,4]thiadiazol-2-yl}-2,2-dimethylpropionamide Compound 10 {N-[4-(2,2-dimethylpropionyl)-5-ethenesulfonylaminomethyl-5-phenyl-4,5-dihydro-1,3,4-thiadiazol-2-yl]-2,2-dimethylpropanamide} (101 mg, 0.216 mmol) obtained in Reference Example 10 was dissolved in acetonitrile (5 mL), and hydroxylamine (containing 50% water, 0.265 mL) was added, then the mixture was stirred at room temperature for 1.5 hours. The reaction mixture was concentrated under reduced pressure, and the resulting residue was purified by preparative thin layer chromatography (chloroform/methanol=20/1), and then triturated with diisopropyl ether to give Compound 22 {N-{4-(2,2-dimethylpropionyl)-5-[2-(hydroxyamino)ethanesulfonylaminomethyl]-5-phenyl-4,5-dihydro-[1,3,4]thiadiazol-2-yl}-2,2-dimethyl-propionamide} (89 mg, 83%).

$^1$H NMR (300 MHz, CDCl$_3$) δ (ppm): 1.29 (s, 9H), 1.34 (s, 9H), 3.01 (br d, J=14.4 Hz, 1H), 3.30-3.70 (m, 3H), 4.04 (dd, J=10.8, 12.3 Hz, 1H), 4.58 (dd, J=3.3, 12.3 Hz, 1H), 5.21 (dd, J=3.3, 10.8 Hz, 1H), 5.27 (br s, 1H), 6.46 (br s, 1H), 7.20-7.41 (m, 5H), 7.94 (br s, 1H).

Reference Example 17

Compound 17

N-{4-(2,2-Dimethylpropionyl)-5-[2-(N-ethyl-N-hydroxyamino)ethanesulfonylamino-methyl]-5-phenyl-4,5-dihydro-[1,3,4]thiadiazol-2-yl}-2,2-dimethylpropionamide Compound 23 {N-{4-(2,2-dimethylpropionyl)-5-[2-(hydroxyamino)ethane-sulfonylaminomethyl]-5-phenyl-4,5-dihydro-[1,3,4]thiadiazol-2-yl}-2,2-dimethyl-propionamide} (60 mg, 0.12 mmol) obtained in Reference Example 46 was dissolved in 1,2-dichloroethane (2.4 mL), and acetaldehyde (0.095 mL, 1.7 mmol), acetic acid (0.068 mL, 1.2 mmol) and sodium triacetoxyborohydride (256 mg, 1.21 mmol) were added, then the mixture was stirred at room temperature for 10 minutes. To the mixture were added water and saturated aqueous sodium hydrogencarbonate, and the mixture was extracted with chloroform. The organic layer was washed with brine, dried over anhydrous sodium sulfate, and then concentrated under reduced pressure. The residue was purified by preparative thin layer chromatography (chloroform/methanol=20/1), and then triturated with diisopropyl ether to give Compound 17 {N-{4-(2,2-dimethylpropionyl)-5-[2-(N-ethyl-N-hydroxyamino)ethanesulfonylaminomethyl]-5-phenyl-4,5-dihydro-[1,3,4]thiadiazol-2-yl}-2,2-dimethylpropionamide} (23 mg, 36%).

$^1$H NMR (300 MHz, CDCl$_3$) δ (ppm): 1.09 (t, J=7.2 Hz, 3H), 1.28 (s, 9H), 1.39 (s, 9H), 2.73-2.90 (m, 3H), 2.90-3.30 (m, 2H), 3.40-3.60 (m, 1H), 4.04 (dd, J=9.6, 12.9 Hz, 1H), 4.60 (dd, J=5.1, 12.9 Hz, 1H), 5.50 (br s, 1H), 6.50 (br s, 1H), 7.20-7.40 (m, 5H), 7.93 (br s, 1H).

Reference Example 47

Compound 24

N-{5-[2-(2-Aminoethylsulfanyl)ethanesulfonylaminomethyl]-4-(2,2-dimethyl-propionyl)-5-phenyl-4,5-dihydro[1,3,4]thiadiazol-2-yl}-2,2-dimethyl-propionamide Step 1: Compound 10 {N-[4-(2,2-dimethylpropionyl)-5-ethenesulfonylaminomethyl-5-phenyl-4,5-dihydro-1,3,4-thiadiazol-2-yl]-2,2-dimethylpropanamide} (1.001 g, 2.145 mmol) obtained in Reference Example 10 was dissolved in methanol (20 mL), and 2-aminoethanethiol hydrochloride (1.230 g, 10.83 mmol) and saturated aqueous sodium hydrogencarbonate (15 mL) were added, then the mixture was stirred at room temperature for 1.5 hours. To the mixture was added water, and the mixture was extracted with ethyl acetate. The organic layer was washed with brine, dried over anhydrous sodium sulfate, and concentrated under reduced pressure. The residue was triturated with diethyl ether and then with a mixed solvent of diethyl ether and ethyl acetate (9/1). The resulting crude product was purified by silica gel column chromatography (chloroform/methanol=6/1), and triturated with diethyl ether to give free base of Compound 24 {N-{5-[2-(2-aminoethylsulfanyl)ethanesulfonyl-aminomethyl]-4-(2,2-dimethylpropionyl)-5-phenyl-4,5-dihydro[1,3,4]thiadiazol-2-yl}-2, 2-dimethylpropionamide} (756 mg, 65%).

APCI-MS m/z: 544 (M+1)$^+$.

Step 2: The free base of Compound 24 (756 mg, 1.39 mmol) obtained in Step 1 mentioned above was dissolved in ethyl acetate (20 mL), and to the solution was added 4 mol/L hydrogen chloride-ethyl acetate solution (0.7 mL) under ice cooling. The reaction mixture was concentrated under reduced pressure, and diethyl ether was added, then the mixture was stirred at room temperature for 30 minutes. Then, the deposited solid was collected by filtration to give hydrochloride of Compound 24 (795 mg, 99%).

$^1$H NMR (270 MHz, DMSO-d$_6$) δ (ppm): 1.18 (s, 9H), 1.27 (s, 9H), 2.77 (t, J=7.1 Hz, 2H), 2.86 (m, 2H), 2.98 (t, J=7.1 Hz, 2H), 3.37 (m, 2H), 4.00 (d, J=14.0 Hz, 1H), 4.36 (d, J=14.0 Hz, 1H), 7.21-7.38 (m, 5H), 8.50 (br, 3H).

Reference Example 48

Compound 25

N-{5-[(2-Aminoethylsulfanyl)methanesulfonylaminomethyl]-4-(2,2-dimethyl-propionyl)-5-phenyl-4,5-dihydro[1,3,4]thiadiazol-2-yl}-2,2-dimethyl propionamide Step 1: The hydrochloride of Compound 11 {N-[5-aminomethyl-4-(2,2-dimethyl-propionyl)-5-phenyl-4,5-dihydro-1,3,4-thiadiazol-2-yl]-2,2-dimethylpropanamide} (4.00 g, 9.69 mmol) obtained in Reference Example 11 was dissolved in dichloromethane (100 mL), and triethylamine (4.05 mL, 29.1 mmol) and chloromethanesulfonyl chloride (1.12 mL, 12.6 mmol) were added under ice cooling, then the mixture was stirred at room temperature for 4 hours. To the mixture were added water and 1 mol/L hydrochloric acid, and the mixture was extracted with chloroform. The organic layer was washed with brine, dried over anhydrous sodium sulfate, and concentrated under reduced pressure. The residue was triturated with a mixed solvent of chloroform and diisopropyl ether to give N-[5-chloromethanesulfonylaminomethyl-4-(2,2-dimethyl-propionyl)-5-phenyl-4,5-dihydro[1,3,4]thiadiazol-2-yl]-2,2-dimethylpropionamide (3.82 g, 92%).

APCI-MS m/z: 489, 491 (M+1)$^+$.

Step 2: N-[5-Chloromethanesulfonylaminomethyl-4-(2,2-dimethylpropionyl)-5-phenyl-4,5-dihydro[1,3,4]thiadiazol-2-yl]-2,2-dimethylpropionamide (3.818 g, 7.807 mmol) obtained in Step 1 mentioned above was dissolved in DMF (70 mL), and tert-butyl N-(2-mercaptoethyl)carbamate (13.3 mL, 78.1 mmol) and saturated aqueous sodium hydrogencarbonate (15 mL) were added, then the mixture was stirred at 70° C. for 5.5 hours. After cooling, water was added, and the mixture was extracted with ethyl acetate. The organic layer was washed with brine, dried over anhydrous sodium sulfate, and concentrated under reduced pressure. The residue was purified by silica gel column chromatography (n-hexane/ethyl acetate=9/1→7/3), and then triturated with diisopropyl ether to give [2-({[3-(2,2-dimethylpropionyl)-5-(2,2-dimethyl-propionylamino)-2-phenyl-2,3-dihydro[1,3,4]thiadiazol-2-ylmethyl]sulfamoyl}-methylsulfanyl)ethyl]carbamic acid tert-butyl ester (1.926 g, 39%).

APCI-MS m/z: 630 (M+1)$^+$.

Step 3: [2-({[3-(2,2-Dimethylpropionyl)-5-(2,2-dimethylpropionylamino)-2-phenyl-2,3-dihydro[1,3,4]thiadiazol-2-ylmethyl]sulfamoyl}methylsulfanyl)ethyl]carbamic acid tert-butyl ester (1.926 g, 3.058 mmol) obtained in Step 2 mentioned above was dissolved in dichloromethane (15 mL), and trifluoroacetic acid (15 mL) was added, then the mixture was stirred at room temperature for 1 hour. After the mixture was concentrated under reduced pressure, to the residue were added water and saturated aqueous sodium hydrogencarbonate, and the mixture was extracted with ethyl acetate. The organic layer was washed with brine, dried over anhydrous sodium sulfate, and concentrated under reduced pressure. The residue was purified by silica gel column chromatography (chloroform/methanol=9/1→chloroform containing ammonia/methanol=9/1), and then triturated with diisopropyl ether to give free base of Compound 25 {N-{5-[(2-aminoethylsulfanyl)methanesulfonylaminomethyl]-4-(2,2-dimethylpropionyl)-5-phenyl-4,5-dihydro[1,3,4]thiadiazol-2-yl}-2,2-dimethyl propionamide} (1.011 g, 63%).

APCI-MS m/z: 530 (M+1)$^+$.

Step 4: In the same manner as that in Step 2 of Reference Example 47, the free base of Compound 25 (515 mg, 0.972 mmol) obtained in Step 3 mentioned above was treated with 4 mol/L hydrogen chloride-ethyl acetate solution (0.5 mL) to give hydrochloride of Compound 25 (490 mg, 89%).

$^1$H NMR (300 MHz, CDCl$_3$) δ (ppm): 1.26 (s, 9H), 1.32 (s, 9H), 3.10 (m, 2H), 3.11 (m, 2H), 4.06 (dd, J=5.4, 14.2 Hz, 1H), 4.15 (d, J=15.0 Hz, 1H), 4.24 (d, J=15.0 Hz, 1H), 4.67 (m, 1H), 6.34 (m, 1H), 7.23-7.38 (m, 5H), 8.14 (br, 3H), 8.38 (s, 1H).

Reference Example 49

Compound 26

N-{2-[3-Acetyl-5-(2-oxopiperidino)-2-phenyl-2,3-dihydro-1,3,4-thiadiazol-2-yl]ethyl}-methanesulfonamide In the same manner as that in Reference Example 22, from N-[2-(3-acetyl-5-amino-2-phenyl-2,3-dihydro-1,3,4-thiadiazol-2-yl)ethyl]methanesulfonamide (0.150 g, 0.438 mmol) obtained on the way of Step 3 of Reference Example 25, pyridine (51.0 μL, 0.631 mmol), 5-bromovaleryl chloride (70.5 μL, 0.526 mmol) and sodium acetate (0.0498 g, 0.607 mmol), Compound 26 {N-{2-[3-acetyl-5-(2-oxopiperidino)-2-phenyl-2,3-dihydro-1,3,4-thiadiazol-2-yl]ethyl}methanesulfonamide} (0.181 g, 97%) was obtained.

$^1$H NMR (270 MHz, CDCl$_3$) δ (ppm): 1.82-1.98 (m, 4H), 2.33 (s, 3H), 2.52-2.62 (m, 3H), 2.95 (s, 3H), 3.27-3.38 (m, 2H), 3.59-3.70 (m, 1H), 3.84-3.92 (m, 2H), 4.62 (br s, 1H), 7.23-7.37 (m, 5H).

APCI-MS m/z: 423 (M-1)$^-$.

Reference Examples 50 and 51

Compounds 50 and 51

Compounds 50 and 51 were synthesized according to the method described in WO2003/051854.

Reference Examples 52 to 62

Compounds 52, 53, 54, 55, 56, 57, 58, 59, 60, 61 and 62

Compounds 52, 53, 54, 55, 56, 57, 58, 59, 60, 61 and 62 were synthesized according to the method described in WO2004/092147.

Reference Examples 63 to 70

Compounds 63, 64, 65, 66, 67, 68, 69 and 70

Compound 63, 64, 65, 66, 67, 68, 69 and 70 were synthesized according to the method described in WO2004/111024.

Reference Examples 71 and 72

Compounds 71 and 72

Compound 71 and 72 were synthesized according to the method described in WO2003/051854 or WO2004/092147.
Compound 71 APCI-MS m/z: 477 (M)$^+$.
Compound 72 APCI-MS m/z: 527 (M)$^+$.

Reference Examples 73 to 75

Compounds 73, 74 and 75

Compounds 73, 74 and 75 were synthesized according to the method described in WO2005/035512.

Reference Examples 76 to 86

Compounds 76, 77, 78, 79, 80, 81, 82, 83, 84, 85 and 86

Compounds 76, 77, 78, 79, 80, 81, 82, 83, 84, 85 and 86 were synthesized in the same manner as that of Reference Example 47 by subjecting N-[4-acetyl-5-ethenesulfonylaminomethyl-5-phenyl-4,5-dihydro-1,3,4-thiadiazol-2-yl]-2,2-dimethylpropanamide, N-{2-[3-acetyl-5-(2-oxopyrrolidin-1-yl)-2-phenyl-2,3-dihydro-1,3,4-thiadiazol-2-yl]-methyl}vinylsulfonamide, N-{2-[3-acetyl-5-(2-oxopiperidino)-2-phenyl-2,3-dihydro-1,3,4-thiadiazol-2-yl]methyl}-vinylsulfonamide, obtained by the method described in WO2004/092147, or Compound 10 {N-[4-(2,2-dimethylpropionyl)-5-ethenesulfonylaminomethyl-5-phenyl-4,5-dihydro-1,3,4-thiadiazol-2-yl]-2,2-dimethylpropanamide} obtained in Reference Example 10 and a corresponding sulfanyl compound to the Michael addition reaction, respectively, and then subjecting the resultant to a reaction for removing protective group or the like, if necessary,

TABLE 28

| Ref. Ex. No. | Compound No. | APCI-MS m/z | Yield % |
|---|---|---|---|
| 76 | 76 | 502 (M + 1)$^+$ | — |
| 77 | 77 | 558 (M + 1)$^+$ | 44 |
| 78 | 78 | 517 (M + 1)$^+$ | 98 |
| 79 | 79 | 530 (M + 1)$^+$ | — |
| 80 | 80 | 516 (M + 1)$^+$ | 70 |
| 81 | 81 | 488 (M + 1)$^+$ | — |
| 82 | 82 | 486 (M + 1)$^+$ | 66 |
| 83 | 83 | 500 (M + 1)$^+$ | — |
| 84 | 84 | 578 (M + 1)$^+$ | 41 |
| 85 | 85 | 595 (M + 1)$^+$ | 40 |
| 86 | 86 | 565 (M + 1)$^+$ | 14 |

Reference Examples 87 to 90

Compounds 87, 88, 89 and 90

Compounds 87, 88, 89 and 90 were synthesized in the same manner as that of Reference Example 48 from a corresponding thiadiazoline derivative having aminomethyl group at the 5-position and a corresponding sulfanyl compound, respectively.

TABLE 29

| Ref. Ex. No. | Compound No. | APCI-MS m/z | Yield % |
|---|---|---|---|
| 87 | 87 | 472 (M + 1)⁺ | 12 |
| 88 | 88 | 486 (M + 1)⁺ | — |
| 89 | 89 | 558 (M + 1)⁺ | 5 |
| 90 | 90 | — | 20 |

Reference Examples 91 to 94

Compounds 91, 92, 93 and 94

Compounds 91, 92, 93 and 94 were synthesized according to the method described in WO2004/092147 or WO2004/111024.

TABLE 30

| Ref. Ex. No. | Compound No. | APCI-MS m/z | Yield % |
|---|---|---|---|
| 91 | 91 | 573 (M + 1)⁺ | 45 |
| 92 | 92 | 499 (M + 1)⁺ | 80 |
| 93 | 93 | 545 (M + 1)⁺ | — |
| 94 | 94 | 558 (M + 1)⁺ | — |

Reference Example A

Preparation of seed crystals of 2-(tert-butoxycarbonylamino)acetophenone thiosemicarbazone 2-(tert-Butoxycarbonylamino)acetophenone (3.00 g) was dissolved in methanol (21.0 mL). To the solution was added an aqueous solution (water: 9.0 mL) of thiosemicarbazide hydrochloride (3.11 g, 24.4 mmol) at room temperature. After the mixture was stirred at the same temperature for 30 minutes, water (12.0 mL) was added, and the mixture was stirred at room temperature for 20 minutes and then at 0° C. for 1 hour. The deposited solid was collected by filtration and washed with cooled 50% aqueous methanol (20 mL). The resulting solid was dried at 40° C. under reduced pressure to give seed crystals of 2-(tert-butoxycarbonylamino)acetophenone thiosemicarbazone (3.56 g, yield: 95.1%) as a white solid.

What is claimed is:

1. A method for therapeutic treatment of restenosis, which comprises administering a therapeutically effective amount of a thiadiazoline derivative or a pharmaceutically acceptable salt thereof represented by the general formula (0):

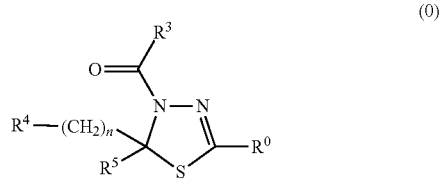

(0)

wherein, n represents an integer of 1 to 3,
$R^0$ represents (i) aryl which may be substituted with one to three substituents selected from the group consisting of halogen, hydroxy, cyano and lower alkyl, or (ii) -NR$^1$COR$^2$, wherein R$^1$ represents a hydrogen atom, R$^2$ represents lower alkyl, or $R^1$ and $R^2$ are combined together to represent alkylene,
$R^3$ represents lower alkyl,
$R^4$ represents
(i) a hydrogen atom,
(ii) NHR$^6$, wherein R$^6$ represents (a) lower alkyl which may be substituted with one or two substituents selected from the group consisting of hydroxy, lower alkoxy and NR$^{11}$R$^{12}$, wherein R$^{11}$ and R$^{12}$ are the same or different, and each represents lower alkanoyl which may be substituted with one or two substituents selected from the group consisting of amino, (lower alkyl)amino and di-(lower alkyl)amino; cycloalkyl; lower alkyl; (lower alkoxy)carbonyl; lower alkoxy; hydroxy or a hydrogen atom; SO$_2$R$^7$, wherein R$^7$ represents (1) lower alkyl which may be substituted with one or two substituents selected from the group consisting of (α) (lower alkyl)thio which may be substituted with one or two substituents selected from the group consisting of hydroxy, amino, lower alkoxy, (lower alkyl)amino and di-(lower alkyl)amino; (β) a nitrogen-containing heterocyclic group which may be substituted with one to three substituents selected from the group consisting of lower alkyl which may be substituted with hydroxy, amino, (lower alkyl)amino, or di-(lower alkyl)amino, oxo, hydroxy, sulfanyl, amino, lower alkoxy, methylenedioxy ethylenedioxy, (lower alkyl)thio, (lower alkyl)amino, di-(lower alkyl)amino, lower alkyl, aryl, formyl and lower alkanoyl; (γ) lower alkoxy; (δ) hydroxy, and (σ) NR$^{11}$R$^{12}$ (wherein R$^{11}$ and R$^{12}$ have the same meanings as those mentioned above, respectively), (2) amino, (3) (lower alkyl)amino, (4) di-(lower alkyl)amino, or (5) lower alkenyl; (c) COR$^8$, wherein R$^8$ represents (1) lower alkyl which may be substituted with one or two substituents selected from the group consisting of hydroxy, lower alkoxy, carboxy, phenyl, hydroxyphenyl, imidazolyl, guanidyl, methylthio and NR$^{11}$R$^{12}$, wherein
R$^{11}$ and R$^{12}$ have the same meanings as those mentioned above, respectively; (2) a nitrogen-containing aliphatic heterocyclic group which may be substituted with (lower alkoxy)carbonyl or oxo; or (3) lower alkoxy; (d) cycloalkyl; or (e) a hydrogen atom, or
(iii) CONHR$^9$, wherein R$^9$ represents lower alkyl which may be substituted with one or two substituents selected from the group consisting of hydroxy, lower alkoxy, carbamoyl, (lower alkyl)carbamoyl, di-(lower alkyl)carbamoyl and NR$^{11}$R$^{12}$ (wherein R$^{11}$ and R$^{12}$ have the same meanings as those mentioned above, respectively, and
R$^5$ represents aryl which may be substituted with one to three substituents selected from the group consisting of halogen, hydroxy, lower alkoxy, nitro, amino, cyano and carboxy.

2. The method according to claim 1, wherein the thiadiazoline derivative is a thiadiazoline derivative represented by the following formula (00):

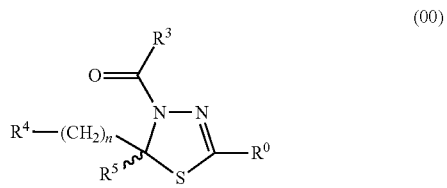

(00)

wherein R$^0$, R$^3$, R$^4$, R$^5$, and n have the same meanings as those mentioned above, respectively), which shows a negative value as a specific rotation at 20° C. for sodium D line (wavelength: 589.3 nm) when the thiadiazoline derivative or the pharmaceutical acceptable salt thereof is dissolved in methanol.

3. The method according to claim 1, wherein $R^4$ is
   (i) a hydrogen atom,
   (ii) $NHR^{6A}$, wherein $R^{6A}$ represents (a) lower alkyl which may be substituted with one or two substituents selected from the group consisting of hydroxy, lower alkoxy and $NR^{11A}R^{12A}$, wherein $R^{11A}$ and $R^{12A}$ are the same or different, and each represents lower alkyl, (lower alkoxy)carbonyl, lower alkoxy, hydroxy, or a hydrogen atom; (b) $SO_2R^7$, wherein $R^7$ has the same meaning as that mentioned above; (c) $COR^{8A}$, wherein $R^{8A}$ represents (1) lower alkyl which may be substituted with one or two substituents selected from the group consisting of hydroxy, lower alkoxy, carboxy, phenyl, hydroxyphenyl, imidazolyl, guanidyl, methylthio and $NR^{11A}R^{12A}$, wherein $R^{11A}$ and $R^{12A}$ have the same meanings as those mentioned above, respectively; (2) a nitrogen-containing aliphatic heterocyclic group which may be substituted with (lower alkoxy)carbonyl or oxo; or (3) lower alkoxy; or (d) a hydrogen atom, or
   (iii) $CONHR^{9A}$, wherein $R^{9A}$ represents lower alkyl which may be substituted with one or two substituents selected from the group consisting of hydroxy, lower alkoxy, carbamoyl, (lower alkyl)carbamoyl, di-(lower alkyl)carbamoyl and $NR^{11A}R^{12A}$, wherein $R^{11}$ and $R^{12A}$ have the same meanings as those mentioned above, respectively.

4. The method according to claim 1, wherein $R^4$ is
   (i) a hydrogen atom,
   (ii) $NHR^{6B}$, wherein $R^{6B}$ represents (a) lower alkyl which may be substituted with one or two substituents selected from the group consisting of hydroxy and $NR^{11}R^{12B}$, wherein $R^{11}$ and $R^{12B}$ are the same or different, and each represents lower alkyl or a hydrogen atom; (b) $SO_2R^{7B}$, wherein $R^{7B}$ represents (1) lower alkyl which may be substituted with one or two substituents selected from the group consisting of (α) (lower alkyl)thio which may be substituted with one or two substituents selected from the group consisting of hydroxy, amino, lower alkoxy, (lower alkyl)amino and di-(lower alkyl)amino; (β) a nitrogen-containing heterocyclic group which may be substituted with one to three substituents selected from the group consisting of lower alkyl which may be substituted with hydroxy, amino, (lower alkyl)amino, or di-(lower alkyl)amino, oxo, hydroxy, sulfanyl, amino, lower alkoxy, methylenedioxy, ethylenedioxy, (lower alkyl)thio, (lower alkyl)amino, di-(lower alkyl)amino, lower alkyl, aryl, formyl and lower alkanoyl; and (γ) $NR^{11BB}R^{12BB}$, wherein $R^{11BB}$ and $R^{12BB}$ are the same or different, and each represents lower alkanoyl which may be substituted with one or two substituents selected from the group consisting of amino, (lower alkyl)amino and di-(lower alkyl)amino, cycloalkyl, lower alkyl, or a hydrogen atom, (2) amino, (3) (lower alkyl)amino, (4) di-(lower alkyl)amino, or (5) lower alkenyl; (c) $COR^{8B}$, wherein $R^{8B}$ represents a nitrogen-containing aliphatic heterocyclic group which may be substituted with (lower alkoxy)carbonyl or oxo; or (d) a hydrogen atom, or
   (iii) $CONHR^{9B}$, wherein $R^{9B}$ represents lower alkyl which may be substituted with one or two substituents selected from the group consisting of hydroxy, lower alkoxy, carbamoyl, (lower alkyl)carbamoyl and di-(lower alkyl) carbamoyl.

5. The method according to claim 1, wherein $R^4$ is
   (i) a hydrogen atom,
   (ii) $NHR^{6C}$, wherein $R^{6C}$ represents (a) lower alkyl which may be substituted with one or two substituents selected from the group consisting of hydroxy and $NR^{11B}R^{12B}$, wherein $R^{11B}$ and $R^{12B}$ have the same meanings as those mentioned above, respectively; (b) $SO_2R^{7C}$, wherein $R^{7C}$ represents (1) lower alkyl which may be substituted with one or two substituents selected from the group consisting of (α) (lower alkyl)thio which may be substituted with one or two substituents selected from the group consisting of hydroxy and amino; (β) a nitrogen-containing heterocyclic group which may be substituted with one to three substituents selected from the group consisting of lower alkyl which may be substituted with hydroxy, oxo, hydroxy, sulfanyl, amino, (lower alkyl)thio and formyl; and (γ) $NR^{11C}R^{12C}$, wherein $R^{11C}$ and $R^{12C}$ are the same or different, and each represents lower alkanoyl which may be substituted with amino, cycloalkyl, lower alkyl, or a hydrogen atom; (2) di-(lower alkyl)amino, or (3) lower alkenyl; (c) $COR^{8C}_1$, wherein $R^{8C}$ represents a nitrogen-containing aliphatic heterocyclic group); or (d) a hydrogen atom, or
   (iii) $CONHR^{9C}$, wherein $R^{9C}$ represents lower alkyl which may be substituted with one or two substituents selected from the group consisting of hydroxy and carbamoyl.

6. The method according to claim 1, wherein $R^4$ is $NHR^{6B}$, wherein $R^{6B}$ has the same meaning as that mentioned above.

7. The method according to claim 1, wherein $R^4$ is $NHR^{6C}$, wherein $R^{6C}$ has the same meaning as that mentioned above.

8. The method according to claim 1, wherein $R^4$ is $NHSO_2R^7$, wherein $R^7$ has the same meaning as that mentioned above.

9. The method according to claim 1, wherein $R^4$ is $NHSO_2R^{7B}$, wherein $R^{7B}$ has the same meaning as that mentioned above.

10. The method according to claim 1, wherein $R^4$ is $NHSO_2R^{7C}$, wherein $R^{7C}$ has the same meaning as that mentioned above.

11. The method according to claim 1, wherein $R^4$ is $CONHR^{9C}$, wherein $R^{9C}$ has the same meaning as that mentioned above.

12. The method according to claim 1, wherein $R^4$ is $NHR^{6D}$, wherein $R^{6D}$ represents lower alkyl which may be substituted with one or two substituents selected from the group consisting of hydroxy and $NR^{11B}R^{12B}$, wherein $R^{11B}$ and $R^{12B}$ have the same meanings as those mentioned above, respectively, or a hydrogen atom.

13. The method according to claim 1, wherein $R^5$ is phenyl.

14. The method according to claim 1, wherein $R^3$ is methyl, ethyl, isopropyl or tert-butyl.

15. The method according to claim 1, wherein $R^0$ is $-NR^1COR^2$, wherein $R^1$ and $R^2$ have the same meanings as those mentioned above, respectively.

16. The method according to claim 15, wherein $R^1$ is a hydrogen atom.

17. The method according to claim 16, wherein $R^2$ is methyl or tert-butyl.

18. The method according to claim 15, wherein $R^1$ and $R^2$ are combined together to represent trimethylene or tetramethylene.

19. The method according to claim 1, wherein $R^0$ is aryl which may be substituted with one to three substituents selected from the group consisting of halogen, hydroxy, lower alkyl and cyano.

20. The method according to claim 1, wherein $R^0$ is aryl which may be substituted with halogen.

21. The method according to claim 1, wherein n is 1 or 2.

22. The method according to claim 2, wherein the thiadiazoline derivative is a thiadiazoline derivative represented by any one of the following formulas (a) to (r):

(a)
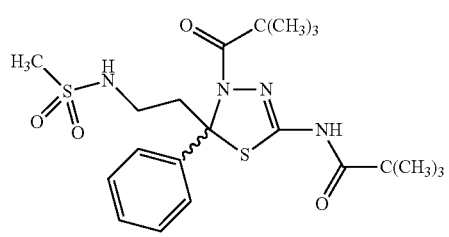
(b)
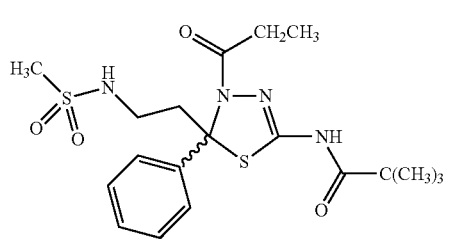
(c)
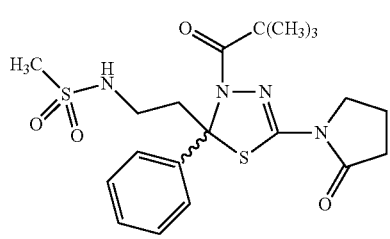
(d)
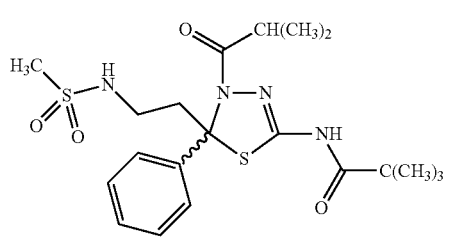
(e)
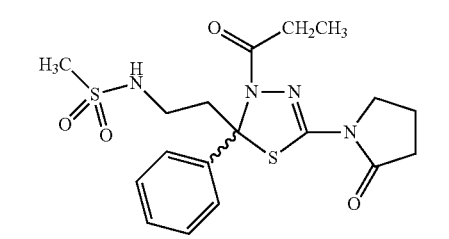
(f)
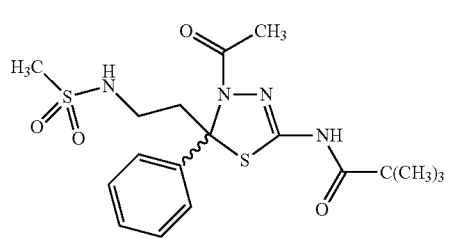
-continued
(g)
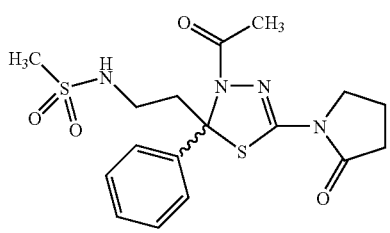
(h)
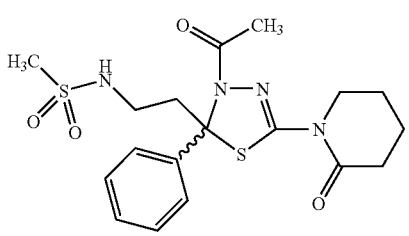
(i)
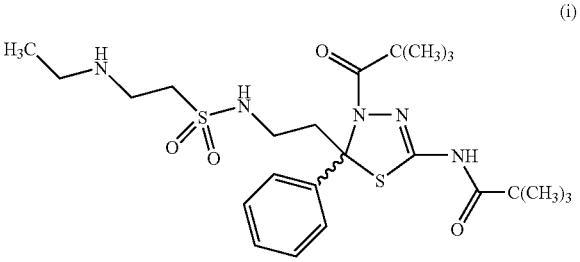
(j)
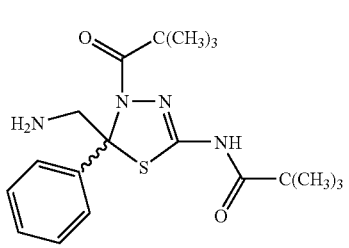
(k)
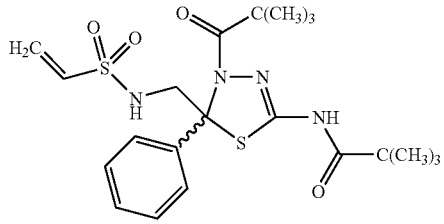
(l)
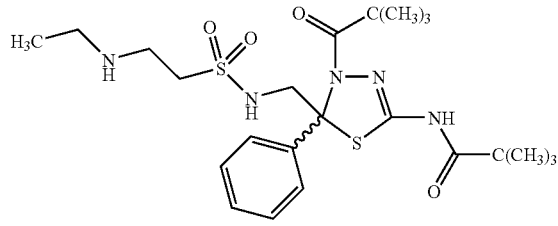

-continued (m)
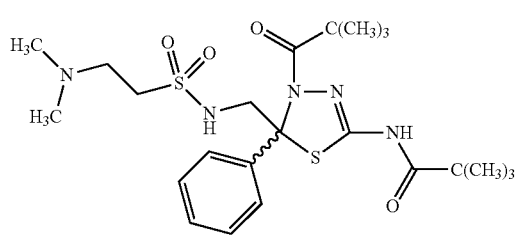

(n)
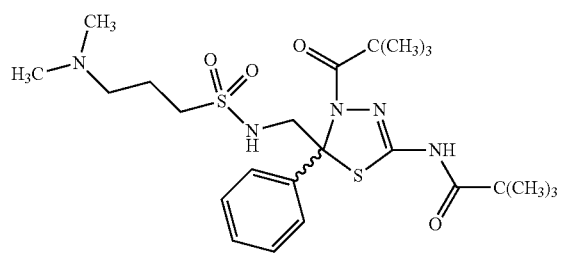

(p)
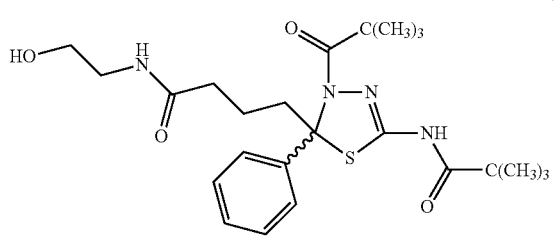

(q)
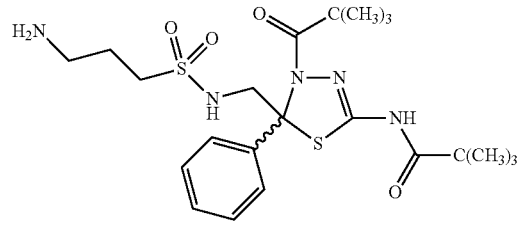

-continued (r)
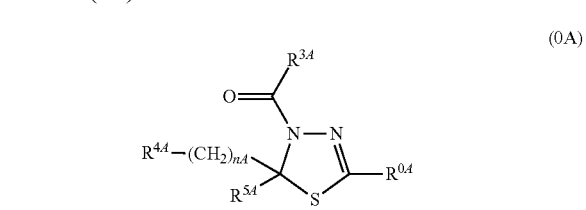

23. A thiadiazoline derivative represented by the general formula (0A):

(0A)
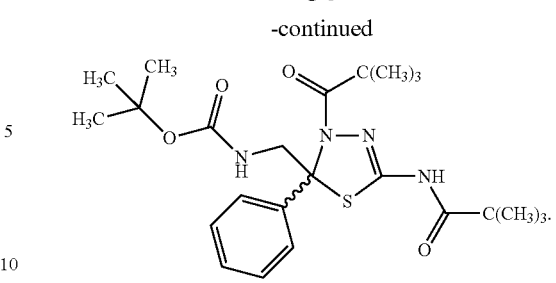

wherein, nA represents an integer of 1 to 3, $R^{0A}$ represents (i) aryl which may be substituted with one to three substituents selected from the group consisting of halogen, hydroxy, cyano and lower alkyl, or (ii) —$NR^1COR^2$, wherein $R^1$ represents a hydrogen atom, $R^2$ represents lower alkyl, or $R^1$ and $R^2$ are combined together to represent alkylene, $R^{3A}$ represents lower alkyl, $R^{4A}$ represents $NHSO_2R^{7AA}$, wherein $R^{7AA}$ represents lower alkyl substituted with a nitrogen-containing heterocyclic group which may be substituted with one to three substituents selected from the group consisting of lower alkyl which may be substituted with hydroxy, amino, (lower alkyl)amino, or di-(lower alkyl)amino, oxo, hydroxy, sulfanyl, amino, lower alkoxy, methylenedioxy, ethylenedioxy, (lower alkyl)thio, (lower alkyl)amino, di-(lower alkyl)amino, lower alkyl, aryl, formyl and lower alkanoyl, provided that when $R^{0A}$ is 2,2-dimethylpropanoylamino, $R^{3A}$ is methyl, and nA is 1, $R^{7AA}$ is not morpholinoethyl, $R^{5A}$ represents aryl which may be substituted with one to three substituents selected from the group consisting of halogen, hydroxy, lower alkoxynitro, amino, cyano and carboxy, or a pharmaceutically acceptable salt thereof.

* * * * *

UNITED STATES PATENT AND TRADEMARK OFFICE
CERTIFICATE OF CORRECTION

PATENT NO. : 7,910,611 B2  
APPLICATION NO. : 11/993757  
DATED : March 22, 2011  
INVENTOR(S) : Ryuichiro Nakai et al.

Page 1 of 1

It is certified that error appears in the above-identified patent and that said Letters Patent is hereby corrected as shown below:

At column 78, line 15 (Claim 1, line 25), "atom; $SO_2R^7$" should read --atom; (b) $SO_2R^7$--.

At column 79, line 25 (Claim 3, line 24), "$R^{11}$" should read --$R^{11A}$--.

At column 79, line 31 (Claim 4, line 5), $NR^{11}R^{12B}$" should read --$NR^{11B}R^{12B}$--.

At column 79, line 32 (Claim 4, line 6), "$R^{11}$" should read --$R^{11B}$--.

At column 84, line 44 (Claim 23, line 26), "alkoxynitro," should read --alkoxy, nitro,--.

Signed and Sealed this
Twenty-ninth Day of November, 2011

David J. Kappos
*Director of the United States Patent and Trademark Office*